United States Patent
Oku et al.

(10) Patent No.: US 7,713,926 B2
(45) Date of Patent: May 11, 2010

(54) **METHOD OF PRODUCING PARTIAL PEPTIDE OF ENOLASE PROTEIN FROM *PLASMODIUM FALCIPARUM***

(75) Inventors: Hiroyuki Oku, Maebashi (JP); Kazuto Omi, Maebashi (JP); Keisuke Kuriyama, Sendal (JP); Jyunya Yamamoto, Kiryu (JP); Keiichi Yamada, Kiryu (JP); Ryoichi Katakai, Kiryu (JP); Kumiko Sato, Yoshioka-machi (JP); Mamoru Suzuki, Takasaki (JP); Shin-ichiro Kawazu, Tokyo (JP); Shigeyuki Kano, Tokyo (JP)

(73) Assignee: National University Corporation Gunma University, Maebashi-shi, Gunma (JP)

( * ) Notice: Subject to any disclaimer, the term of this patent is extended or adjusted under 35 U.S.C. 154(b) by 501 days.

(21) Appl. No.: 11/663,962

(22) PCT Filed: Sep. 28, 2005

(86) PCT No.: PCT/JP2005/017851

§ 371 (c)(1),
(2), (4) Date: Mar. 28, 2007

(87) PCT Pub. No.: WO2006/035815

PCT Pub. Date: Apr. 6, 2006

(65) Prior Publication Data

US 2007/0269377 A1 Nov. 22, 2007

(30) Foreign Application Priority Data

Sep. 28, 2004 (JP) .............................. 2004-281518

(51) Int. Cl.
*A61K 38/00* (2006.01)
*C07K 1/00* (2006.01)
(52) U.S. Cl. .............................. 514/2; 530/333; 530/344
(58) Field of Classification Search ....................... None
See application file for complete search history.

(56) References Cited

U.S. PATENT DOCUMENTS

2005/0208078 A1* 9/2005 Hoffman et al. ......... 424/272.1
2005/0266017 A1* 12/2005 Druilhe et al. ........... 424/191.1

FOREIGN PATENT DOCUMENTS

JP 2002-371098 12/2002
JP 2002-371098 A 12/2002

OTHER PUBLICATIONS

International Preliminary Report on Patentability dated Apr. 12, 2007 for International Patent Application No. PCT/JP2005/017851.
J.L. Vennerstrom et al., *Identification of an Antimalarial Synthetic Trioxalane Drug Development Candidate*, Nature, vol. 430, No. 7002, Aug. 19, 2004, pp. 900-904.
H. Oku et al., *Addition of a Peptide Fragment on an a-Helical Depsipeptide Induces α/3$_{10}$-Conjugated Helix: Synthesis, Crystal Structure, and CD Spectra of Boc-Leu-Leu-Ala-(Leu-Leu-Lac)$_3$-Leu-Leu-OEt*, Biopolymers, vol. 75, No. 3, Oct. 15, 2004, pp. 242-254.
R. Katakai et al., *Synthesis of Sequential Polydepsipeptides Utilizing a New Approach for the Synthesis of Depsipeptides*, Biopolymers, vol. 73, No. 6, Apr. 15, 2004, pp. 641-644.
International Search Report dated Jan. 17, 2006 for International Patent Application No. PCT/JP2005/017851.

* cited by examiner

*Primary Examiner*—Mark Navarro
(74) *Attorney, Agent, or Firm*—Hogan & Hartson LLP

(57) ABSTRACT

The peptide production method of the present invention produces a peptide (SEQ ID NO: 1) of a protein from *Plasmodium falciparum*, which is effective as a malaria vaccine. The method produces the peptide of SEQ ID NO: 1 by linking the fragments (i) through (v) shown below:

(v) Asn-Asn-Asp-Xaa (SEQ ID NO: 2);
(iv) Asp-Phe-Lys-Thr-Pro (SEQ ID NO: 3);
(iii) Asn-Lys-Thr-Tyr-Asp-Leu (SEQ ID NO: 4);
(ii) Phe-Tyr-Asn-Ser-Glu (SEQ ID NO: 5); and
(i) Xaa-Ala-Ser-Glu (SEQ ID NO: 6), where 'Xaa' in (i) and (v) represents zero or any arbitrary number of amino acid residues.

18 Claims, 8 Drawing Sheets

US 7,713,926 B2

METHOD OF PRODUCING PARTIAL PEPTIDE OF ENOLASE PROTEIN FROM *PLASMODIUM FALCIPARUM*

CROSS REFERENCE TO RELATED APPLICATIONS

This application claims priority under 35 U.S.C. §371 to International Application No. PCT/JP2005/017851, filed Sep. 28, 2005, which claims priority Japanese Patent Application No. 2004-281518, filed Sep. 28, 2004, both of which applications are expressly incorporated herein by reference in their entirety.

1. TECHNICAL FIELD

The present invention relates to a method of producing a partial peptide of enolase protein from *Plasmodium falciparum*. The present invention also relates to a method of producing medicines including a peptide with an ability of inducing an immunological response to *Plasmodium falciparum* by taking advantage of an immunological reaction in human or another animal, a diagnostic agent of the immunological state of malaria infection, and an immunological antigen peptide of inhibiting the proliferation of *Plasmodium falciparum*.

2. BACKGROUND ART (1) Present Status of Malaria and Other Infections

In spite of the optimistic prospective of overcoming various infections, the global transportation of people and products, the development-inducing global environmental change, and the drastic change of various social activities have significantly and rather adversely changed the circumstances surrounding the infections. For example, the popularity of overseas travels and the destruction of rainforests induce tropical diseases, and the heavy use and the abuse of anti-infectives lead to the appearance of drug-resistant viruses and bacteria.

Among the variety of infections, especially the actions against malaria as a tropical protozoal infection are slow and insufficient. The number of malaria patients amounts to approximately 300 to 500 millions per year including 1.5 to 2.7 million deaths (see WHO report, 1999). Among four human-infecting protozoa species, *Plasmodium falciparum* is most severe and deadly. Malaria has the massive impact on the human health and also causes the economic recession and social instability in African states.

It is often pointed out that the destruction of rainforests and the global warming have contribution to the increasing number of malaria patients. According to the reports of the International Panel on Climate Change (1996 and 1998), a potential increase of 50 to 80 million new malaria patients would be predicted by a temperature rise of 2° C. by the global warming. With the wide spread of overseas travels, the number of malaria-(imported malaria-) infected individuals in Japan has an increasing tendency to 120 to 150 patients per year from 50 to 70 patients per year in 1980s.

(2) Prior Arts and Their Problems

Many of currently used malaria medications include the patent loyalties and are thus rather expensive. This interferes with the widespread of the malaria medication in the developing countries. There are some inexpensive malaria drugs like chloroquine. The limitless use of these popular drugs leads to the high degree of drug resistance.

There are many malaria-related issues to be solved. The domestic and international pharmaceutical industries have not actively been involved in development of therapeutic and preventive medicines for malaria. The target of their research and development is focused on the age-related disorders and diseases, which have the greater importance for the developed countries. Another reason for their sluggish attitude is a relatively small market of the products for the developing countries. The existing companies may thus not be sufficiently reliable for development of novel antimalarial pharmaceutical substances. There is a need of commercially production and distribution of effective but inexpensive therapeutic, preventive, and inspective medicines for malaria.

The compound "mefloquine" developed during the Vietnam War is the most commonly used antimalarial drug at present. The newer antimalarial drug is Malarone approved in the US in 2000. This is, however, only the diversion of a known substance to the therapeutic medicine for malaria. The latest study has proposed an inexpensive synthetic compound OZ227 having the similar action mechanism to that of a known natural therapeutic agent 'artemisinin' (see Non-Patent Reference 1).

The conventional anti-*Plasmodium falciparum* drugs, however, generally have severe side effects including headache and nausea. Administration of such medicines for the preventive purpose is thus not generally recommendable. Some of the conventional antimalarial substances, for example, quinine and chloroquine, are deleterious. Peptide vaccines mainly composed of amino acids, on the other hand, exert only desired preventive immunological effects, while being less poisonous and deleterious than the conventional antimalarial substances.

The disadvantage of the peptide vaccine is the potentially different preventive immunological effects among different individuals. The prevalence rate of malaria is high in the epidemic regions. The simple reduction in the risk of malaria development is thus expected to have sufficient contribution to the decrease in the number of sufferers and the number of deaths.

Over many years, the inventors of the present invention have been occupied in development of peptide vaccines, based on the epidemiologic study in the epidemic regions in combination with the molecular analyses in the laboratory scale. As the result of the extensive studies, the inventors have found that enolase, which is a glycolytic enzyme produced from the *Plasmodium falciparum*-infected human, functions as a protective immune molecule against malaria and have developed peptide vaccines by taking advantage of such finding.

For example, the inventors noted and examined a partial amino acid sequence of enolase from *Plasmodium falciparum* shown in SEQ ID NO: 12.

A small amount (several milligram level) of a peptide including this partial amino acid sequence (SEQ ID NO: 12) was synthesized and was used as an artificial antigen. The use of this artificial antigen induced an immunological response to *Plasmodium falciparum*, enabled diagnosis of the immunological state of malaria infection (immunological inspection), and derivatively produced an immunological antigen for inhibiting the proliferation of *Plasmodium falciparum*. These research results are reported in Patent Reference 1, together with the research results on synthetic peptides comprising other partial amino acid sequences of enolase protein from *Plasmodium falciparum*.

The peptide vaccine is conventionally produced by the solid-phase synthesis or by the genetic recombination. Neither the solid-phase synthesis technique nor the genetic recombination technique requires the specific skill or experience for producing any sequences. The solid-phase synthesis technique, however, generally has a lower synthesis yield for a longer chain substance and gives a relatively poor yield of a final product after purification. The genetic recombination technique also generally gives a poor yield of a final product.

The laboratory scale synthesis of the peptide including the partial amino acid sequence of enolase from *Plasmodium falciparum* (SEQ ID NO: 12) by the solid-phase synthesis technique gives a yield of only several hundred micrograms to several milligrams. The synthesis of the peptide by the genetic recombination technique with culture of *Eschelichia coli* in a relatively large (laboratory scale) 2-liter vessel gives a yield of only 1 to 2 milligrams (as the vaccine for only one person). Even the genetic recombination with an industrially largest-level 1000-liter vessel gives a yield of only 500 to 1000 milligrams (as the vaccine for about 500 people).

Another conventionally known technique potentially applicable for synthesis of the partial peptide (SEQ ID NO: 12) is fragment condensation. In this case, synthesis of a fragment having a glutamic acid residue at the terminal is the most important issue to be solved. Introduction of trichloroethyl ester group or another optional ester group into N-α-protected-L-glutamic-γ-benzyl ester is essential for obtaining a synthesis intermediate N-α-t-butoxycarbonyl-L-glutamic-γ-benzyl ester-α-trichloroethyl ester described later in Examples and other optional synthesis intermediates N-α-protected-L-glutamic-γ-benzyl ester-α-protected esters. According to Non-Patent Reference 2, esterification of N-α-protected-L-glutamic-γ-benzyl ester for the purpose of protecting the α-site carboxylic acid group has a high potential for racemization. It is thus believed in the art that N-α-protected-L-glutamic-γ-benzyl ester is not suitable for the synthesis of a peptide. There has been no synthesis tried after the report of the Non-Patent Reference 2.

The synthesis of the partial peptide (SEQ ID NO: 12) by the conventional fragment condensation technique in consideration of the potential racemization requires large fragments having at least 14 residues. The desired size of each fragment is generally 5 to 7 residues at the maximum for the good yields of synthesis and purification. Namely the conventional fragment condensation technique is not adequate for the efficient large-scale synthesis of the peptide.

As used herein: Patent Reference 1: Japanese Patent Laid-Open Gazette No. 2002-371098; Non-Patent Reference 1: pages 900-903, vol. 430, 2004, Nature; and Non-Patent Reference 2: pages 1962-1965, vol. 47, 1982, Journal of Organic Chemistry.

DISCLOSURE OF THE INVENTION

The present invention provides a method that is suitable for large-scale synthesis of a peptide required for inducing an immunological response to *Plasmodium falciparum* by taking advantage of an immunological reaction in human or another animal. More specifically, the present invention is directed to a method that is suitable for large-scale syntheses of an immunological antigen sequence that is used for inhibiting the proliferation of *Plasmodium falciparum* and for diagnosing the immunological state of malaria infection.

The inventors of the present invention noted and intensively studied the chemical syntheses in the homogeneous reaction system known as the fragment condensation and planned divisional syntheses of five segments. The examination target was especially placed on the syntheses of two fragments having glutamic acid residues at their terminals, that is, the peptides (II) Phe-Tyr($R_3$)-Asn($R_4$)-Ser($R_5$)-Glu($R_6$) (SEQ ID NO: 10) and (I) Xaa-Ala-Ser($R_1$)-Glu($R_2$) (SEQ ID NO: 11). Based on such examinations, the inventors eventually succeeded in divisional syntheses of the five segments.

Among the fragments, the conventionally unavailable synthesis intermediate N-α-protected-L-glutamic-γ-benzyl ester-α-protected ester was used as the starting material for the peptides (I) and (II). We thoroughly examined the synthesis conditions and surprisingly managed to obtain the non-racemized L-form product of the high purity with high efficiency.

Then, we tried to condense the five fragments sequentially or to condense after linking to some larger partial peptides. The inventors examined the optimum condensing agent and eventually succeeded in condensing the five fragments into one protected peptide chain.

The inventors have developed a method that enables a large-scale synthesis of a peptide having a partial sequence of enolase from *Plasmodium* or its analog by synthesizing an N-x-protected-L-glutamic-γ-benzyl ester-α-protected ester, synthesizing five segments and condensing the five segments into one protected peptide chain, and thus completed the present invention. Here the terminology 'large-scale' implies production of 100-fold or greater scale than the conventional genetic recombination. Even one cycle of laboratory scale synthesis by the method of the present invention yields approximately 100 to 500 milligrams of the peptide (as the vaccine for about 50 to 250 people). Only two to four cycles of the laboratory scale synthesis has the peptide production capacity equivalent to that of industrial genetic recombination equipment of the world-largest scale. Industrial scale synthesis by the method of the present invention is expected to yield the peptide vaccine for several million people, which satisfies the annual global demand.

The present invention includes:

A method for producing a peptide having an amino acid sequence of Xaa Ala Ser Glu Phe Tyr Asn Ser Glu Asn Lys Thr Tyr Asp Leu Asp Phe Lys Thr Pro Asn Asn Asp Xaa (SEQ ID NO: 1), including linking the following fragments (i) through (v) to produce said peptide:

(v) Asn-Asn-Asp-Xaa (SEQ ID NO: 2);
(iv) Asp-Phe-Lys-Thr-Pro (SEQ ID NO: 3);
(iii) Asn-Lys-Thr-Tyr-Asp-Leu (SEQ ID NO: 4);
(ii) Phe-Tyr-Asn-Ser-Glu (SEQ ID NO: 5); and
(i) Xaa-Ala-Ser-Glu (SEQ ID NO: 6), where 'Xaa' in (i) and (v) represents zero or any arbitrary number of amino acid residues.

(2) The production method according to (1), wherein the peptide of SEQ ID NO: 1 is produced by linking the modified peptides (I) through (V) shown below and performing subsequent deprotection:

(V)Asn($R_{15}$)Asn($R_{16}$)-Asp($R_{17}$)-Xaa(SEQ ID NO: 7)

where $R_{15}$ and $R_{16}$ represent $(C_6H_5)_3C—$ or no protecting group, and $R_{17}$ represents $C_6H_5CH_2—O—$ or or $(CH_3)_3C—O—$;

(IV) Asp($R_{12}$)-Phe-Lys($R_{13}$)-Thr($R_{14}$)-Pro (SEQ ID NO: 8)

where $R_{12}$ represents $C_6H_5CH_2—$ or $(CH_3)_3C—$, $R_{13}$ represents $(CH_3)_3C—O—CO—$, $C_6H_5CH_2—O—CO—$, 2-chlorobenzyloxycarbonyl- or 9-fluorenylmethoxycarbonyl-, and $R_{14}$ represents $C_6H_5CH_2—$ or $(CH_3)_3C—$;

(III) Asn($R_7$)-Lys($R_8$)-Thr($R_9$)-Tyr($R_{10}$)-Asp($R_{11}$)-Leu (SEQ ID NO: 9)

where $R_7$ represents $(C_6H_5)_3C—$ or no protecting group, $R_8$ represents $(CH_3)_3C—O—CO—$, $C_6H_5CH_2—O—CO—$, 2-chlorobenzyloxycarbonyl- or 9-fluorenylmethoxycarbonyl-, $R_9$ represents $C_6H_5CH_2—$ or $(CH_3)_3C—$, $R_{10}$ represents $C_6H_5$—$CH_2$—, $Cl_2$—$C_6H_3$—$CH_2$—, or $(CH_3)_3C$—, and $R_{11}$ represents $C_6H_5CH_2$— or $(CH_3)_3C$—;

(II) Phe-Tyr($R_3$)-Asn($R_4$)-Ser($R_5$)-Glu($R_6$) (SEQ ID NO: 10)

where $R_3$ represents $C_6H_5$—$CH_2$—, $Cl_2$—$C_6H_3$—$CH_2$—, or $(CH_3)_3C$—, $R_4$ represents $(C_6H_5)_3C$— or no protecting group, $R_5$ represents $C_6H_5CH_2$— or $(CH_3)_3C$—, and $R_6$ represents $C_6H_5CH_2$—O— or $(CH_3)_3C$—O—; and (I) Xaa-Ala-Ser($R_1$)-Glu($R_2$) (SEQ ID NO: 11)

where $R_1$ represents $C_6H_5CH_2$— or $(CH_3)_3C$—, and $R_2$ represents $C_6H_5CH_2$—O— or $(CH_3)_3C$—O—.

(3) The production method according to items 1 or 2, wherein said peptides are condensed by using a combination of 1-ethyl-3-(3-dimethylaminopropyl)carbodiimide and 1-hydroxybenzotriazole, a combination of 2-(1H-benzotriazol-1-yl)-1,1,3,3-tetramethyluronium hexafluorophosphate and 1-hydroxybenzotriazol, or O-(7-azabenzotriazol-1-yl)-1,1,3,3-tetramethyluronium hexafluorophosphate.

(4) A method for producing a peptide of SEQ ID NO: 1 having a modification in its terminus, including:

producing the peptide of SEQ ID NO: 1 by the method according to any one of (1) to (3), and adding a sugar chain sequence, a peptide, a protein, a polysaccharide, a metal complex, a polymer carrier, a gel, a film, latex particles, metal fine particles, or a plastic plate to an N terminus and/or a C terminus of the peptide of SEQ ID NO: 1.

(5) A method for manufacturing a preventive or therapeutic medicine for *Plasmodium falciparum* infection, or a diagnostic agent for *Plasmodium falciparum* infection, including:

producing the peptide of SEQ ID NO: 1 by the method according to one of (1) to (3); and formulating the produced peptide of SEQ ID NO: 1 with a pharmaceutically acceptable carrier.

(6) A method of manufacturing a preventive or therapeutic medicine for *Plasmodium falciparum* infection, or a diagnostic agent for *Plasmodium falciparum* infection, including:

producing the terminal-modified peptide of SEQ ID NO: 1 by the method of (4); and formulating the terminal-modified peptide of SEQ ID NO: 1 with a pharmaceutically acceptable carrier.

(7) N-α-t-butoxycarbonyl-L-glutamic-γ-benzyl-α-trichloroethyl ester that essentially consists of an L-form.

(8) A method for producing a peptide including using the N-α-t-butoxycarbonyl-L-glutamic-γ-benzyl-α-trichloroethyl ester according to item (7).

The accompanying drawings, which are included to provide a further understanding of the invention and are incorporated in and constitute a part of this specification, illustrate embodiments of the invention and together with the description serve to explain the principles of the invention. In the drawings:

DESCRIPTION OF THE PREFERRED EMBODIMENTS

Figure 1:
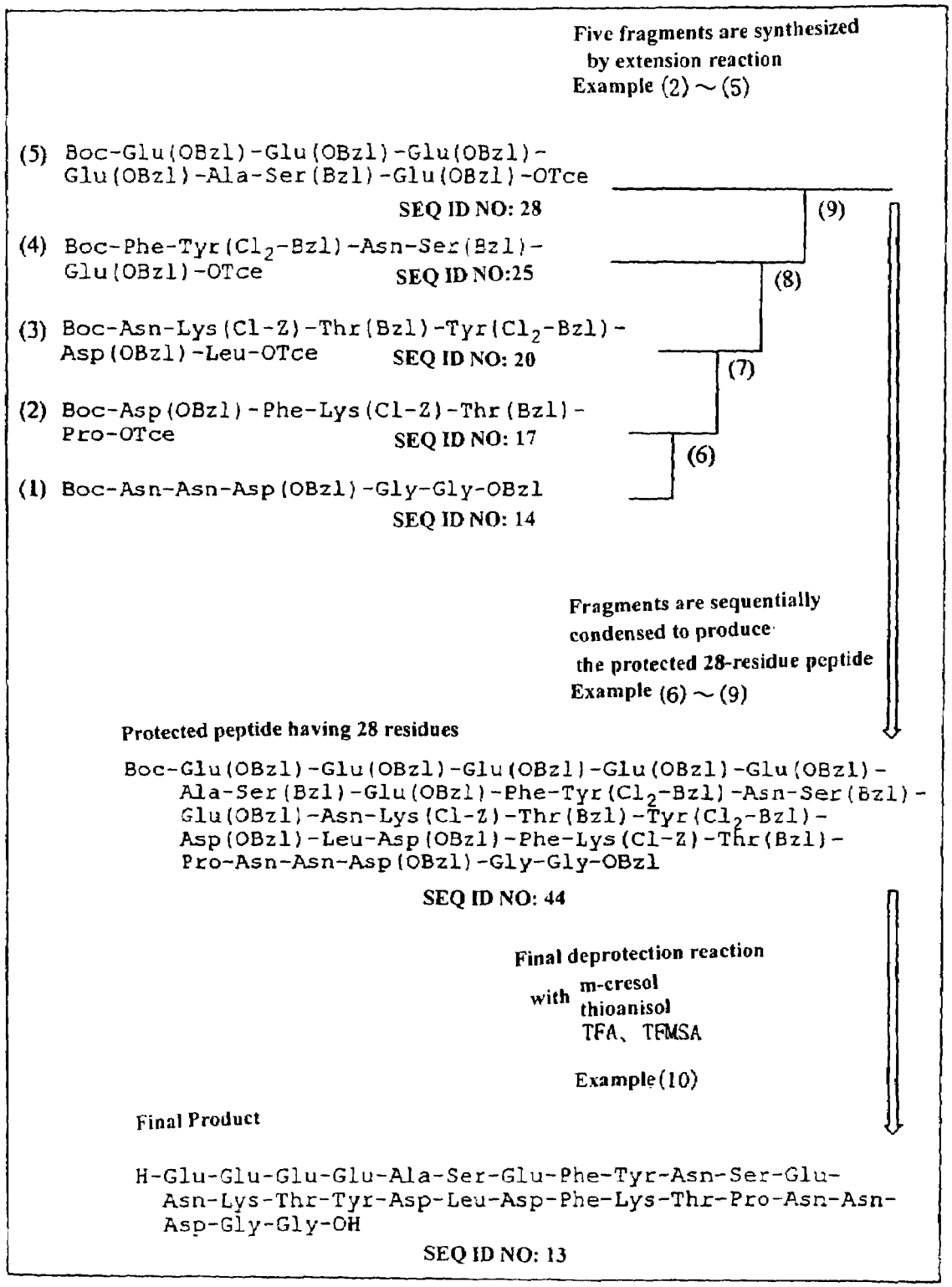
FIG. 1 is a flowchart showing a synthesis procedure of a peptide compound H-Glu-Glu-Glu-Glu-Ala-Ser-Glu-Phe-Tyr-Asn-Ser-Glu-Asn-Lys-Thr-Tyr-Asp-Leu-Asp-Phe-Lys-T hr-Pro-Asn-Asn-Asp-Gly-Gly-OH (SEQ ID NO: 13) as one example of the present invention.

In the present invention, the fragments (i) through (v) shown below are linked to produce a peptide having an amino acid sequence of Xaa Ala Ser Glu Phe Tyr Asn Ser Glu Asn Lys Thr Tyr Asp Leu Asp Phe Lys Thr Pro Asn Asn Asp Xaa (SEQ ID NO: 1):

(v) Asn-Asn-Asp-Xaa (SEQ ID NO: 2);
(iv) Asp-Phe-Lys-Thr-Pro (SEQ ID NO: 3);
(iii) Asn-Lys-Thr-Tyr-Asp-Leu (SEQ ID NO: 4);
(ii) Phe-Tyr-Asn-Ser-Glu (SEQ ID NO: 5); and
(i) Xaa-Ala-Ser-Glu (SEQ ID NO: 6), where 'Xaa' in the (i) and (v) represents zero, one, or plural, that is, any arbitrary number of, amino acid residues. The number of the amino acid residues included in 'Xaa' is not specifically restricted, as long as the resulting peptide of SEQ ID NO: 1 has the ability of inducing an immunological response to *Plasmodium falciparum*. The preferable number of the amino acid residues included in 'Xaa' is in the range of 0 to 20. In the (i) and (v), 'Xaa' may further include a carrier, in addition to the amino acid residues.

The peptides (i) through (v) may be produced by any conventional peptide synthesis technique but are preferably obtained by the solution phase reaction.

The peptide (ii) and the peptide (i) with Xaa=zero amino acid residue have L-glutamic acid at their C terminals. The conventionally unavailable N-α-protected-L-glutamic-γ-benzyl ester-α-protected ester or more specifically N-α-t-butoxycarbonyl-L-glutamic-γ-benzyl-α-trichloroethyl ester produced by the inventors of the present invention is preferably used as the reaction starting material for syntheses.

For production of the peptide of SEQ ID NO: 1, the peptides (i) through (v) may be linked sequentially one by one from one end peptide (i) or from the other end peptide (v), that is, from the fragment at the N-terminal or from the fragment at the C-terminal of the peptide of SEQ ID NO: 1. Another available procedure may first link some of the peptides, for example, (i) and (ii), to one larger fragment and the others of the peptides, for example, (iii), (iv), and (v), to another larger fragment and link the two larger fragments.

Prior to the linkage of peptide fragments, it is preferable to protect the terminals of the fragments, which are not involved in the linkage reaction, as well as the reactive side chains of these fragments. For example, in the case of linkage of (ii) Asp-Phe-Lys-Thr-Pro (SEQ ID NO: 3) with (iii) Asn-Lys-Thr-Tyr-Asp-Leu (SEQ ID NO: 4), the synthesis procedure preferably protects Asp at the amino terminal of (ii), Leu at the carboxyl terminal of (iii), and all the reactive side chains of these peptides.

Preferable examples of the protecting group at the amino terminal include $(CH_3)_3C$—O—CO—, $C_6H_5CH_2$—O—CO—, and 9-fluorenylmethoxycarbonyl-. Preferable examples of the protecting group at the carboxyl terminal include —O—$CH_2$—$CCl_3$, —O—$CH_2$—CO—$C_6H_5$, and —O—$CH_2$—$C_6H_5$.

The protecting groups for protection of the reactive side chains are appropriately selected depending on the amino acids. The following shows examples of side chain-protected fragments (i) through (v):

(V) Asn($R_{15}$)-Asn($R_{16}$)-Asp($R_{17}$)-Xaa(SEQ ID NO: 7)

where $R_{15}$ and $R_{16}$ represent side chain protecting groups of asparagine residue (for example, $(C_6H_5)_3C$—) or no protecting group, and $R_{17}$ represents a side chain protecting group of aspartic acid group (for example, $C_6H_5CH_2$—O— or $(CH_3)_3C$—O—);

(IV) Asp($R_{12}$)-Phe-Lys($R_{13}$)-Thr($R_{14}$)-Pro(SEQ ID NO: 8)

where $R_{12}$ represents a side chain protecting group of aspartic acid group (for example, $C_6H_5CH_2$— or $(CH_3)_3C$—), $R_{13}$ represents a side chain protecting group of lysine residue (for example, $(CH_3)_3C$—O—CO—, $C_6H_5CH_2$—O—CO—, 2-chlorobenzyloxycarbonyl- or 9-fluorenylmethoxycarbonyl-), and $R_{14}$ represents a side chain protecting group of threonine residue (for example, $C_6H_5CH_2$— or $(CH_3)_3C$—);

(III) Asn($R_7$)-Lys($R_8$)-Thr($R_9$)-Tyr($R_{10}$)-Asp($R_{11}$)-Leu (SEQ ID NO: 9)

where $R_7$ represents a side chain protecting group of asparagine residue (for example, $(C_6H_5)_3C$—) or no protecting group, $R_8$ represents a side chain protecting group of lysine residue (for example, $(CH_3)_3C$—O—CO—, $C_6H_5CH_2$—O—CO—, 2-chlorobenzyloxycarbonyl- or 9-fluorenylmethoxycarbonyl-), $R_9$ represents a side chain protecting group of threonine residue (for example, $C_6H_5CH_2$— or $(CH_3)_3C$—), $R_{10}$ represents a side chain protecting group of tyrosine residue (for example, $C_6H_5$—$CH_2$—, $Cl_2$—$C_6H_3$—$CH_2$—, or $(CH_3)_3C$—), and $R_{11}$ represents a side chain protecting group of aspartic acid group (for example, $C_6H_5CH_2$— or $(CH_3)_3C$—);

(II) Phe-Tyr($R_3$)-Asn($R_4$)-Ser($R_5$)-Glu($R_6$) (SEQ ID NO: 10)

where $R_3$ represents a side chain protecting group of tyrosine residue (for example, $C_6H_5$—$CH_2$—, $Cl_2$-$C_6H_3$—$CH_2$—, or $(CH_3)_3C$—), $R_4$ represents a side chain protecting group of asparagine residue (for example, $(C_6H_5)_3C$— or no protecting group), $R_5$ represents a side chain protecting group of serine residue (for example, $C_6H_5CH_2$— or $(CH_3)_3C$—), and $R_6$ represents a side chain protecting group of aspartic acid group (for example, $C_6H_5CH_2$—O— or $(CH_3)_3C$—O—)

(I) Xaa-Ala-Ser($R_1$)-Glu($R_2$) (SEQ ID NO: 11)

where $R_1$ represents a side chain protecting group of serine residue (for example, $C_6H_5CH_2$— or $(CH_3)_3C$—), and $R_2$ represents a side chain protecting group of glutamic acid residue (for example, $C_6H_5CH_2$—O— or $(CH_3)_3C$—O—).

The linkage of the respective fragments follows a conventional peptide condensation reaction, preferably using a condensing agent. Desirable examples of the condensing agent include a combination of 1-ethyl-3-(3-dimethylaminopropyl) carbodiimide and 1-hydroxybenzotriazole, a combination of 2-(1H-benzotriazol-1-yl)-1,1,3,3-tetramethyluronium hexafluorophosphate and 1-hydroxybenzotriazol, or O-(7-azabenzotriazol-1-yl)-1,1,3,3-tetramethyluronium hexafluorophosphate alone. The condensation reaction is preferably performed in the solution phase for the enhanced yield.

Deprotection of the linked peptides yields the peptide of SEQ ID NO: 1. The deprotection follows a conventionally known method.

For the easy induction of an immunological reaction, the peptide of the present invention is desirably designed and produced to stabilize the high-order structure of enolase from *Plasmodium falciparum*. The terminology "immunological response" in the specification hereof is the concept including both cellular immunological responses and humoral immunological responses. The "cellular immunological responses" means immunological responses caused by, for example, macrophages, natural killer cells (NK cells), eosinophils, and T cells. The "known cellular immunological response" to *Plasmodium falciparum* is an immunological response caused by killer T cells. The "known humoral immunological responses" means immunological responses caused by host-derived antibodies that specifically binds to proteins and sugar chains from *Plasmodium falciparum*. The antigen peptide produced by the present invention desirably has the ability of inducing an antibody as the humoral immunological response.

More specifically, a terminal-modified peptide is preferably produced by introduction of a compound for inducing a high-order structure into at least either of the amino terminal and the carboxyl terminal in the peptide of SEQ ID NO: 1. The high-order structure is easily recognizable by macrophages, NK cells, T cells, and other immunological cells, as well as by antibodies.

Typical examples of the compound for inducing the high-order structure include sugar chain sequences, peptide sequences, proteins, polysaccharides, metal complexes, polymer carriers, gels, films, latex particles, metal fine particles, and plastic plates.

Any of these modifier compounds may be introduced to either or both of the amino terminal and the carboxyl terminal in the peptide of SEQ ID NO: 1 by a bond corresponding to the type of the modifier compound, for example, by covalent bond, ionic bond, or coordination bond.

A peptide-bound film is prepared, for example, by the spin cast method. The presence of an antibody included in a test sample is detectable by placing dots of the test sample on the prepared peptide-bound film. Peptide-bound latex particles are prepared, for example, by emulsion polymerization or by suspension polymerization. The prepared peptide-bound latex particles are usable for aggregation reactions. A peptide-bound plastic plate is prepared, for example, by placing an adequate number of drops of the peptide in wells of the plastic plate. Peptide-bound microbeads are prepared, for example, by soaking microbeads in a peptide solution.

The peptide production method of the present invention is also applicable to prepare a substance including a plurality of the peptide sequence in its molecular structure. A linker may be used to link the plurality of the peptide to produce the substance including the plurality of the peptide. The linker works to join the plurality of the peptide sequence in a linear arrangement (see FIG. 6) or in a branched arrangement to form a high molecule. The number of the peptide sequence to be linked is not restricted but is preferably in a range of 4 to 8.

Figure 8:
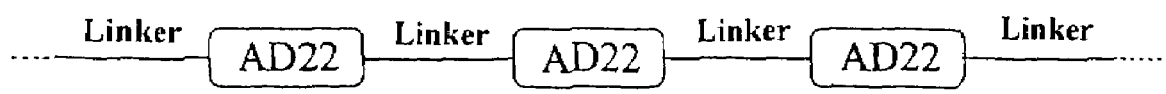
FIG. 8 shows the structure of a substance having multiple linkage of the peptide compound of the present invention, where AD22 represents a peptide of SEQ ID NO: 1 or a terminal-modified peptide with introduction of a compound for inducing a high-order structure into at least either of the amino terminal and the carboxyl terminal in the peptide of SEQ ID NO: 1, and the dotted line represents the repeated linear linkage of the peptides.

In FIG. 8, AD22 represents the peptide of SEQ ID NO: 1 or the terminal-modified peptide that is introduced with the compound for inducing the high-order structure at least either of the amino terminal and the carboxyl terminal in the peptide of SEQ ID NO: 1. The dotted line represents the repeated linear linkage of the peptides.

The linker may be one or a combination selected among amino acid sequences, sugar chain sequences, dicarboxlates, diamines, and metal complexes, that have covalent bond, ionic bond, and coordination bond, although these examples are not restrictive. The linker may be a peptide corresponding to Xaa in the peptide sequence of SEQ ID NO: 1 or the compound to be linked to Xaa for inducing the high-order structure.

Typical examples of the carrier molecule or polymer carrier are various natural proteins including tetanus toxoid, ovalbumin, serum albumin, and hemocyanin.

The peptide or the terminal-modified peptide produced by the method of the present invention or the compound including the plurality of the peptides linked to each other is formulated with a pharmaceutically acceptable carrier to produce a preventive medicine or a therapeutic medicine for *Plasmodium falciparum* infection or a diagnostic agent for *Plasmodium falciparum* infection. The terminology "pharmaceutically acceptable carrier" in the specification hereof includes, for example, immunostimulators, diluents, stabilizers, preservatives, and buffers.

The preventive medicine or the therapeutic medicine for *Plasmodium falciparum* infection may be, for example, a vaccine for preventing malaria infection or a treatment vaccine for stimulating the immune system of the malaria-infected patient against the antigen from *Plasmodium falciparum*. The diagnostic agent for *Plasmodium falciparum* infection may be a diagnostic agent for the presence of an antibody against the antigen from *Plasmodium falciparum*.

The method of the present invention may be adopted to produce an analog of the peptide of SEQ ID NO: 1. The terminology "analog of the peptide" means a peptide that is obtained by introducing substitution, deletion, or insertion of one or multiple amino acids in the peptide of SEQ ID NO: 1 and has a similar immunological response to that of the peptide of the present invention. The number of amino acids substituted, deleted, or inserted is not specifically restricted but is preferably in a range of 1 to 5 and more specifically in a range of 1 to 2.

The analog sequence may be used to enhance the solubility and the crystalline property in chemical syntheses or to enhance the solubility and the immunological response in immunological reactions, although these applications are not restrictive. The analog sequence may also be used for production of preventive, therapeutic, and diagnostic medicines.

The present invention is also directed to N-α-t-butoxycarbonyl-L-glutamic-γ-benzyl-α-trichloroethyl ester (Boc-Glu(OBzl)-OTce) that essentially consists of the L-form and is used for synthesis of the peptide of SEQ ID NO: 1. It is conventionally believed in the art that synthesis of the pure L-form Boc-Glu(OBzl)-OTce is practically impossible because of the potential racemization (Non-Patent Reference 2: pages 1962-1965, vol. 47, 1982, Journal of Organic Chemistry). The inventors of the present invention have managed to yield substantially pure L-form Boc-Glu(OBzl)-OTce by the DCC condensation reaction of N-α-t-butoxycarbonyl-L-glutamic-γ-benzyl ester and trichloroethyl alcohol in the presence of a catalyst DMAP as a reaction accelerator at a molar ratio of only 0.1 equivalent, which is significantly less than the conventional molar ratio of 0.5 equivalent. The L-form Boc-Glu(OBzl)-OTce is usable for syntheses of various glutamic acid-containing peptides, as well as the peptide of SEQ ID NO: 1. The terminology "essentially consisting of the L-form" means the L-form of not less than 95%, preferably not less than 98%, more preferably not less than 99%, or most preferably equal to 100%.

EXAMPLES

The present invention is described in detail with reference to some specific examples, although the present invention is not restricted to these examples.

FIG. 1 shows a synthesis procedure of a peptide H-Glu-Glu-Glu-Glu-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Gly-Gly-OH (SEQ ID NO: 13), and the details of the synthesis are explained below as Examples 1 through 10.

Figure 5:
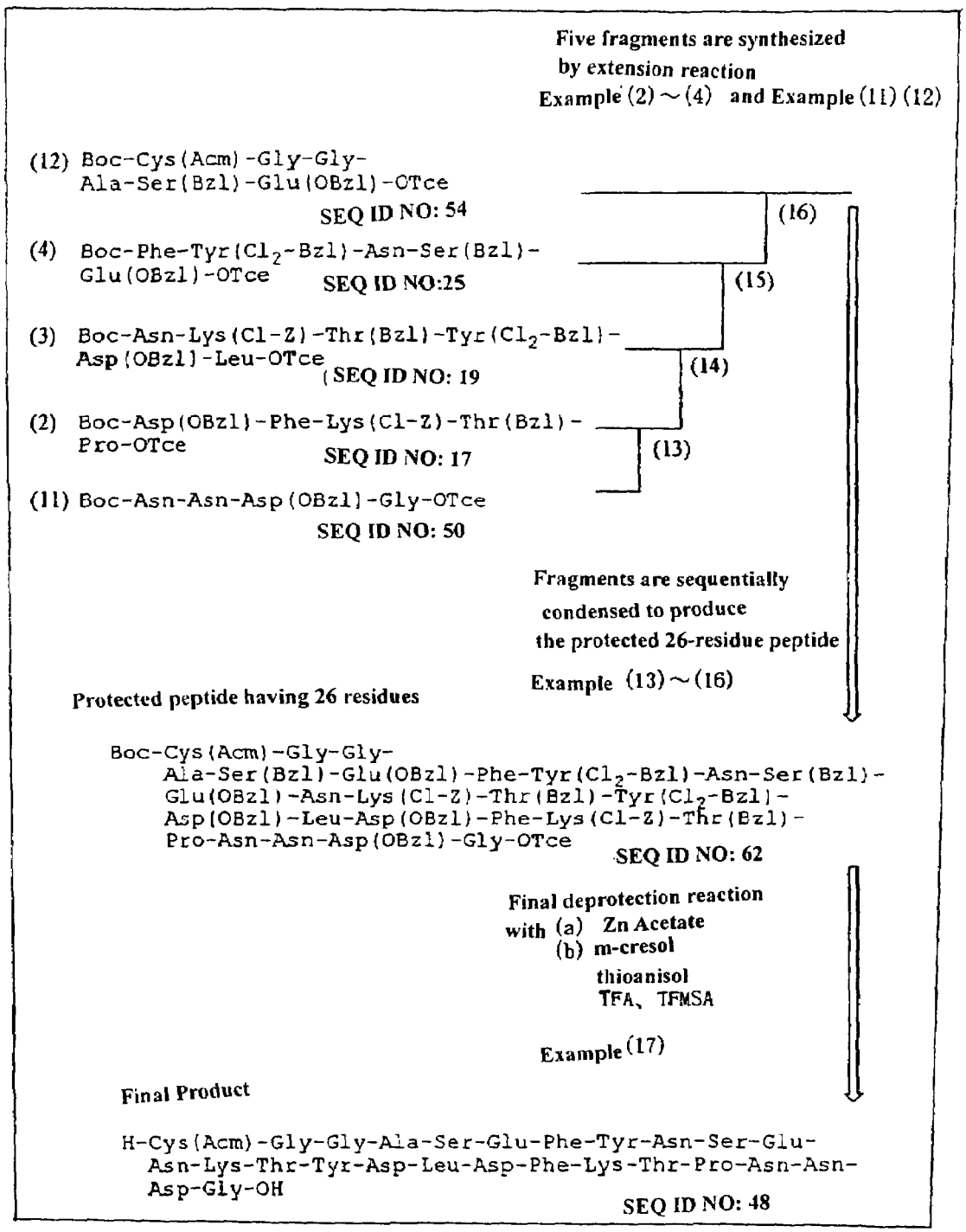
FIG. 5 is a flowchart showing a synthesis procedure of a peptide compound H-Cys(Acm)-Gly-Gly-Ala-Ser-Glu-Phe-Tyr-Asn-Ser-Glu-Asn-Lys-Thr-Tyr-Asp-Leu-Asp-Phe-L ys-Thr-Pro-Asn-Asn-Asp-Gly-OH (SEQ ID NO: 48) as another example of the present invention.

FIG. 5 shows a synthesis procedure of another peptide H-Cys-Gly-Gly-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Gly-Gly-OH (SEQ ID NO: 49), and the details of the synthesis are explained below as Examples 11 through 17.

These examples are only illustrative and not restrictive, and may be modified, changed, and altered in various ways, for example, by replacement of the protecting groups or the condensing agent with any other known groups or agent.

In the description below, some of the compounds used in the examples are abbreviated as:

(Amino Acid Derivatives)

p-Tos-OH.H-Gly-OBzl: glycine benzyl ester para-toluene-sulfonate

Boc-Gly-OH: N-α-(t-butoxycarbonyl)glycine

Boc-Ala-OH: N-α-(t-butoxycarbonyl)-L-alanine

Boc-Cys(Acm)-OH: N-α-(t-butoxycarbonyl)-S-acetamide-methyl-L-cysteine

Boc-Ser(Bzl)-OH: N-α-(t-butoxycarbonyl)-O-benzyl-L-serine

Boc-Thr(Bzl)-OH: N-α-(t-butoxycarbonyl)-O-benzyl-L-threonine

Boc-Phe-OH: N-x-(t-butoxycarbonyl)-L-phenylalanine

Boc-Tyr(Cl$_2$-Bzl)-OH: N-α-(t-butoxycarbonyl)-O-2,6-dichlorobenzyl-L-tyrosine

Boc-Asn-OH: N-α-(t-butoxycarbonyl)-L-asparagine

Boc-Asp(OBzl)-OH: N-α-(t-butoxycarbonyl)-L-aspartic-β-benzyl ester

Boc-Glu(OBzl)-OH: N-α-(t-butoxycarbonyl)-L-glutamic-γ-benzyl ester

Boc-Lys(Cl-Z)-OH: N-α-(t-butoxycarbonyl)-N-ε-2-chlorobenzyloxycarbonyl-L-lysine

HCl.H-Gly-OTce: glycine trichloroethyl ester hydrochloride

HCl.H-Leu-OTce: L-leucine trichloroethyl ester hydrochloride

HCl.H-Pro-OTce: L-proline trichloroethyl ester hydrochloride

HCl.H-Glu(OBzl)-OTce: L-glumatic-γ-benzyl ester-α-trichloroethyl ester hydrochloride (Protecting Groups for Amino Acid Main and Side Chains)
Acm: acetamide methyl ($CH_3CO-NH-CH_2-$)
Boc: tert-butoxycarbonyl (t-Bu-O—CO—)
OTce: trichloroethyl (—$CH_2$—$CCl_3$)
Bzl: benzyl (—$CH_2$—$C_6H_5$)
OBzl: benzoyl (—O—$CH_2$—$C_6H_5$)
$Cl_2$-Z: 2-chlorobenzyloxycarbonyl ($C_6H_4Cl$-$CH_2$—O—CO—)
$Cl_2$-Bzl: 2,6-dichlorobenzyl (—$CH_2$—$C_6H_3Cl_2$)

(Peptide Synthesis Agents)
DCC: N,N'-dicyclohexylcarbodiimide
HOBt: 1-hydroxybenzotriazole
HATU: O-(7-azabenzotriazol-1-yl)-1,1,3,3-tetramethyluronium hexafluorophosphate
DIEA: N,N-diisopropylethylamine
HBTU: 2-(1H-benzotriazol-1-yl)-1,1,3,3-tetramethyluronium hexafluorophosphate
TFA: trifluoroacetic acid
TFMSA: trifluoromethanesulfonic acid
$(Boc)_2O$: di-t-butyl carbonate
NMM: N-methylmorpholine
EDC.HCl: 1-ethyl-3-(3-dimethylaminopropyl)carbodiimide hydrochloride
DMAP: N,N-dimethylaminopyridine
p-Tos-OH: para-toluenesulfonic acid (Solvents)
THF: tetrahydrofuran
$CHCl_3$: chloroform
$CDCl_3$: deuterated chloroform
AcOEt: ethyl acetate
DMF: N,N-dimethylformamide
DMSO-$d_6$: deuterated dimethylsulfoxide
MeOH: methanol
$Et_2O$: diethyl ether Synthesis Step 1: Synthesis of BOC-L-Amino Acid An L-amino acid or a side chain-protected L-amino acid (1.0 mol) was dissolved in 4M aqueous NaOH solution (250 ml) and was gradually cooled down with ice cold-MeOH. $(Boc)_2O$ (240.0 g, 1.1 mol) dissolved in a minimum quantity of dioxane was added little by little to the cooled aqueous NaOH solution of L-amino acid over 30 minutes. The mixture was stirred in an ice bath for 1 hour and at room temperature for 1.5 hours. $NaHCO_3$ deposit was filtered off, and followed by extraction with EtOAc at pH3.0. The extracted EtOAc solution was washed with a 10% aqueous citric acid solution and was dried with $Na_2SO_4$. After filtration, the fitrate was subjected to vacuum concentration, and the residue was crystallized with hexane. Then, recrystallization was performed with AcOEt-hexane to yield Boc-L-amino acid.

Synthesis Step 2: Deprotection Reaction of Amino Terminal and Synthesis of Boc-Deprotected Compound A peptide compound with N-α-(t-butoxycarbonyl)-protected amino terminal in a 300 ml short neck flask was mixed with and dissolved in TFA (or 4M HCl solution of dioxane) inside the fume hood. The flask was immediately covered with a calcium chloride tube to prevent water incorporation. After confirmation of the termination of the reaction by TLC, the mixture was repeatedly concentrated with distilled $Et_2O$ until complete removal of TFA odor (or hydrochloric acid odor). This eventually yielded white powder of TFA salt (or hydrochloride salt). The yield was practically quantitative.

Example 1

Synthesis of
Boc-Asn-Asn-Asp(OBzl)-Gly-Gly-OBzl
(SEQ ID NO: 14)

1a: Synthesis of Boc-Gly-Gly-OBzl p-Tos-OH.H-Gly-OBzl (5.13 g, 15.2 mmol) was dissolved in distilled dichloromethane, and after addition of Boc-Gly-OH (2.93 g, 16.7 mmol) and DCC (3.45 g, 16.7 mmol), the mixture was stirred in an ice bath for 1 hour and at room temperature overnight. After filter-out of DCUrea, the filtrate was evaporated for condensation. The residue was dissolved in AcOEt, was sequentially washed with a 10% aqueous citric acid solution, water, a saturated aqueous $NaHCO_3$ solution, water, and saturated saline, and was dried with $Na_2SO_4$. After condensation, hexane was added to yield a crystalline product. The obtained crude crystals were recrystallized with AcOEt-hexane.

Yield: 4.56 g (93%)
$^1$H-NMR ($CDCl_3$, 300 MHz): 7.35 (5H, -Bzl); 6.58, 5.09 (2H, NH), 5.19 (2H, Bzl —$CH_2$—); 4.10, 3.84 (4H, αCH); 1.47 (9H, Boc t-Bu-)

1b: Synthesis of Boc-Asp(OBzl)-Gly-Gly-OBzl

HCl.H-Gly-Gly-OBzl (3.15 g, 12.17 mmol) was dissolved in distilled dichloromethane and was neutralized with NMM (1.339 ml, 12.17 mmol). After addition of Boc-Asp(OBzl)-OH (4.30 g, 13.3 mmol), DCC (2.74 g, 13.3 mmol), and HOBt (1.80 g, 13.3 mmol), the mixture was stirred.

After filter-out of DCUrea, the filtrate was evaporated for condensation. The residue was dissolved in AcOEt, was sequentially washed with a 10% aqueous citric acid solution, water, a saturated aqueous $NaHCO_3$ solution, water, and saturated saline, and was dried with $Na_2SO_4$. After condensation, the obtained oil-form product was dried with a vacuum pump.

Yield: 5.53 g (86%), $[\alpha]_D^{20}$=7.9° (c 0.1, MeOH)
$^1$H-NMR ($CDCl_3$, 300 MHz):7.26 (10H, Bzl); 7.06, 6.84, 5.52 (3H, NH); 5.16, 5.10 (4H, Bzl —$CH_2$—); 4.52, 4.09, 3.95 (5H, αCH); 3.13, 2.80 (2H, Glu —$CH_2$—); 1.44 (9H, Boc t-Bu)

1c: Synthesis of
Boc-Asn-Asp(OBzl)-Gly-Gly-OBzl)
(SEQ ID NO: 15)

HCl.H-Asp(OBzl)-Gly-Gly-OBzl (1.95 g, 4.20 mmol) was dissolved in DMF and was neutralized with NMM (462 μl, 4.20 mmol). After addition of Boc-Asn-OH (1.024 g, 4.41 mmol), HOBt (1.195 g, 8.82 mmol), and EDC.HCl (0.845 g, 4.41 mmol), the mixture was stirred. After condensation, the residue was dissolved in AcOEt, was sequentially washed with a 10% aqueous citric acid solution, water, a saturated aqueous $NaHCO_3$ solution, water, and saturated saline, and was dried with $Na_2SO_4$. After condensation, hexane was added to yield a precipitate.

Yield: 2.19 g (81%), $[\alpha]_D^{20}$=−16.9° (c 0.1, MeOH), melting point: 70 to 71° C.

Mass Spectrometry (ESI Method): m/e=704.4 ($[M+Na]^+$)

¹H-NMR (DMSO, 300 MHz):7.35 (10H, Bzl); 8.28, 8.20, 8.10, 7.35, 6.94 (6H, NH); 5.12, 5.07 (4H, Bzl —CH$_2$—); 4.67, 4.21 (2H, αCH); 3.91, 3.89 (4H, Gly αCH); 2.86, 2.67, 2.52, 2.43 (4H, βCH$_2$); 1.36 (9H, Boc t-Bu).

1d: Synthesis of
Boc-Asn-Asn-Asp(OBzl-Gly-Gly-OBzl
(SEQ ID NO: 14)

TFA.H-Asn-Asp(OBzl)-Gly-Gly-OBzl (SEQ ID NO: 16) (1.73 g, 2.64 mmol) was dissolved in DMF and was neutralized with DIEA (493 µl, 2.90 mmol). After addition of Boc-Asn-OH (0.67 g, 2.90 mmol), HOBt (0.71 g, 5.30 mmol), and HBTU (1.10 g, 2.90 mmol), the mixture was stirred in an ice bath for 1.5 hours. The resulting precipitate was dissolved in CHCl$_3$ and MeOH, followed by addition of Et$_2$O to yield a precipitate.

Yield: 1.28 g (64%), $[\alpha]_D^{20}$=−23.1° (c 0.1, MeOH), melting point: 172 to 175° C.

Mass Spectrometry (ESI Method): m/e=796.4 ([M+H]$^+$), 818.4 ([M+Na]$^+$)

¹H-NMR (DMSO-d$_6$, 500 MHz):7.37 (10H, Glu OBzl, —OBzl); 8.37, 8.13, 8.06, 7.44, 7.33, 6.99, 6.92 (9H, NH); 5.12, 5.08 (4H, Bzl —CH$_2$—); 4.65, 4.46, 4.24, 3.91 3.70 (5H, αCH); 2.89, 2.64, 2.56, 2.40 (4H, βCH$_2$); 1.36 (9H, Boc t-Bu).

Example 2

(2) Synthesis of Boc-Asp(OBzl)-Phe-Lys(Cl-Z)-Thr(Bzl)-Pro-OTce (SEQ ID NO: 17)

2a: Synthesis of Boc-Pro-OTce

Boc-Pro-OH (6.46 g, 30.0 mmol) in a 300 ml short neck flask was dissolved in distilled CHCl$_3$ (80 ml). DCC (6.82 g, 33.0 mmol) dissolved in advance in a minimum quantity of distilled CHCl$_3$ in ice bath with stirring was added thereto, and trichloroethanol (3.50 ml, 37.0 mmol) and DMAP (0.38 g, 3.0 mmol) was further added, and the mixture was stirred in an ice bath for 2 hours and at room temperature all day. After filter-out of DCUrea, the filtrate was subjected to vacuum concentration. The residue was dissolved in AcOEt, was sequentially washed with a 10% aqueous citric acid solution, water, a saturated aqueous NaHCO$_3$ solution, water, and saturated saline, and was dried with Na$_2$SO$_4$. The filtrate was subjected to vacuum concentration to yield an oil-form product.

Yield: 10.08 g (97%) (oil-form product)

¹H-NMR (CDCl$_3$, 300 MHz): 4.92, 4.76, 4.64 (2H, -OTce —CH$_2$—); 4.41 (1H, αCH); 3.51 (2H, Pro δCH$_2$); 2.28, 2.11 (2H, Pro βCH$_2$); 1.94 (2H, Pro γCH$_2$); 1.44 (9H, Boc t-Bu)

2b: Synthesis of Boc-Thr(Bzl)-Pro-OTce (Synthesis Step 1)
HCl.H-Pro-OTce (14.16 g, 50 mmol) in a 300 ml short neck flask was dissolved in distilled CHCl$_3$ (50 ml) and was neutralized with NMM (5.5 ml, 50 mmol). DCC (11.35 g, 55 mmol) dissolved in advance in a minimum quantity of distilled CHCl$_3$ was added thereto, and the mixture was stirred in an ice bath for 2 hours and at room temperature overnight. After completion of the reaction, DCUrea was filtered out, and the filtrate was subjected to vacuum concentration. The residue was added with AcOEt, was sequentially washed with a 10% aqueous citric acid solution, water, a saturated aqueous NaHCO$_3$ solution, water, and saturated saline, and was dried with Na$_2$SO$_4$. The filtrate was subjected to vacuum concentration to yield an oil. The oil was crystallized after being left for stand for some time.

Yield: 19.52 g (73%), $[\alpha]_D^{20}$=−49.4° (c 0.1, MeOH), melting point: 98 to 99° C.

(Synthesis Step 2)
HCl.H-Pro-OTce (4.29 g, 15.0 mmol) was dissolved in distilled dichloromethane and was neutralized with NMM (1.68 ml, 15.0 mmol). After addition of Boc-Thr(Bzl)-OH (3.08 g, 10.5 mmol) and DCC (2.48 g, 11.7 mmol), the mixture was stirred. After completion of the reaction, DCUrea was filtered out, and the filtrate was subjected to vacuum concentration. The residue was added with AcOEt, was sequentially washed with a 10% aqueous citric acid solution, water, a saturated aqueous NaHCO$_3$ solution, water, and saturated saline, and was dried with Na$_2$SO$_4$. Then, the filtrate was added with hexane to yield a crystal.

Yield: 4.20 g (74%), $[\alpha]_D^{20}$=−55.8° (c 0.1, MeOH), melting point: 102 to 103° C.

¹H-NMR (DMSO-d$_6$, 300 MHz): 7.30 (5H, Thr Bzl); 6.60 (1H, NH); 4.88 (2H, Bzl —CH$_2$—); 4.53 (2H, -OTce —CH$_2$—); 4.52, 4.35 (2H, αCH); 3.76 (3H, Pro δCH$_2$, Thr βCH); 2.28, 1.97 (2H, Pro βCH$_2$); 1.97 (2H, Pro γCH$_2$); 1.39 (9H, Boc t-Bu); 1.09 (3H, Thr γCH$_3$).

2c: Synthesis of Boc-Lys(Cl-Z)-Thr(Bzl)-Pro-OTce (Synthesis Step 1)
HCl.H-Thr(Bzl)-Pro-OTce (0.52 g, 1.1 mmol) in a 300 ml short neck flask was dissolved in distilled CHCl$_3$ (25 ml) and was neutralized with NMM (0.21 ml). After addition of Boc-Lys(Cl-Z)-OH (0.50 g, 1.2 mmol) and DCC (0.25 g, 1.2 mmol), the mixture was stirred in an ice bath for 2 hours and at room temperature overnight. After completion of the reaction, DCUrea was filtered out, and the filtrate was subjected to vacuum concentration. The residue was added with AcOEt, was sequentially washed with a 10% aqueous citric acid solution, water, a saturated aqueous NaHCO$_3$ solution, water, and saturated saline, and was dried with Na$_2$SO$_4$. The filtrate was subjected to vacuum concentration to yield an oil-form product. The obtained oil-form product (0.86 g) was purified by column chromatography with developing solvents of AcOEt: benzene=1:3 and AcOEt: benzene=1:1.

Yield: 0.53 g (58%) (oil-form product), $[\alpha]_D^{20}$=−42.6° (c 0.1, MeOH)

(Synthesis Step 2)
HCl.H-Thr(Bzl)-Pro-OTce (4.74 g, 10 mmol) was dissolved in DMF. After addition of Boc-Lys(Cl-Z)-OH (3.31 g, 10.5 mmol), HATU (4.00 g, 10.5 mmol), and DIEA (5.1 mL), the mixture was stirred for one hour. After condensation, the obtained oil-form product was purified by silica gel column chromatography with developing solvents of AcOEt: benzene=1:3 and AcOEt: benzene=1:1.

Yield: 7.2 g (86%) (oil-form product)

Mass Spectrometry (ESI Method): m/e=835.4 ([M+H]$^+$), 855.5 ([M+Na]$^+$)

¹H-NMR (DMSO-d$_6$, 300 MHz):7.82, 7.44, 7.36-7.27, 6.93 (12H, Thr Bzl, NH, Lys Cl-Z, Lys e-NH); 5.07 (2H, Bzl —CH$_2$—); 4.88 (2H, -OTce —CH$_2$—); 4.53 (2H, Cl-Z —CH$_2$—); 4.67, 4.48, 3.91, 3.78 (3H, αCH, Thr βCH); 3.78 (2H, Pro δCH$_2$); 2.94 (2H, Lys εCH$_2$), 2.26, 1.94 (2H, Pro βCH$_2$), 1.94 (2H, Pro γCH$_2$), 1.54 (2H, Lys βCH$_2$), 1.35 (9H, Boc t-Bu, Lys γCH$_2$, Lys δCH$_2$), 1.11 (3H, Thr γCH$_3$).

2d: Synthesis of Boc-Phe-Lys(Cl-Z)-Thr(Bzl)-Pro-OTce (SEQ ID NO: 18)

(Synthesis Step 1)

HCl.H-Lys(Cl-Z)-Thr(Bzl)-Pro-OTce (1.46 g, 1.9 mmol) in a 300 ml short neck flask was dissolved in DMF (20 ml) and was neutralized in ice bath with NMM (0.22 ml). After addition of Boc-Phe-OH (0.56 g, 2.1 mmol), HOBt (0.28 g, 2.1 mmol), and EDC.HCl (0.40 g, 2.1 mmol), the mixture was stirred in an ice bath for 2 hours and at room temperature overnight. After completion of the reaction, the mixture was subjected to vacuum concentration with a vacuum pump. The residue was added with AcOEt, was sequentially washed with a 10% aqueous citric acid solution, water, a saturated aqueous $NaHCO_3$ solution, water, and saturated saline, and was dried with $Na_2SO_4$. The filtrate was subjected to vacuum concentration to yield an oil-form product. The obtained oil-form product was dissolved in AcOEt, followed by addition of petroleum ether to yield white powder.

Yield: 1.45 g (78%), $[\alpha]_D^{20}=-39.2°$ (c 0.1, MeOH), melting point: 70 to 71° C.

(Synthesis Step 2)

HCl.H-Lys(Cl-Z)-Thr(Bzl)-Pro-OTce (2.28 g, 2.95 mmol) in a 300 ml short neck flask was dissolved in DMF and was neutralized in ice bath with NMM (0.22 ml). After addition of Boc-Phe-OH (0.88 g, 3.30 mmol), HOBt (0.44 g, 3.30 mmol), and EDC.HCl (0.69 g, 3.3 mmol), the mixture was stirred. After completion of the reaction, the mixture was subjected to vacuum concentration with a vacuum pump. The residue was added with AcOEt, was sequentially washed with a 10% aqueous citric acid solution, water, a saturated aqueous $NaHCO_3$ solution, water, and saturated saline, and was dried with $Na_2SO_4$. The filtrate was subjected to vacuum concentration to yield an oil-form product. The obtained oil-form product was dissolved in AcOEt, followed by addition of petroleum ether to yield white powder. The white powder was purified by silica gel column chromatography with developing solvents of AcOEt: benzene=1:3 and AcOEt: benzene=1:1.

Yield: 2.01 g (69%), $[\alpha]_D^{20}=-35.4°$ (c 0.1, MeOH), melting point: 69 to 71° C.

Mass Spectrometry (ESI Method): m/e=982.5 ([M+H]$^+$), 1004.4 ([M+Na]$^+$)

$^1$H-NMR (DMSO-$d_6$, 300 MHz):7.82, 7.44, 7.36-7.27, 6.93 (12H, Thr Bzl, NH, Lys Cl-Z, Lys εNH); 5.07 (2H, Bzl —$CH_2$—); 4.88 (2H, -OTce —$CH_2$—); 4.53 (2H, Cl-Z —$CH_2$—); 4.67, 4.48, 3.91, 3.78 (4H, αCH, Thr βCH); 3.78 (2H, Pro δ$CH_2$); 2.94 (2H, Lys ε$CH_2$); 2.26, 1.94 (2H, Pro β$CH_2$); 1.94 (2H, Pro γ$CH_2$); 1.54 (2H, Lys β$CH_2$); 1.35 (13H, Boc t-Bu, Lys γ$CH_2$, Lys δ$CH_2$); 1.11 (3H, Thr γ$CH_3$).

2e: Synthesis of Boc-Asp(OBzl)-Phe-Lys(Cl-Z)-Thr(Bzl)-Pro-OTce (SEQ ID NO: 17)

(Synthesis Step 1)

HCl.H-Phe-Lys(Cl-Z)-Thr(Bzl)-Pro-OTce (SEQ ID NO: 19) (0.50 g, 0.55 mmol) in a 300 ml short neck flask was dissolved in distilled $CHCl_3$ (10 ml) and was neutralized in ice bath with NMM (60 µl). After addition of Boc-Asp (OBzl)-OH (0.20 g, 0.61 mmol) and HOBt (0.082 g, 0.61 mmol) and subsequent addition of DCC (0.13 g, 0.61 mmol) dissolved in advance in $CHCl_3$ (10 ml), the mixture was stirred in an ice bath for 2 hours and at room temperature overnight. After completion of the reaction, DCUrea was filtered out, and the filtrate was subjected to vacuum concentration. The residue was added with AcOEt, was sequentially washed with a 10% aqueous citric acid solution, water, a saturated aqueous $NaHCO_3$ solution, water, and saturated saline, and was dried with $Na_2SO_4$. The filtrate was subjected to vacuum concentration to yield an oil-form product. The obtained oil-form product was dissolved in $CHCl_3$, followed by addition of petroleum ether to yield a white precipitate.

Yield: 0.55 g (85%), $[\alpha]_D^{20}=-46.5°$ (c 0.1, MeOH), melting point: 108 to 110° C.

(Synthesis Step 2)

HCl.H-Phe-Lys(Cl-Z)-Thr(Bzl)-Pro-OTce (1.76 g, 1.92 mmol) in a 300 ml short neck flask was dissolved in distilled $CHCl_3$ and was neutralized in ice bath with NMM (211 ml). After addition of Boc-D(OBzl)-OH (0.68 g, 2.11 mmol), HOBt (0.29 g, 2.11 mmol), and DCC (0.44 g, 2.11 mmol), the mixture was stirred. After completion of the reaction, DCUrea was filtered out, and the filtrate was subjected to vacuum concentration. The residue was added with AcOEt, was sequentially washed with a 10% aqueous citric acid solution, water, a saturated aqueous $NaHCO_3$ solution, water, and saturated saline, and was dried with $Na_2SO_4$. The filtrate was subjected to vacuum concentration to yield an oil. The obtained oil was dissolved in AcOEt, followed by addition of hexane to yield a white precipitate.

Yield: 1.71 g (78%), $[\alpha]_D^{20}=-40.1°$ (c 0.1, MeOH), melting point: 108 to 109° C.

Mass Spectrometry (ESI Method): m/e=1185.3 ([M+H]$^+$), 1207.5 ([M+Na]$^+$)

$^1$H-NMR (DMSO-$d_6$, 300 MHz): 8.05, 8.12, 7.82, 7.44, 7.36-7.27, 7.19 (10H, Bzl; 4H, Cl-Z; 4H, NH; 1H, Lys εNH), 5.07 (4H, Bzl —$CH_2$—); 4.88 (2H, -OTce —$CH_2$—); 4.53 (2H, Cl-Z —$CH_2$—); 4.67, 4.48, 4.35, 3.83, 3.72 (4H, αCH, Thr βCH); 3.78 (2H, Pro δ$CH_2$); 2.94, 2.70, 2.55 (2H, Lys ε$CH_2$; 2H, Asp β$CH_2$); 2.26, 1.94 (2H, Pro β$CH_2$); 1.94 (2H, Pro γ$CH_2$); 1.54 (2H, Lys β$CH_2$); 1.35 (9H, Boc t-Bu; 2H, Lys γ$CH_2$; 2H, Lys δ$CH_2$); 1.11 (3H, Thr γ$CH_3$).

Example 3

(3) Synthesis of Boc-Asn-Lys(Cl-Z)-Thr(Bzl)-Tyr(Cl$_2$-Bzl)-Asp(OBzl)-Leu-OTce (SEQ ID NO: 20)

3a: Synthesis of Boc-Asp(OBzl)-Leu-OTce

HCl.H-Leu-OTce (2.99 g, 10 mmol) in a short neck flask was dissolved in distilled $CHCl_3$ (60 ml) and was neutralized in ice bath with NMM (1.10 ml). After addition of Boc-Asp (OBzl)-OH (2.46 g, 11 mmol) and DCC (2.27 g, 11 mmol), the mixture was stirred in an ice bath for 1.5 hours and at room temperature overnight. After completion of the reaction, DCUrea was filtered out, and the filtrate was subjected to vacuum concentration. The residue was added with AcOEt, was sequentially washed with a 10% aqueous citric acid solution, water, a saturated aqueous $NaHCO_3$ solution, water, and saturated saline, and was dried with $Na_2SO_4$. The filtrate was concentrated to yield an oil-form product.

The obtained oil-form product (5.65 g, 9.95 mmol) was purified by column chromatography with developing solvents of AcOEt: benzene=1:7 and AcOEt: benzene=1:5. Subsequent condensation yielded a transparent oil-form product.

Yield: 4.45 g (78%), $[\alpha]_D^{20}$, 46.5° (c 0.1, MeOH), melting point: 70 to 71° C.

$^1$H-NMR (CDCl$_3$, 300 MHz): 7.35 (5H, Bzl); 5.18, 5.14, 4.64, 4.60 (2H, -OTce —$CH_2$—); 6.96, 5.71 (2H, NH); 5.14 (2H, Bzl —$CH_2$—); 4.70, 4.55 (3H, αCH); 3.07, 2.77 (2H,

Asp βCH$_2$); 1.64 (2H, Leu βCH$_2$; 1H, Leu γCH); 1.44 (9H, Boc t-Bu); 0.95 (6H, Leu δCH$_2$).

3b: Synthesis of Boc-Tyr(Cl$_2$-Bzl)-Asp(OBzl)-Leu-OTce

HCl.H-Asp(OBzl)-Leu-OTce (2.05 g, 4.07 mmol) in a short neck flask was dissolved in distilled CHCl$_3$ (10 ml) and was neutralized in ice bath with NMM (0.45 ml). After addition of Boc-Tyr(Cl$_2$-Bzl)-OH (1.52 g, 4.47 mmol), HOBt (0.61 g, 4.52 mmol), and EDC.HCl (0.86 g, 4.49 mmol), the mixture was stirred in an ice bath for 1 hour and at room temperature overnight. After completion of the reaction, the reaction solution was concentrated. The residue was dissolved in DMF and was subjected to vacuum concentration. Addition of ion exchange water to the residue caused a precipitation. After filtration, the precipitate was placed on a glass filter, was sequentially washed with a 10% aqueous citric acid solution, water, a saturated aqueous NaHCO$_3$ solution, water, and saturated saline, and was dried in a desiccator. This yielded white powder.

Yield: 3.06 g (85%), [α]$_D^{20}$=−46.5° (c 0.1, MeOH), melting point: 101 to 104° C.

$^1$H-NMR (CDCl$_3$, 300 MHz): 7.37, 7.33, 7.14, 6.98, 6.95 (5H, Bzl; 3H, Cl$_2$-Bzl; 4H, Tyr C$_6$H$_5$—; 3H, NH); 4.87, 4.83, 4.64, 4.60 (2H, -OTce —CH$_2$—); 5.12, 5.24 (2H, Bzl —CH$_2$—; 2H, Cl$_2$-Bzl —CH$_2$—); 4.80, 4.62, 4.30 (3H, αCH); 3.05, 3.02, 2.65 (2H, Asp βCH$_2$; 1H, Tyr βCH$_2$); 1.71, 1.58 (2H, Leu βCH$_2$; 1H, Leu γCH); 1.41 (9H, Boc t-Bu); 0.94 (6H, Leu δCH$_2$).

3c: Synthesis of Boc-Thr(Bzl)-Tyr(Cl$_2$-Bzl)-Asp(OBzl)-Leu-OTce (SEQ ID NO: 21)

HCl.H-Tyr(Cl$_2$-Bzl)-Asp(OBzl)-Leu-OTce (2.48 g, 3.0 mmol) in a short neck flask was dissolved in DMF (30 ml) and was neutralized with NMM (330 μl). After addition of Boc-Thr(Bzl)-OH (1.02 g, 3.3 mmol), HOBt (0.45 g, 3.3 mmol), and EDC.HCl (0.63 g, 3.3 mmol), the mixture was stirred in an ice bath for 3 hours and at room temperature for 4 hours. After completion of the reaction, the reaction solution was concentrated. Addition of ion exchange water to the residue caused a precipitation. After filtration, the precipitate was placed on a glass filter, was sequentially washed with a 10% aqueous citric acid solution, water, a saturated aqueous NaHCO$_3$ solution, water, and saturated saline, and was dried in a desiccator. This yielded white powder. The obtained white powder was recrystallized with CHCl$_3$-hexane to yield a white crystalline product.

Yield: 2.45 g (76%), [α]$_D^{20}$=−46.5° (c 0.1, MeOH), melting point: 149 to 151° C.

$^1$H-NMR (CDCl$_3$, 300 MHz): 7.36, 7.34, 7.32, 7.11, 6.99, 6.97, 6.87, 6.84 (10H, Bzl; 3H, Cl$_2$-Bzl; 4H, Y-Ph; 3H, NH); 5.35 (1H, NH); 4.87, 4.83, 4.65, 4.61 (2H, -OTce —CH$_2$—); 5.18, 5.11 (4H, Bzl —CH$_2$—; 2H, Cl$_2$-Bzl —CH$_2$—); 4.87, 4.83, 4.65, 4.43, 4.08 (4H, αCH; 2H, Bzl —CH$_2$—; 1H, Thr βCH); 3.05, 3.02, 2.65 (2H, Asp βCH$_2$; 1H, Tyr βCH$_2$); 1.71, 1.58 (2H, Leu βCH$_2$; 1H, Leu γCH); 1.41 (9H, Boc t-Bu); 1.18 (3H, Thr γCH$_3$); 0.94 (6H, Leu δCH$_2$).

3d: Synthesis of Boc-Lys(Cl-Z)-Thr(Bzl)-Tyr(Cl$_2$-Bzl)-Asp(OBzl)-Leu-OTce (SEQ ID NO: 22)

HCl.H-Thr(Bzl)-Tyr(Cl$_2$-Bzl)-Asp(OBzl)-Leu-OTce (SEQ ID NO: 23) (2.14 g, 2.10 mmol) in a short neck flask was dissolved in DMF (40 ml) and was neutralized with NMM (230 μl). After addition of Boc-Lys(Cl-Z)-OH (0.95 g, 2.3 mmol), HOBt (0.31 g, 2.3 mmol), and EDC.HCl (0.44 g, 2.3 mmol), the mixture was stirred in an ice bath for 3 hours and at room temperature for 4 hours. After completion of the reaction, the reaction solution was concentrated. Addition of ion exchange water to the residue caused a precipitation. After filtration, the precipitate was placed on a glass filter, was sequentially washed with a 10% aqueous citric acid solution, water, a saturated aqueous NaHCO$_3$ solution, water, and saturated saline, and was dried in a desiccator. This yielded white powder. The obtained white powder was purified by column chromatography (with a developing solvent of CHCl$_3$: MeOH=98:2).

Yield: 2.56 g (89%), [α]$_D^{20}$=−46.5° (c 0.1, MeOH), melting point: 149 to 151° C.

$^1$H-NMR (CDCl$_3$, 300 MHz): 7.36, 7.34, 7.32, 7.11, 6.99, 6.97, 6.87, 6.84 (10H, Bzl; 4H, Cl-Z; 3H, Cl$_2$-Bzl; 4H, Tyr C$_6$H$_5$; 4H, NH; 1H, Lys εNH); 5.35 (1H, NH); 4.87, 4.83, 4.65, 4.61 (2H, -OTce —CH$_2$—); 5.18, 5.11, 4.60 (4H, Bzl —CH$_2$—; 2H, Cl$_2$-Bzl —CH$_2$—; 2H, Cl-Z —CH$_2$—); 4.87, 4.83, 4.65, 4.43; 4.08 (5H, αCH, 2H, Bzl —CH$_2$—; 1H, Thr βCH); 3.45, 3.05, 3.02, 2.94, 2.65 (2H, Asp βCH$_2$; 2H, Tyr βCH$_2$; 2H, Lys εCH$_2$); 1.71, 1.69, 1.58 (2H, Leu βCH$_2$; 1H, Leu γCH; Lys βCH$_2$; Lys γCH$_2$); 1.41 (9H, Boc t-Bu); 1.18 (3H, Thr γCH$_3$); 0.94 (6H, Leu δCH$_2$).

3e: Synthesis of Boc-Asn-Lys(Cl-Z)-Thr(Bzl)-Tyr(Cl$_2$-Bzl)-Asp(OBzl)-Leu-OTce (SEQ ID NO: 20)

HCl.H-Lys(Cl-Z)-Thr(Bzl)-Tyr(Cl$_2$-Bzl)-Asp(OBzl)-Leu-OTce (SEQ ID NO: 24) (2.30 g, 1.75 mmol) in a short neck flask was dissolved in DMF (20 ml) and was neutralized with NMM (193 μl). After addition of Boc-Asn-OH (0.45 g, 1.93 mmol), HOBt (0.52 g, 3.85 mmol), and EDC.HCl (0.37 g, 1.93 mmol), the mixture was stirred in an ice bath for 3 hours and at room temperature for 4 hours. After completion of the reaction, the reaction solution was concentrated, followed by addition of ion exchange water to the residue to cause a precipitation. After filtration, the precipitate was placed on a glass filter, was sequentially washed with a 10% aqueous citric acid solution, water, a saturated aqueous NaHCO$_3$ solution, water, and saturated saline, and was dried in a desiccator. This yielded white powder.

Yield: 2.45 g (94%), [α]$_D^{20}$=−46.5° (c 0.1, MeOH), melting point: 207 to 209° C.

$^1$H-NMR (DMSO-d$_6$, 300 MHz): 8.35, 7.36, 7.34, 7.32, 7.11, 6.99, 6.97, 6.87, 6.84 (10H, Bzl; 4H, Cl-Z; 3H, Cl$_2$-Bzl; 4H, Tyr C$_6$H$_5$; 6H, NH; 1H, Lys εNH; 2H, Asn γNH$_2$); 4.87, 4.83, 4.65, 4.61 (2H, -OTce —CH$_2$—); 5.18, 5.11, 4.60 (4H, Bzl —CH$_2$—; 2H, Cl$_2$-Bzl —CH$_2$—; 2H, Cl-Z —CH$_2$—); 4.87, 4.83, 4.71, 4.55, 4.43, 4.30, 4.23 (6H, αCH; 2H, Bzl —CH$_2$—; 1H, Thr βCH); 3.15, 3.05, 3.02, 2.94, 2.65 (2H, Asp βCH$_2$; 2H, Tyr βCH$_2$; 2H, Lys εCH$_2$; 2H, Asn βCH$_2$); 1.71, 1.69, 1.58 (2H, Leu βCH$_2$; 1H, Leu γCH; 2H Lys βCH$_2$; 2H Lys γCH$_2$); 1.41 (9H, Boc t-Bu); 1.18 (3H, Thr γCH$_3$); 0.94 (6H, Leu δCH$_2$).

Example 4

(4) Synthesis of Boc-Phe-Tyr(Cl$_2$-Bzl)-Asn-Ser(Bzl)-Glu(OBzl)-OTce (SEQ ID NO: 25)

4a: Synthesis of Boc-Asn-Ser(Bzl)-Glu(OBzl)-OTce (Synthesis Step 1)

HCl.H-Ser(Bzl)-Glu(OBzl)-OTce (8.45 mmol) in a 100 ml short neck flask was dissolved in distilled CHCl$_3$ (10 ml) and was neutralized with NMM (0.930 ml, 8.45 mmol). Boc-Asn-OH (2.16 g, 9.30 mmol) dissolved in DMF (10 ml) and HOBt (2.51 g, 18.6 mmol) were added to the reaction solution. Subsequently DCC (1.92 g, 9.30 mmol) dissolved in $CHCl_3$ (20 ml) was added little by little to the reaction solution. After completion of the reaction, condensation and filtration were repeated until complete removal of DCU. The residue was dissolved in AcOEt, was sequentially washed with a 10% aqueous citric acid solution, water, a saturated aqueous $NaHCO_3$ solution, water, and saturated saline, and was dried with anhydrous $Na_2SO_4$. After filtration, it was subjected to vacuum concentration, and was mixed with $CHCl_3$-petroleum ether to yield a white precipitate. The precipitate was purified by gel filtration column chromatography (Sephadex LH20, MeOH).

Yield: 4.62 g (72%), $[\alpha]_D^{20}$=−24.2° (c 0.1, MeOH), melting point: 64 to 66° C.

(Synthesis Step 2)

HCl.H-Ser(Bzl)-Glu(OBzl)-OTce (10 mmol) in a 300 ml short neck flask was dissolved in DMF (40 ml), was neutralized with NMM (1.1 ml, 10 mmol), and was mixed with Boc-Asn-OH (2.55 g, 11 mmol), HOBt (2.97 g, 22 mmol), and EDC.HCl (2.11 g, 11 mmol). After completion of the reaction, the residue was dissolved in AcOEt, was sequentially washed with a 10% aqueous citric acid solution, water, a saturated aqueous $NaHCO_3$ solution, water, and saturated saline, and was dried with anhydrous $Na_2SO_4$. After filtration, it was subjected to vacuum concentration, and was mixed with AcOEt-$Et_2O$ to yield a white precipitate.

Yield: 5.48 g (72%), $[\alpha]_D^{20}$=−22.2° (c 0.1, MeOH), melting point: 64 to 66° C.

Mass Spectrometry (ESI Method): m/e=781.2 ([M+Na]$^+$)

$^1$H-NMR ($CDCl_3$, 300 MHz):7.52, 7.36, 5.88, 5.54 (5H, NH, Asn γ$NH_2$); 7.36, 7.24 (10H, Glu OBzl, Ser Bzl); 5.08 (2H, Glu OBzl —$CH_2$—); 4.60 (2H, -OTce —$CH_2$—); 4.52 (2H, Ser -Bzl —$CH_2$—); 4.68, 4.56, 4.42 (3H, αCH); 4.00, 3.60 (2H, Ser β$CH_2$); 2.84, 2.68 (2H, Asn β$CH_2$); 2.50 (2H, Glu β$CH_2$); 2.32, 2.10 (2H, Glu γ$CH_2$); 1.38 (9H, Boc t-Bu).

4b: Synthesis of Boc-Tyr($Cl_2$-Bzl)-Asn-Ser(Bzl)-Glu(OBzl)-OTce (SEQ ID NO: 26)

(Synthesis Step 1)

HCl.H-Asn-Ser(Bzl)-Glu(OBzl)-OTce (0.766 g, 1.10 mmol) in a 100 ml short neck flask was dissolved in DMF (20 ml) and was neutralized with NMM (0.120 ml, 1.10 mmol). After addition of Boc-Tyr($Cl_2$-Bzl)-OH (0.528 g, 1.21 mmol) and HOBt (0.327 g, 2.42 mmol), EDC.HCl (0.230 g, 1.21 mmol) was added to the mixture in ice bath with stirring. After completion of the reaction, the reaction mixture was concentrated and dissolved in AcOEt. Then, it was sequentially washed with a 10% aqueous citric acid solution, water, a saturated aqueous $NaHCO_3$ solution, water, and saturated saline, and was dried with anhydrous $Na_2SO_4$. After filtration, it was subjected to vacuum concentration, and was mixed with $CHCl_3$-petroleum ether to yield a white precipitate. A spot expected to be Boc-Tyr($Cl_2$-Bzl)-OH was detected by TLC, followed by purification by column chromatography (with a developing solvent of $CHCl_3$: MeOH=93:7). $CHCl_3$-petroleum ether was added for crystallization to yield a white crystal.

Yield: 0.87 g (73%), $[\alpha]_D^{20}$=−18.4° (c 0.1, MeOH), melting point: 150 to 152° C.

(Synthesis Step 2)

HCl.H-Asn-Ser(Bzl)-Glu(OBzl)-OTce (4.18 g, 6.0 mmol) in a 300 ml short neck flask was dissolved in DMF (40 ml) and was neutralized with NMM (0.66 ml, 6.0 mmol). After addition of Boc-Tyr($Cl_2$-Bzl)-OH (2.77 g, 6.3 mmol) and HOBt.$H_2O$ (0.96 g, 6.3 mmol), EDC.HCl (1.21 g, 6.3 mmol) was added to the mixture in ice bath with stirring. After completion of the reaction, the reaction mixture was concentrated and was mixed with water to cause a precipitation. The precipitate was filtered and was recrystallized with THF-$Et_2O$ to yield a white crystalline product.

Yield: 5.35 g (82%), $[\alpha]_D^{20}$−1-18.4° (c 0.1, MeOH), melting point: 150 to 152° C.

$^1$H-NMR ($CDCl_3$, 300 MHz):7.68, 7.54, 7.43, 7.37, 5.92, 5.34 (6H, NH, Asn γ$NH_2$); 7.34, 7.30, 7.26 (13H, Tyr $Cl_2$-Bzl, Glu OBzl, Ser Bzl); 7.12, 6.94 (4H, Tyr $C_6H_5$); 5.22 (2H, Tyr $Cl_2$-Bzl —$CH_2$—); 5.07 (2H, Glu OBzl —$CH_2$—); 4.85, 4.64 (2H, -OTce —$CH_2$—); 4.46 (2H, Ser Bzl —$CH_2$—); 5.01, 4.66, 4.48, 4.20 (4H, αCH); 3.96, 3.78 (2H, Ser β$CH_2$); 3.07, 2.83 (Tyr β$CH_2$); 2.75, 2.58 (2H, Asn β$CH_2$); 2.52 (2H, Glu β$CH_2$); 2.33, 2.17 (2H, Glu γ$CH_2$); 1.37 (9H, Boc t-Bu-).

4c: Synthesis of Boc-Phe-Tyr($Cl_2$-Bzl)-Asn-Ser(Bzl)-Glu(OBzl)-OTce (SEQ ID NO: 25)

(Synthesis Step 1)

HCl.H-Tyr($Cl_2$-Bzl)-Asn-Ser(Bzl)-Glu(OBzl)-OTce (SEQ ID NO: 27) (1.83 g, 1.80 mmol) in a 100 ml short neck flask was dissolved in DMF (50 ml) and was neutralized with NMM (200 μl, 1.80 mmol). After addition of Boc-Phe-OH (0.525 g, 1.98 mmol) and HOBt (0.535 g, 3.96 mmol), EDC.HCl (0.380 g, 1.98 mmol) was added to the mixture in ice bath with stirring. After completion of the reaction, the reaction mixture was concentrated and was mixed with water to cause a precipitation. The precipitate was filtered, placed on a glass filter, and was sequentially washed with a 10% aqueous citric acid solution, water, a saturated aqueous $NaHCO_3$ solution, water, and saturated saline. The precipitate was recrystallized with THF-$Et_2O$ to yield a white crystalline product.

Yield: 2.11 g (95%), $[\alpha]_D^{20}$=16.7° (c 0.1, DMF), melting point: 202 to 204° C.

(Synthesis Step 2)

HCl.H-Tyr($Cl_2$-Bzl)-Asn-Ser(Bzl)-Glu(OBzl)-OTce (3.87 g, 3.8 mmol) in a 300 ml short neck flask was dissolved in DMF (50 ml) and was neutralized with NMM (418 ml, 3.8 mmol). After addition of Boc-Phe-OH (1.11 g, 4.18 mmol) and HOBt.$H_2O$ (0.64 g, 4.18 mmol), EDC.HCl (0.80 g, 4.18 mmol) was added to the mixture in ice bath with stirring. After completion of the reaction, the reaction mixture was mixed with water to cause a precipitation. The precipitate was filtered, placed on a glass filter, and was sequentially washed with a 10% aqueous citric acid solution, water, a saturated aqueous $NaHCO_3$ solution, water, and saturated saline. The precipitate was dissolved in a solvent mixture of $CHCl_3$:TFE (3:1) and was recrystallized by gradual addition of MeOH to yield a white crystalline product.

Yield: 4.24 g (91%), $[\alpha]_D^{20}$=−16.7° (c 0.1, DMF), melting point: 202 to 204° C.

Mass Spectrometry (ESI Method): m/e=1251.1 ([M+Na]$^+$), 1267.4 ([M+K]$^+$)

$^1$H-NMR (DMSO-$d_6$, 300 MHz):8.52, 8.41, 8.20, 7.89, 6.87 (7H, NH, Asn γ$NH_2$); 7.52, 7.43, 7.33-7.16, 6.90 (22H, Phe $C_6H_5$—, Tyr —$C_6H_4$—, Tyr —$Cl_2$-Bzl, Glu —OBzl, Ser -Bzl); 5.13, (2H, Tyr —$Cl_2$-Bzl —$CH_2$—); 5.06 (2H, Glu —OBzl —$CH_2$—); 4.90, 4.79 (2H, -OTce —$CH_2$—); 4.46

(2H, Ser -Bzl —CH$_2$—); 4.65, 4.52, 4.41, 4.10 (5H, oαCH); 3.65 (2H, Ser βCH$_2$); 2.96, 2.87 (Phe βCH$_2$); 2.74, 2.66 (Tyr βCH$_2$); 2.51, 2.48 (2H, Asn βCH$_2$); 2.41 (2H, Glu βCH$_2$); 2.10, 2.00 (2H, Glu γCH$_2$); 1.26 (9H, Boc t-Bu).

Example 5

(5) Synthesis of Boc-[Glu(OBzl)]$_4$-Ala-Ser(Bzl)-Glu(OBzl)-OTce (SEQ ID NO: 28)

5a: Synthesis of Boc-Glu(OBzl)-OTce

Figure 2:
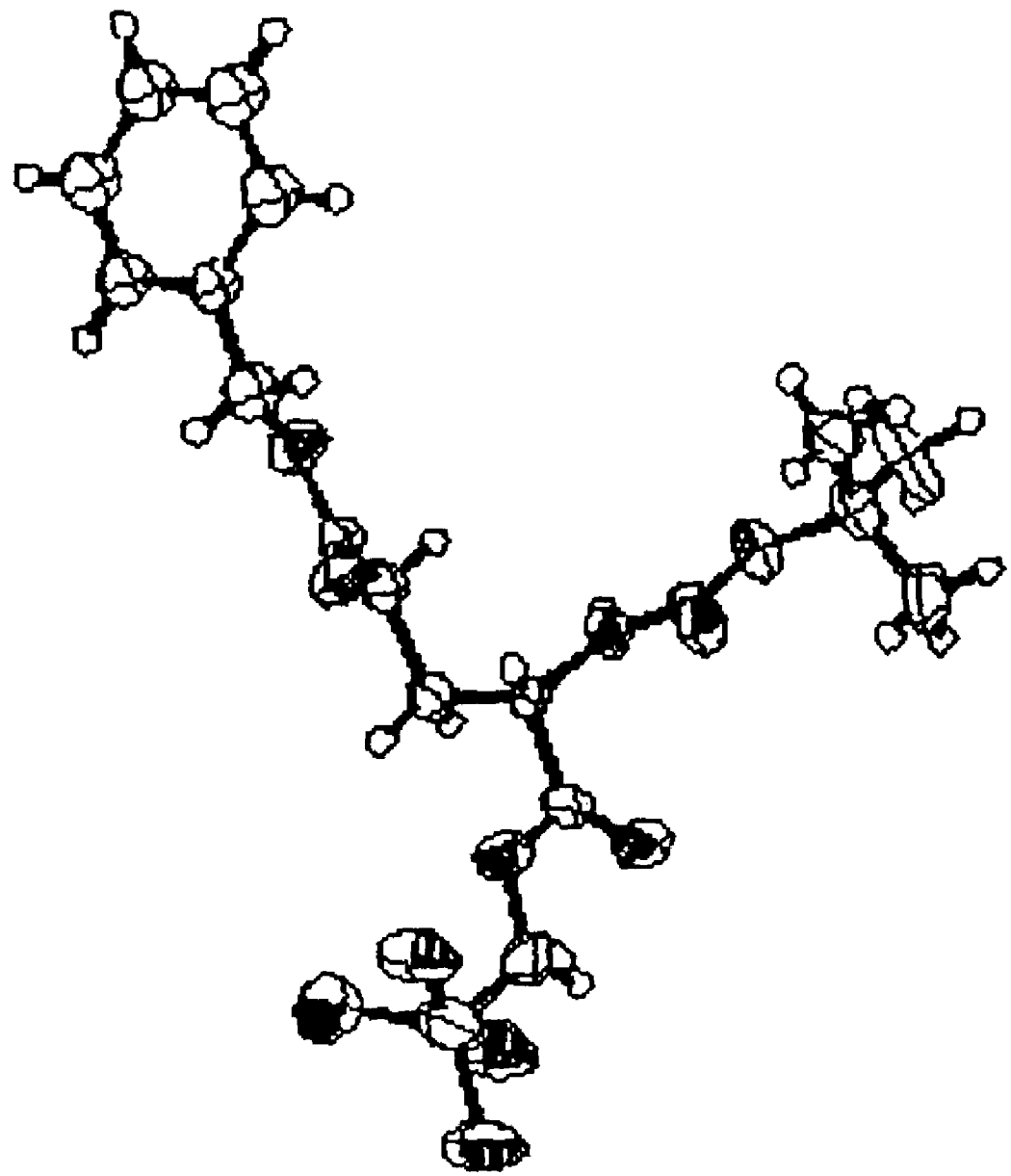
FIG. 2 shows the crystal structure of a synthesis intermediate N-α-t-butoxycarbonyl-L-glutamic-γ-benzyl ester-α-trichloroethyl ester obtained by X-ray diffraction analysis of reflection data with CuKα line, with regard to the peptide compound H-Glu-Glu-Glu-Glu-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Gly-Gly-OH (SEQ ID NO: 13) as one example of the present invention.

Boc-Glu(OBzl)-OH (33.8 g, 100 mmol) in a 500 ml short neck flask was dissolved in distilled CHCl$_3$ (150 ml) and was mixed with trichloroethyl alcohol (10.6 ml, 110 mmol). DCC (22.7 g, 110 mmol) was separately dissolved in distilled CHCl$_3$ (100 ml). The DCC solution was added with a Pasteur pipette to the 500 ml short neck flask in ice bath with stirring. A trace amount of DMAP (1.22 g, 10 mmol) as a catalyst for accelerating esterification was also added to the reaction solution. The progress of the reaction was monitored by thin layer chromatography. The reaction of this scale is completed within a time period of 1 through 3 hours. The close examination of the DMAP load proved that the conventionally used quantity of 0.5 equivalent (see Non-Patent Reference 2) accelerated racemization of the product. The examination result showed that addition of 0.1 equivalent of DMAP was adequate for the reaction. After completion of the reaction, condensation and filtration were repeated until complete removal of DCU. The residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After filtration, it was subjected to vacuum concentration to yield crude crystals. Recrystallization with AcOEt-hexane yielded clear colorless prism crystals. Prevention of the racemization and production of the substantially pure L-amino acid, which had been impossible by the conventional technique, were confirmed by X-ray single-crystal structure analysis and by measurement of the degree of rotation. The crystal structure is shown in FIG. 2. The degree of rotation is shown below as $[\alpha]_D^{20}$.

Yield: 39.4 g (84%), $[\alpha]_D^{20}$=−27.8° (c 0.1, MeOH), melting point: 94 to 96° C.

$^1$H-NMR (CDCl$_3$, 300 MHz):7.36 (5H, Glu —OBzl); 5.13 (3H, NH, -Bzl —CH$_2$—); 4.89, 4.66 (2H, —OTce —CH$_2$—); 4.46 (1H, αCH); 2.52 (2H, Glu βCH$_2$); 2.29, 2.07 (2H, Glu γCH$_2$); 1.42 (9H, Boc t-Bu-). Crystallographic Data: a=9.995 (2) Å, c=12.970(4) Å, V=1122.0(4) Å$^3$Å, Space Group P3$_1$ (#144)

5b: Synthesis of Boc-Ser(Bzl)-Glu(OBzl)-OTce

HCl.H-Glu(OBzl)-OTce (4.05 g, 10.0 mmol) in a 300 ml short neck flask was dissolved in distilled CHCl$_3$ (100 ml), was neutralized with NMM (1.10 ml, 10.0 mmol), and was mixed with Boc-Ser(Bzl)-OH (3.25 g, 11.0 mmol). DCC (2.27 g, 11.0 mmol) was separately dissolved in distilled CHCl$_3$. The DCC solution was added little by little to the 300 ml short neck flask with stirring in ice bath. After completion of the reaction, condensation and filtration were repeated until complete removal of DCU. The residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After filtration, it was subjected to vacuum concentration to yield a transparent oil-form product. The oil-form product was purified by column chromatography (with a developing solvent of CHCl$_3$: MeOH=98:2).

Yield: 5.46 g (oil-form product) (85%)

$^1$H-NMR (CDCl$_3$, 300 MHz):7.33, 7.29 (10H, Glu OBzl, Ser Bzl); 7.19 (1H, Glu NH); 5.38 (1H, Ser NH); 5.10 (2H, Glu —OBzl —CH$_2$—); 4.86, 4.65 (2H, -OTce —CH$_2$—); 4.77 (1H, Ser αCH); 4.53 (2H, Ser -Bzl —CH$_2$—); 4.30 (1H, Glu αCH); 3.91, 3.57 (2H, Ser βCH$_2$); 2.45 (2H, Glu βCH$_2$); 2.32, 2.05 (2H, Glu γCH$_2$); 1.54 (9H, Boc t-Bu).

5c: Synthesis of Boc-Ala-Ser(Bzl)-Glu(OBzl)-OTce

HCl.H-Ser(Bzl)-Glu(OBzl)-OTce (10.0 mmol) in a 300 ml short neck flask was dissolved in distilled CHCl$_3$ (50 ml), was neutralized with NMM (1.10 ml, 10.0 mmol), and was mixed with Boc-Ala-OH (2.08 g, 11.0 mmol) and HOBt (1.49 g, 11.0 mmol). DCC (2.27 g, 11.0 mmol) was separately dissolved in distilled CHCl$_3$ (20 ml) and was added little by little to the 300 ml short neck flask. After completion of the reaction, condensation and filtration were repeated until complete removal of DCU. The residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After filtration, it was subjected to vacuum concentration. The residue was crystallized with Et$_2$O—petroleum ether to yield a white crystalline product.

Yield: 5.51 g (77%), $[\alpha]_D^{20}$=−24.3° (c 0.1, MeOH), melting point: 90 to 93° C.

Mass Spectrometry (ESI Method): m/e=738.1 ([M+Na]$^+$)

$^1$H-NMR (DMSO-d$_6$, 300 MHz):8.48, 7.86, 6.95 (3H, NH); 7.33, 7.29 (10H, Glu OBzl, Ser Bzl); 5.08 (2H, Glu OBzl —CH$_2$—); 4.86 (2H, -OTce —CH$_2$—); 4.54, 4.47, 4.00 (3H, αCH); 4.47 (2H, Ser Bzl —CH$_2$—); 3.60 (2H, Ser βCH$_2$); 2.49 (2H, Glu γCH$_2$); 2.11, 1.98 (2H, Glu βCH$_2$); 1.35 (9H, Boc t-Bu); 1.15 (3H, Ala αCH$_3$).

5d: Synthesis of Boc-Glu(OBzl)-Ala-Ser(Bzl)-Glu(OBzl)-OTce (SEQ ID NO: 29)

HCl.H-Ser(Bzl)-Glu(OBzl)-OTce (1.44 g, 2.20 mmol) in a 500 ml short neck flask was dissolved in DMF (80 ml) and was neutralized with NMM (0.242 ml, 2.20 mmol). After addition of Boc-Glu(OBzl)-OH (0.891 g, 2.64 mmol) and HOBt (0.357 g, 2.64 mmol), EDC.HCl (0.506 g, 2.64 mmol) was further added to the reaction solution with stirring in the 500 ml short neck flask in ice bath. After completion of the reaction, the reaction mixture was concentrated. The residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After filtration, it was subjected to vacuum concentration. The residue was recrystallized with AcOEt-hexane to yield a white crystalline product.

Yield: 1.94 g (94%), $[\alpha]_D^{20}$=−21.4° (c 0.1, MeOH), melting point: 101 to 103° C.

Mass Spectrometry (ESI Method): m/e=935.2 ([M+H]$^+$), 957.2 ([M+Na]$^+$), 973.2 ([M+K]$^+$)

$^1$H-NMR (DMSO-d$_6$, 300 MHz): 8.43, 8.12, 7.89, 6.94 (4H, NH); 7.33-7.26 (15H, Glu OBzl, Ser Bzl); 5.07, 5.06 (4H, Glu OBzl —CH$_2$—); 4.90, 4.81 (2H, -OTce —CH$_2$—); 4.45 (2H, Ser Bzl —CH$_2$—); 4.55, 4.45, 4.33 3.93 (4H, αCH); 3.58 (2H, Ser βCH$_2$); 2.46, 2.35 (4H, Glu γCH$_2$); 2.10, 1.93, 1.76 (4H, Glu βCH$_2$); 1.35 (9H, Boc t-Bu), 1.18 (3H, Ala βCH$_3$).

5d: Synthesis of Boc-[Glu(OBzl)]$_2$-Ala-Ser(Bzl)-Glu(OBzl)-OTce (SEQ ID NO: 30)

HCl.H-Glu(OBzl)-Ala-Ser(Bzl)-Glu(OBzl)-OTce (SEQ ID NO: 31) (1.48 g, 1.70 mmol) in a 500 ml short neck flask was dissolved in DMF (80 ml) and was neutralized with NMM (0.187 ml, 1.70 mmol). After addition of Boc-Glu(OBzl)-OH (0.631 g, 1.87 mmol) and HOBt (0.253 g, 1.87 mmol), EDC.HCl (0.358 g, 1.87 mmol) was further added to the reaction solution with stirring in the 500 ml short neck flask in ice bath. After completion of the reaction, the reaction mixture was concentrated. The residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After filtration, it was subjected to vacuum concentration. The residue was recrystallized with AcOEt-hexane to yield a white crystalline product.

Yield: 1.81 g (92%), $[\alpha]_D^{20}$=−17.9° (c 0.1, MeOH), melting point: 175 to 179° C.

Mass Spectrometry (ESI Method): m/e=1154.4 ([M+H]$^+$), 1176.4 ([M+Na]$^+$), 1192.2 ([M+K]$^+$)

$^1$H-NMR (DMSO-d$_6$, 300 MHz): 8.45, 8.10, 8.08, 7.89, 7.02 (5H, NH); 7.32-7.28 (20H, Glu OBzl, Ser Bzl); 5.08, 5.04 (6H, Glu OBzl —CH$_2$—); 4.90, 4.80 (2H, -OTce —CH$_2$—); 4.44 (2H, Ser Bzl —CH$_2$—); 4.56, 4.44, 4.30, 3.92 (5H, αCH); 3.58 (2H, Ser βCH$_2$); 2.44, 2.38 (6H, Glu γCH$_2$); 2.11, 1.90, 1.77 (6H, Glu βCH$_2$); 1.33 (9H, Boc t-Bu); 1.28 (3H, Ala βCH$_3$).

5e: Synthesis of Boc-[Glu(OBzl)]$_3$-Ala-Ser(Bzl)-Glu(OBzl)-OTce (SEQ ID NO: 32)

HCl.H-[Glu(OBzl)]$_2$-Ala-Ser(Bzl)-Glu(OBzl)-OTce (SEQ ID NO: 33) (1.31 g, 1.20 mmol) in a 500 ml short neck flask was dissolved in DMF (80 ml) and was neutralized with NMM (0.132 ml, 1.20 mmol). After addition of Boc-Glu(OBzl)-OH (0.445 g, 1.32 mmol) and HOBt (0.178 g, 1.32 mmol), EDC.HCl (0.263 g, 1.32 mmol) was further added to the reaction solution with stirring in the 500 ml short neck flask in ice bath. After completion of the reaction, the reaction mixture was concentrated and was mixed with water to cause a precipitation. The precipitate was filtered off, was placed on a glass filter, and was sequentially washed with a 10% aqueous citric acid solution, water, a saturated aqueous NaHCO$_3$ solution, and water. The precipitate was recrystallized with CHCl$_3$-hexane to yield a white crystalline product.

Yield: 1.47 g (89%), $[\alpha]_D^{20}$=−25.0° (c 0.1, MeOH), melting point: 222 to 224° C.

$^1$H-NMR (DMSO-d$_6$, 300 MHz): 8.46, 8.08, 7.89, 7.00 (6H, NH); 7.30-7.26 (25H, Glu OBzl, Ser Bzl); 5.04 (8H, Glu OBzl —CH$_2$—); 4.90, 4.80 (2H, OTce-CH$_2$); 4.44 (2H, Ser Bzl —CH$_2$—); 4.56, 4.45, 4.28, 3.91 (6H, αCH); 3.58 (2H, Ser βCH$_2$); 2.46, 2.37 (8H, Glu γCH$_2$); 2.11, 1.90, 1.78 (8H, Glu βCH$_2$); 1.34 (9H, Boc t-Bu), 1.16 (3H, Ala βCH$_3$).

5f: Synthesis of Boc-[Glu(OBzl)]$_4$-Ala-Ser(Bzl)-Glu(OBzl)-OTce (SEQ ID NO: 28)

HCl.H-[Glu(OBzl)]$_3$-Ala-Ser(Bzl)-Glu(OBzl)-OTce (SEQ ID NO: 34) (1.18 g, 0.90 mmol) in a 500 ml short neck flask was dissolved in DMF (80 ml) and was neutralized with NMM (99 µl, 0.90 mmol). After addition of Boc-Glu(OBzl)-OH (0.334 g, 0.99 mmol) and HOBt (0.134 g, 0.99 mmol), EDC HCl (0.190 g, 0.99 mmol) was further added to reaction solution with stirring in the 500 ml short neck flask in ice bath. After completion of the reaction, the reaction mixture was concentrated and was mixed with water to cause a precipitation. The precipitate was filtered off, was placed on a glass filter, and was sequentially washed with a 10% aqueous citric acid solution, water, a saturated aqueous NaHCO$_3$ solution, and water. Reprecipitation with DMF-water yielded a white precipitate.

Yield: 1.26 g (90%), $[\alpha]_D^{20}$=−24.00 (c 0.1, DMF), melting point: 240 to 243° C.

$^1$H-NMR (DMSO-d$_6$, 300 MHz):8.46, 8.08, 7.90, 7.00 (7H, NH); 7.32-7.26 (30H, Glu OBzl, Ser Bzl); 5.04 (10H, Glu OBzl —CH$_2$); 4.90, 4.80 (2H, -OTce —CH$_2$—); 4.43 (2H, Ser Bzl —CH$_2$—); 4.55, 4.43, 4.24, 3.90 (7H, αCH), 3.58 (2H, Ser βCH$_2$), 2.47, 2.38 (OH, Glu γCH$_2$), 2.10, 1.90, 1.78 (10H, Glu βCH$_2$); 1.32 (9H, Boc t-Bu), 1.16 (3H, Ala βCH$_3$).

Example 6

(6) Synthesis of Boc-Asp(OBzl)-Phe-Lys(Cl-Z)-Thr(Bzl)-Pro-Asn-Asn-Asp(OBzl)-Gly-Gly-OBzl (SEQ ID NO: 35) by Fragment Condensation

6a: Synthesis of Boc-Asp(OBzl)-Phe-Lys(Cl-Z)-Thr(Bzl)-Pro-OH (SEQ ID NO: 36)

(Synthesis Step 1)

Boc-Asp(OBzl)-Phe-Lys(Cl-Z)-Thr(Bzl)-Pro-OTce (SEQ ID NO: 17) (0.55 g, 0.46 mmol) in a short neck flask was dissolved in CH$_3$COOH (9 ml) and was mixed with H$_2$O (1 ml). After addition of zinc powder (1.0 g), the mixture was stirred at room temperature for 1 hour. After completion of the reaction, the reaction mixture was filtered. The filtrate was concentrated and was mixed with a 10% aqueous citric acid solution to yield a precipitate. The precipitate was placed on a glass filter and was washed with ion exchange water.

Yield: 0.39 g (81%), $[\alpha]_D^{20}$=−36.1° (c 0.1, MeOH), melting point: 88 to 91° C.

(Synthesis Step 2)

Boc-Asp(OBzl)-Phe-Lys(Cl-Z)-Thr(Bzl)-Pro-OTce (SEQ ID NO: 17) (3.56 g, 3.00 mmol) in a short neck flask was dissolved in CH$_3$COOH (9 ml) and was mixed with H$_2$O (1 ml). After addition of zinc powder (1.0 g), the mixture was stirred at room temperature for 1 hour. The progress of the reaction was monitored by thin layer chromatography. After confirmation of the termination of the reaction, the reaction mixture was filtered. The filtrate was concentrated and was mixed with a 10% aqueous citric acid solution to cause a precipitation. The precipitate was placed on a glass filter and was washed with ion exchange water several times.

Yield: 1.71 g (91%), $[\alpha]_D^{20}$=−51.0° (c 0.1, MeOH), melting point: 88 to 90° C.

6b: Synthesis of Boc-Asp(OBzl)-Phe-Lys(Cl-Z)-Thr(Bzl)-Pro-Asn-Asn-Asp(OBzl)-Gly-Gly-OBz (SEQ ID NO: 35)

TFA.H-Asn-Asn-Asp(OBzl)-Gly-Gly-OBzl (SEQ ID NO: 37) (0.25 g, 0.33 mmol) in a short neck flask was dissolved in DMF (10 ml), was neutralized with NMM (36 µl), and was mixed with Boc-Asp(OBzl)-Phe-Lys(Cl-Z)-Thr(Bzl)-Pro-OH (SEQ ID NO: 36) (0.37 g, 0.37 mmol), HOBt (0.094 g, 0.69 mmol), and EDC.HCl (0.066 g, 0.37 mmol). The mixture was stirred in an ice cold-MeOH bath for 13.5 hours. After completion of the reaction, the reaction mixture was concentrated and was mixed with ion exchange water to cause a precipitation. The precipitate was placed on a glass filter, was sequentially washed with a 10% aqueous citric acid solution, water, a saturated aqueous NaHCO₃ solution, water, and saturated saline, and was dried in a desiccator to yield white powder. The white powder was purified by gel filtration column chromatography (Sephadex LH20, DMF).

Yield: 0.35 g (63%), [α]$_D^{20}$=−34.9° (c 0.1, DMF), melting point: 94 to 97° C.

Example 7

(7) Synthesis of Boc-Asn-Lys(Cl-Z)-Thr(Bzl)-Tyr(Cl₂-Bzl)-Asp(OBzl)-Leu-Asp(OBzl)-Phe-Lys(Cl-Z)-Thr(Bzl)-Pro-Asn-Asn-Asp(OBzl)-Gly-Gly-OBzl (SEQ ID NO: 38)

7a: Synthesis of Boc-Asn-Lys(Cl-Z)-Thr(Bzl)-Tyr(Cl₂-Bzl)-Asp(OBzl)-Leu-OH (SEQ ID NO: 39)

(Synthesis Step 1)
Boc-Asn-Lys(Cl-Z)-Thr(Bzl)-Tyr(Cl₂-Bzl)-Asp(OBzl)-Leu-OTce (SEQ ID NO: 19) (2.40 g, 1.61 mmol) in a short neck flask was dissolved in CH₃COOH (27 ml) and was mixed with H₂O (3 ml). After addition of zinc powder (4.0 g), the mixture was stirred at room temperature for 1 hour. After completion of the reaction, the reaction mixture was filtered. The filtrate was concentrated and was mixed with a 10% aqueous citric acid solution to cause a precipitation. The precipitate was placed on a glass filter and was washed with ion exchange water.

Yield: 1.93 g (88%), [α]$_D^{20}$=−21.2° (c 0.1, MeOH), melting point: 192 to 194° C.

(Synthesis Step 2)
Boc-Asn-Lys(Cl-Z)-Thr(Bzl)-Tyr(Cl₂-Bzl)-Asp(OBzl)-Leu-OTce (SEQ ID NO: 19) (1.17 g, 0.78 mmol) in a short neck flask was dissolved in CH₃COOH (27 ml) and was mixed with H₂O (3 ml). After addition of zinc powder (4.0 g), the mixture was stirred at room temperature for 1 hour. After completion of the reaction, the reaction mixture was filtered. The filtrate was concentrated and was mixed with a 10% aqueous citric acid solution to cause a precipitation. The precipitate was placed on a glass filter and was washed with ion exchange water several times.

Yield: 0.95 g (89%), [α]$_D^{20}$=−17.3° (c 0.1, MeOH), melting point: 191 to 193° C.

¹H-NMR (DMSO, 300 MHz): 8.35, 7.83, 7.53, 7.43, 7.25, 7.14, 6.91, 6.87 (10H, Bzl; 4H, Cl-Z; 3H; 3H, Cl₂-Bzl; 4H, Tyr C₆H₅; 6H, NH; 1H, Lys εNH; 2H, Asn γNH₂); 5.18, 5.11, 4.60 (4H, Bzl —CH₂; 2H, Cl₂-Bzl —CH₂—; 2H, Cl-Z —CH₂—); 4.87, 4.83, 4.71, 4.55, 4.43, 4.30, 4.23 (6H, αCH; 2H, Bzl —CH₂—; 1H, Thr βCH); 3.15, 3.05, 3.02, 2.94, 2.65 (2H, Asp βCH₂; 1H, Tyr βCH₂; 2H, Lys εCH₂; 2H, Asn βCH₂); 1.71, 1.69, 1.51 (2H, Leu βCH₂; 1H, Leu γCH; Lys βCH₂; Lys γCH₂); 1.41 (9H, Boc t-Bu); 1.02 (3H, Thr γCH₃); 0.81 (6H, Leu δCH₂).

7b: Synthesis of Boc-Asn-Lys(Cl-Z)-Thr(Bzl)-Tyr(Cl₂-Bzl)-Asp(OBzl)-Leu-Asp(OBzl)-Phe-Lys(Cl-Z)-Thr(Bzl)-Pro-Asn-Asn-Asp(OBzl)-Gly-Gly-OBzl (SEQ ID NO: 38)

TFA.H-Asp(OBzl)-Phe-Lys(Cl-Z)-Thr(Bzl)-Pro-Asn-Asn-Asp(OBzl)-Gly-Gly-OBzl (SEQ ID NO: 40) (0.27 g, 0.16 mmol) in a short neck flask was dissolved in DMF (10 ml), was neutralized with DIEA (27 μl, 0.16 mmol), and was mixed with Boc-Asn-Lys(Cl-Z)-Thr(Bzl)-Tyr(Cl₂-Bzl)-Asp(OBzl)-Leu-OH (SEQ ID NO: 39) (0.23 g, 0.17 mmol), DIEA (29 μl, 0.17 mmol), and HATU (0.065 g, 0.17 mmol). The mixture was stirred in an ice cold-MeOH bath for 1.5 hours. After completion of the reaction, the reaction mixture was concentrated and was mixed with ion exchange water to cause a precipitation. The precipitate was placed on a glass filter, was sequentially washed with a 10% aqueous citric acid solution, water, a saturated aqueous NaHCO₃ solution, water, and saturated saline, and was dried in a desiccator to yield white powder.

Yield: 0.47 g (94%), [α]$_D^{20}$=−23.3° (c 0.1, DMF), melting point: 201 to 203° C.

Example 8

(8) Synthesis of Boc-Phe-Tyr(Cl₂-Bzl)-Asn-Ser(Bzl)-Glu(OBzl)-Asn-Lys(Cl-Z)-Thr(Bzl)-Tyr(Cl₂-Bzl)-Asp(OBzl)-Leu-Asp(OBzl)-Phe-Lys(Cl-Z)-Thr(Bzl)-Pro-Asn-Asn-Asp(OBzl)-Gly-Gly-OBzl (SEQ ID NO: 41) by Fragment Condensation 8a: Synthesis of Boc-Phe-Tyr(Cl₂-Bzl)-Asn-Ser(Bzl)-Glu(OBzl)-OH (SEQ ID NO: 42)

Boc-Phe-Tyr(Cl₂-Bzl)-Asn-Ser(Bzl)-Glu(OBzl)-OTce (SEQ ID NO: 23) (1.23 g, 1.00 mmol) in a 300 ml short neck flask was dissolved in 90% acetic acid (30.0 ml) and was mixed with zinc powder (2 g) with stirring. After completion of the reaction, the reaction mixture was filtered. The filtrate was concentrated and was mixed with a 10% aqueous citric acid solution to cause a precipitation. The precipitate was placed on a glass filter and was washed with water.

Yield: 1.05 g (95%), [α]$_D^{20}$=−23.9° (c 0.1, DMF), melting point: 205 to 208° C.

Mass Spectrometry (ESI Method): m/e=1097.2 ([M+H]⁺), 1119.4 ([M+Na]⁺), 1135.2 ([M+K]⁺)

8b: Synthesis of Boc-Phe-Tyr(Cl₂-Bzl)-Asn-Ser(Bzl)-Glu(OBzl)-Asn-Lys(Cl-Z)-Thr(Bzl)-Tyr(Cl₂-Bzl)-Asp(OBzl)-Leu-Asp(OBzl)-Phe-Lys(Cl-Z)-Thr(Bzl)-Pro-Asn-Asn-Asp(OBzl)-Gly-Gly-OBzl (SEQ ID NO: 41)

TFA.H-Asn-Lys(Cl-Z)-Thr(Bzl)-Tyr(Cl₂-Bzl)-Asp(OBzl)-Leu-Asp(OBzl)-Phe-Lys(Cl-Z)-Thr(Bzl)-Pro-Asn-Asn-Asp(OBzl)-Gly-Gly-OBzl (SEQ ID NO: 43) (0.354 g, 0.12 mmol) in a 300 ml short neck flask was dissolved in DMF (80 ml) and was neutralized with DIEA (20.4 μl, 0.120 mmol). Separately Boc-Phe-Tyr(Cl₂-Bzl)-Asn-Ser(Bzl)-Glu(OBzl)-OH (SEQ ID NO: 42) (0.138 g, 0.126 mmol) was dissolved in DMF (50 ml) and was neutralized with DIEA (21.4 μl, 0.126 mmol). The latter solution was added with stirring in the former solution in the 300 ml short neck flask in ice bath. HATU (0.048 g, 0.126 mmol) was further added to the solution mixture. After completion of the reaction, the reaction mixture was concentrated and was mixed with a saturated aqueous NaHCO₃ solution to cause a precipitation. The precipitate was filtered off, was placed on a glass filter, and was sequentially washed with a saturated aqueous NaHCO₃ solution, water, a 10% aqueous citric acid solution, and water. The precipitate was purified by gel filtration column chromatography (Sephadex LH60, DMF).

Yield: 0.352 g (73%), [α]$_D^{20}$=−14.4° (c 0.1, DMF), melting point: 115 to 117° C.

Example 9

(9) Synthesis of Boc-Glu(OBzl)-Glu(OBzl)-Glu(OBzl)-Glu(OBzl)-Ala-Ser(Bzl)-Glu(OBzl)-Phe-Tyr(Cl$_2$-Bzl)-Asn-Ser(Bzl)-Glu(OBzl)-Asn-Lys(Cl-Z)-Thr(Bzl)-Tyr(Cl$_2$-Bz)-Asp(OBzl)-Leu-Asp(OBzl)-Phe-Lys(Cl-Z)-Thr(Bzl)-Pro-Asn-Asn-Asp(OBzl)-Gly-Gly-OBzl (Protected 28-Residue Peptide) (SEQ ID NO: 44)

9a: Synthesis of Boc-[Glu(OBzl)]$_4$-Ala-Ser(Bzl)-Glu(OBzl)-OH (SEQ ID NO: 45)

Boc-[Glu(OBzl)]$_4$-Ala-Ser(Bzl)-Glu(OBzl)-OBzl (SEQ ID NO: 46) (1.28 g, 0.800 mmol) in a 300 ml short neck flask was dissolved in acetic acid (36 ml) and DMF (36 ml) and was mixed with zinc powder (2 g) with stirring. After completion of the reaction, the reaction mixture was filtered. The filtrate was concentrated and was mixed with a 10% aqueous citric acid solution to cause a precipitation. The precipitate was filtered off, was placed on a glass filter, and was washed with water.

Yield: 1.06 g (90%), $[\alpha]_D^{20}$=57.5° (c 0.1, DMF), melting point: 194 to 198° C.

Mass Spectrometry (ESI Method): m/e=1484.5 ([M+Na]$^+$)

9b: Synthesis of Boc-Glu(OBzl)-Glu(OBzl)-Glu(OBzl)-Glu(OBzl)-Ala-Ser(Bzl)-Glu(OBzl)-Phe-Tyr(Cl$_2$-Bzl)-Asn-Ser(Bzl)-Glu(OBzl)-Asn-Lys(Cl-Z)-Thr(Bzl)-Tyr(Cl$_2$-Bz)-Asp(OBzl)-Leu-Asp(OBzl)-Phe-Lys(Cl-Z)-Thr(Bzl)-Pro-Asn-Asn-Asp(OBzl)-Gly-Gly-OBzl (SEQ ID NO: 44)

TFA.H-Phe-Tyr(Cl$_2$-Bzl)-Asn-Ser(Bzl)-Glu(OBzl)-Asn-Lys(Cl-Z)-Thr(Bzl)-Tyr(Cl$_2$-Bzl)-Asp(OBzl)-Leu-Asp(OBzl)-Phe-Lys(Cl-Z)-Thr(Bzl)-Pro-Asn-Asn-Asp(OBzl)-Gly-Gly-OBzl (SEQ ID NO: 47) (386 mg, 96 μmol) in a 300 ml short neck flask was dissolved in DMF (60 ml) and was neutralized with DIEA (16.32 μl, 96.0 μmol). Separately Boc-[Glu(OBzl)]$_4$-Ala -Ser(Bzl)-Glu(OBzl)-OH (SEQ ID NO: 45) (148.0 mg, 100.8 μmol) was dissolved in DMF (30 ml) and was neutralized with DIEA(17.14 μl, 100.8 μmol). The latter solution was added with stirring in the former solution in the 300 ml short neck flask in ice bath. HATU (38.0 mg, 100.8 μmol) was further added to the solution mixture. After completion of the reaction, the reaction mixture was concentrated and was mixed with a saturated aqueous NaHCO$_3$ solution to cause a precipitation. The precipitate was filtered off, was placed on a glass filter, and was sequentially washed with a saturated aqueous NaHCO$_3$ solution, water, a 10% aqueous citric acid solution, and water. The precipitate was purified by gel filtration column chromatography (Sephadex LH60, DMF).

Yield: 0.40 g (77%), $[\alpha]_D^{20}$=14.1° (c 0.1, DMF), melting point: 305 to 308° C.

Example 10

Figure 3:
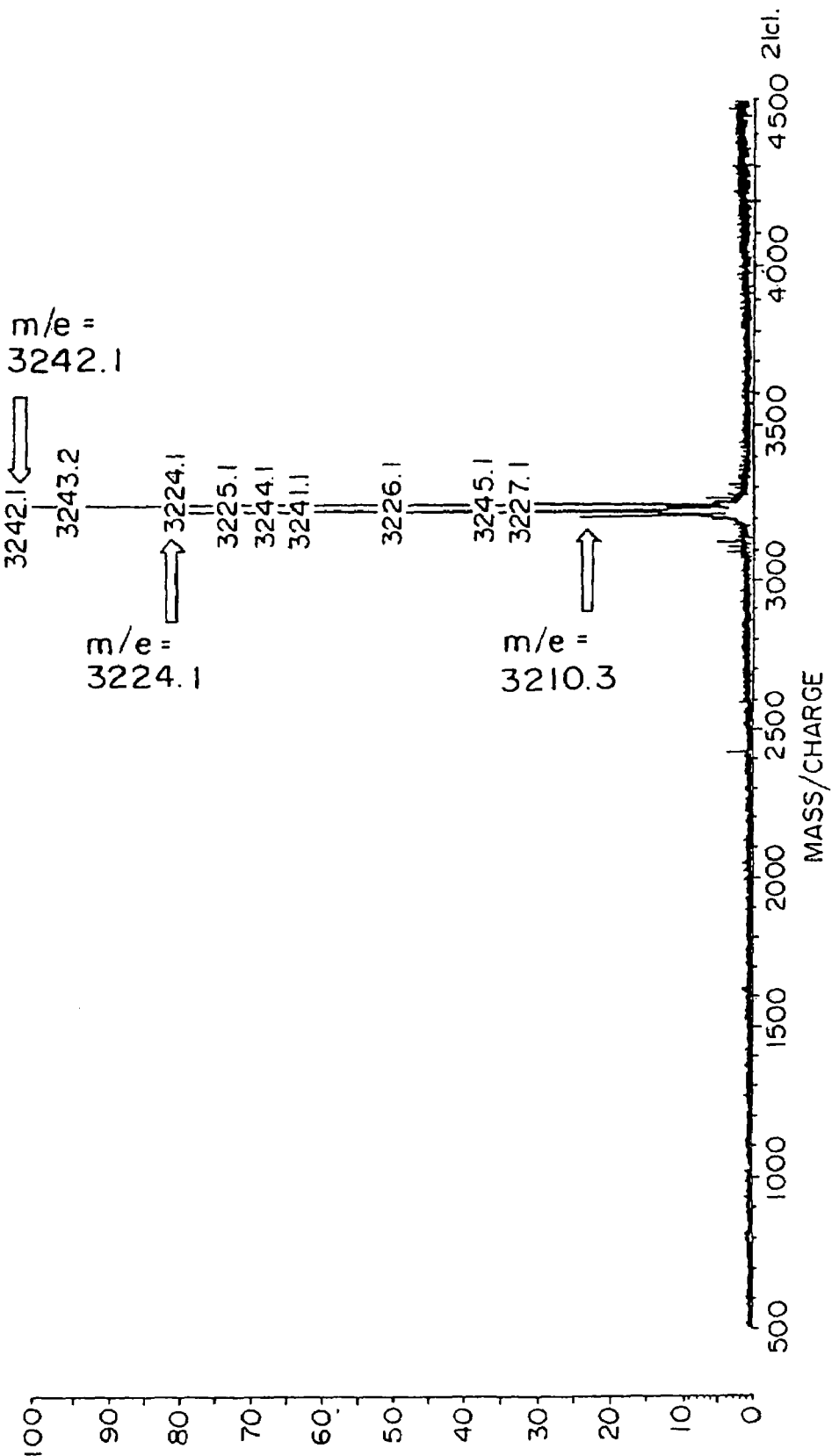
FIG. 3 shows spectral data (mass range m/e of 500 to 4500) of the synthesis product by mass spectrometry according to the MALDI-TOF method, with regard to the peptide compound H-Glu-Glu-Glu-Glu-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Gly-Gly-OH (SEQ ID NO: 13) as one example of the present invention.
Figure 4:
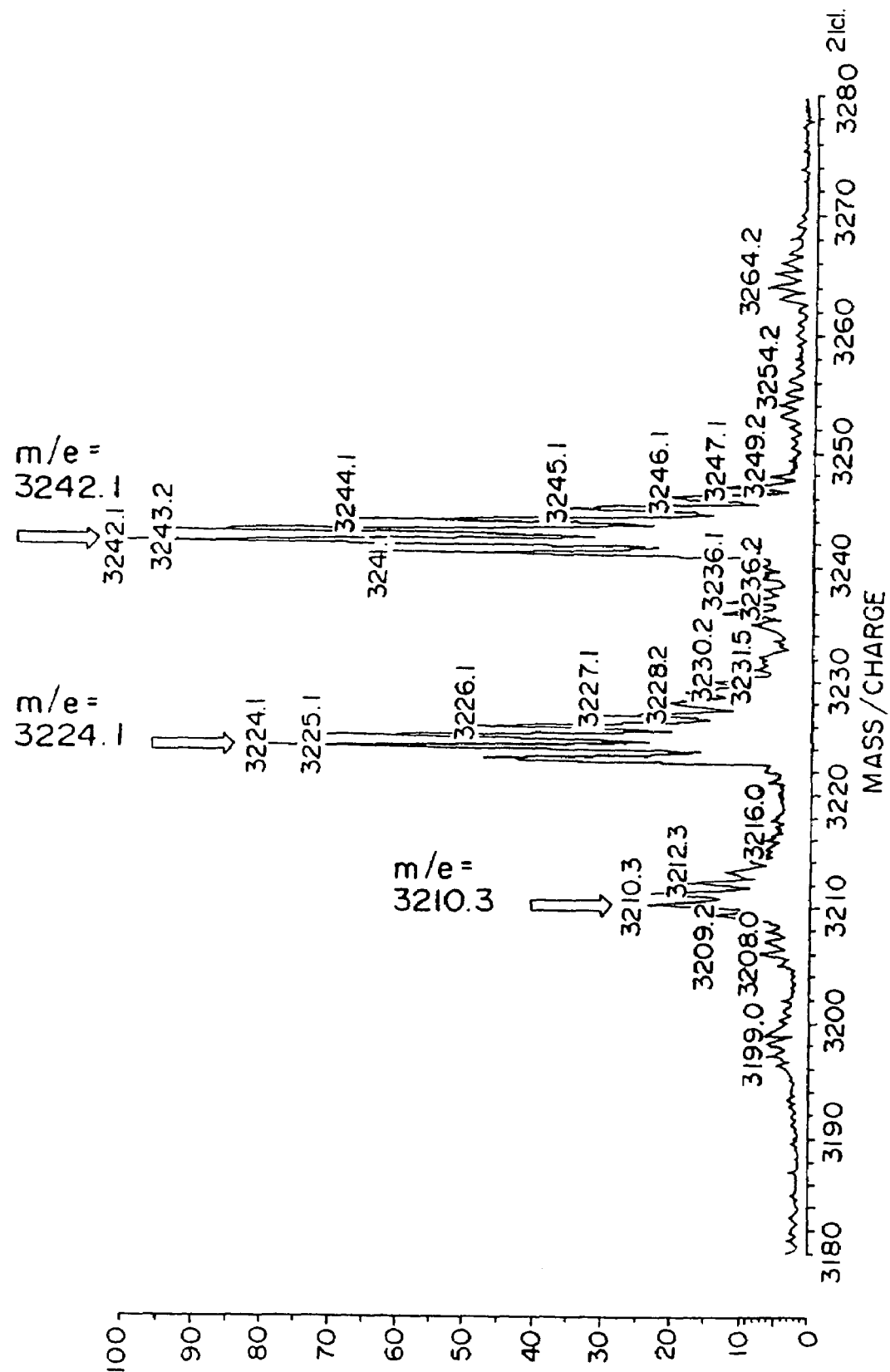
FIG. 4 shows spectral data (mass range m/e of 3180 to 3280) of the synthesis product by mass spectrometry according to the MALDI-TOF method, with regard to the peptide compound H-Glu-Glu-Glu-Glu-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Gly-Gly-OH (SEQ ID NO: 13) as one example of the present invention.

(10) Synthesis of H-Glu-Glu-Glu-Glu-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Gly-Gly-OH (SEQ ID NO: 13) by Final Deprotection Reaction In a 50 ml short neck flask in ice bath, m-cresol (0.167 ml, 1.60 mmol), thioanisole (374 mg, 3.20 mmol), TFA (2.38 ml), and TFMSA (0.283 ml, 3.20 mmol) were sequentially added. After addition of Boc-Glu(OBzl)-Glu(OBzl)-Glu(OBzl)-Glu(OBzl)-Ala-Ser-Glu(OBzl)-Phe-Tyr(Cl$_2$-Bzl)-Asn-Ser(Bzl)-Glu(OBzl)-Asn-Lys(Cl-Z)-Thr(Bzl)-Tyr(Cl$_2$-Bzl)-Asp(OBzl)-Leu-Asp(OBzl)-Phe-Lys(Cl-Z)-Thr(Bzl)-Pro-Asn-Asn-Asp(OBzl)-Gly-Gly-OBzl (SEQ ID NO: 44) (0.350 mg, 0.0640 mmol), the reaction mixture was stood still. After 2 hours, the reaction mixture was mixed with distilled Et$_2$O and was left in a refrigerator overnight. The reaction mixture was then placed in a centrifugal tube and was centrifuged for removal of the supernatant. The centrifugation was repeated three times. After drying, the obtained powder was dissolved in DMF and was purified by gel filtration column chromatography (Sephadex LH60, DMF). The resulting product was identified by mass spectrometry. FIGS. 3 and 4 show spectral data.

Yield: 0.160 g (81%), $[\alpha]_D^{20}$=−21.3° (c 0.1, DMF), melting point: 274 to 276° C.

Mass Spectrometry (MALDI-TOF Method): m/e=m/e=3242.1 ([M+H]$^+$), 3224.1 ([M+H—H$_2$O]$^+$)

Example 11

(11) Synthesis of Boc-Asn-Asn-Asp(OBzl)-Gly-OTce (SEQ ID NO: 50)

11a: Synthesis of Boc-Asp(OBzl)-Gly-OTce

HCl.H-Gly-OTce (5.09 g, 20.0 mmol) was dissolved in distilled dichloromethane, was neutralized with NMM (2.20 ml, 20.0 mmol), and was mixed with Boc-Asp(OBzl)-OH (7.11 g, 22.0 mmol) and DCC (4.54 g, 22.0 mmol) with stirring.

After filter-out of DCUrea, the filtrate was evaporated for condensation. The residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After condensation, the obtained oil was purified by silica gel column chromatography with developing solvents of AcOEt: benzene=1:3 and AcOEt: benzene=1:1.

Yield: 6.24 g (61%) (oil-form product)

$^1$H-NMR (CDCl$_3$, 300 MHz): 7.26 (10H, -Bzl), 4.73 (2H, -OTce —CH$_2$—), 7.06, 5.56 (2H, NH), 5.16, 5.10 (4H, Bzl —CH$_2$—), 4.52, 4.09 and (3H, αCH), 3.13 and 2.80 (2H, Asp βCH$_2$), 1.44 (9H, Boc t-Bu).

11b: Synthesis of Boc-Asn-Asp(OBzl)-Gly-OTce

HCl.H-Asp(OBzl)-Gly-OTce (5.68 g, 12.7 mmol) was dissolved in DMF, was neutralized with NMM (1.34 ml, 12.7 mmol), and was mixed with Boc-Asn-OH (3.11 g, 14.0 mmol), HOBt (3.62 g, 28.0 mmol), and EDC.HCl (2.57 g, 14.0 mmol) with stirring. After condensation, the residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After condensation, hexane was added to yield a precipitation.

Yield: 5.08 g (64%), $[\alpha]_D^{20}$=−3.8° (c 0.1, MeOH), melting point: 93 to 95° C.

$^1$H-NMR (DMSO-d$_6$, 300 MHz):7.35 (10H, Bzl), 4.88 (2H, -OTce —CH$_2$—), 7.60, 6.02, 5.93, 5.55 (5H, NH), 5.12, 5.07 (4H, Bzl —CH$_2$—), 4.87, 4.41 (2H, αCH), 4.11, 4.08 (2H, Gly αCH), 2.86, 2.67, 2.52, 2.43 (4H, βCH), 1.36 (9H, Boc t-Bu).

11c: Synthesis of
Boc-Asn-Asn-Asp(OBzl)-Gly-OTce
(SEQ ID NO: 50)

TFA.H-Asn-Asp(OBzl)-Gly-OTce (1.12 g, 2.00 mmol) was dissolved in DMF, was neutralized with NMM (220 ml, 2.00 mmol), and was mixed with Boc-Asn-OH (0.51 g, 2.20 mmol), HOBt (0.60 g, 4.40 mmol), and EDC.HCl (0.44 g, 2.20 mmol). After completion of the reaction, the reaction mixture was concentrated. Addition of ion exchange water to the residue caused a precipitation. After filtration, the precipitate was placed on a glass filter and was sequentially washed with a 10% aqueous citric acid solution, water, a saturated aqueous NaHCO$_3$ solution, water, and saturated saline. The precipitate was dissolved in DMF and was reprecipitated by addition of Et$_2$O.

Yield: 1.29 g (87%), $[\alpha]_D^{20}$=−26.4° (c 0.1, DMF), melting point: 206 to 208° C.

Mass Spectrometry (ESI Method): m/e=639.0 ([M+H]$^+$), 1279.4 ([2M+H]$^+$)

$^1$H-NMR (DMSO-d$_6$, 500 MHz): 7.37 (10H, Bzl), 4.90 (2H, -OTce —CH$_2$—), 8.37, 8.13, 8.06, 7.44, 6.99, 6.92 (8H, NH), 5.12, 5.08 (4H, Bzl —CH$_2$—), 4.65, 4.46, 4.24, 3.91 (5H, αCH), 2.89, 2.64, 2.56, 2.40 (4H, βCH), 1.36 (9H, Boc t-Bu).

Example 12

(12) Synthesis of Boc-Cys(Acm)-Gly-Gly-Ala-Ser(Bzl)-Glu(OBzl)-OTce (SEQ ID NO: 51)

12a: Synthesis of Boc-Gly-Ala-Ser(Bzl)-Glu(OBzl)-OTce (SEQ ID NO: 52)

HCl.H-Ala-Ser(Bzl)-Glu(OBzl)-OTce (4.5 mmol) in a 300 ml short neck flask was dissolved in distilled THF (40 ml), was neutralized with NMM (495 ml, 4.5 mmol), and was mixed with Boc-Gly-OH (0.867 g, 4.95 mmol), HOBt (0.867 g, 4.95 mmol), and EDC.HCl (0.949 g, 4.95 mmol). After completion of the reaction, the residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After filtration, it was subjected to vacuum concentration, followed by crystallization with CHCl$_3$—hexane to yield a white precipitate.

Yield: 3.10 g (89%), $[\alpha]_D^{20}$=−27.4 (c 0.1, MeOH), melting point: 142 to 144° C.

$^1$H-NMR (CDCl$_3$, 300 MHz): 7.35, 6.89, 6.68, 5.09 (4H, NH); 7.33, 7.30 (10H, Glu OBzl, Ser Bzl); 5.09 (2H, Glu OBzl —CH$_2$—); 4.86, 4.65 (2H, -OTce —CH$_2$—); 4.73, 4.43, 3.92, 3.72 (5H, αCH); 4.53 (2H, Ser Bzl —CH$_2$—); 3.61 (2H, Ser βCH$_2$); 2.47 (2H, Glu γCH$_2$); 2.30, 2.11 (2H, Glu βCH$_2$); 1.44 (9H, Boc t-Bu); 1.42, 1.39 (3H, Ala βCH$_3$).

12b: Synthesis of Boc-Gly-Gly-Ala-Ser(Bzl)-Glu(OBzl)-OTce (SEQ ID NO: 53)

HCl.H-Gly-Ala-Ser(Bzl)-Glu(OBzl)-OTce (SEQ ID NO: 54) (4.5 mmol) in a 300 ml short neck flask was dissolved in DMF (40 ml), was neutralized with NMM (495 ml, 4.5 mmol), and was mixed with Boc-Gly-OH (0.867 g, 4.95 mmol), HOBt (0.867 g, 4.95 mmol), and EDC.HCl (0.949 g, 4.95 mmol). After completion of the reaction, the residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After filtration, it was subjected to vacuum concentration, followed by crystallization with AcOEt-hexane to yield a white precipitate.

Yield: 3.43 g (92%), $[\alpha]_D^{20}$=−24.4° (c 0.1, MeOH), melting point: 132 to 134° C.

Mass Spectrometry (ESI Method): m/e=830.2 ([M+H]$^+$), 850.2 ([M+Na]$^+$)

$^1$H-NMR (DMSO-d$_6$, 300 MHz): 8.40, 8.10, 8.01, 7.95, 6.98 (5H, NH); 7.33, 7.29 (10H, Glu OBzl, Ser Bzl); 5.07 (2H, Glu OBzl —CH$_2$—); 4.91, 4.81 (2H, -OTce —CH$_2$—); 4.53, 4.41, 4.35, 3.60, 3.54 (7H, αCH); 4.47 (2H, Ser Bzl —CH$_2$—); 3.61 (2H, Ser βCH$_2$); 2.49 (2H, Glu γCH$_2$); 2.12, 1.96 (2H, Glu βCH$_2$); 1.37 (9H, Boc t-Bu); 1.20, 1.17 (3H, Ala βCH$_3$).

12c: Synthesis of Boc-Cys(Acm)-Gly-Gly-Ala-Ser(Bzl)-Glu(OBzl)-OTce (SEQ ID NO: 54)

HCl.H-Gly-Gly-Ala-Ser(Bzl)-Glu(OBzl)-OTce (SEQ ID NO: 55) (1.07 g, 1.4 mmol) in a 300 ml short neck flask was dissolved in DMF (30 ml), was neutralized with NMM (154 ml, 1.4 mmol), and was mixed with Boc-Cys(Acm)-OH (0.45 g, 1.54 mmol), HOBt (0.236 g, 1.54 mmol), and EDC.HCl (0.295 g, 1.54 mmol). After completion of the reaction, the residue was dissolved in AcOEt, was sequentially washed with a 10% aqueous citric acid solution, water, a saturated aqueous NaHCO$_3$ solution, water, and saturated saline, and was dried with anhydrous Na$_2$SO$_4$. After filtration, it was subjected to vacuum concentration, followed by crystallization with CHCl$_3$-hexane to yield white crystals.

Yield: 1.21 g (86%), $[\alpha]_D^{20}$=−29.8° (c 0.1, MeOH), melting point: 142 to 143° C.

Mass Spectrometry (ESI Method): m/e=1026.3 ([M+Na]$^+$)

$^1$H-NMR (DMSO-d$_6$, 300 MHz): 8.49, 8.43, 8.15, 8.03, 7.01 (7H, NH); 7.35, 7.31 (10H, Glu OBzl, Ser Bzl); 5.08 (2H, Glu OBzl —CH$_2$—); 4.92, 4.82 (2H, -OTce —CH$_2$—); 4.56, 4.38, 4.35, 4.25, 3.74, 3.62 (8H, αCH); 4.48 (2H, Ser Bzl —CH$_2$—); 4.19 (2H, Acm —CH$_2$—); 3.62 (2H, Ser βCH$_2$); 2.92, 2.67 (2H, Cys βCH$_2$); 2.49 (2H, Glu γCH$_2$); 2.13, 1.97 (2H, Glu βCH$_2$); 1.84 (3H, Acm—CH$_3$); 1.38 (9H, Boc t-Bu); 1.21, 1.19 (3H, Ala βCH$_3$)

Example 13

(13) Synthesis of Boc-Asp(OBzl)-Phe-Lys(Cl-Z)-Thr(Bzl)-Pro-Asn-Asn-Asp(OBzl)-Gly-OTce (SEQ ID NO: 56) by Fragment Condensation TFA.H-Asn-Asn-Asp(OBzl)-Gly-OTce (SEQ ID NO: 57) (0.64 g, 0.85 mmol) in a short neck flask was dissolved in DMF, was neutralized with NMM (93 ml), and was mixed with Boc-Asp(OBzl)-Phe-Lys(Cl-Z)-Thr(Bzl)-Pro-OH (SEQ ID NO: 36) (0.94 g, 8.9 mmol), HOBt (0.67 g, 0.50 mmol), and EDC.HCl (0.47 g, 2.50 mmol) with stirring. After completion of the reaction, DMF was concentrated, followed by addition of ion exchange water to cause a precipitation. Then, it was placed on a glass filter, was sequentially washed with a 10% aqueous citric acid solution, water, a saturated aqueous NaHCO$_3$ solution, water, and saturated saline, and was dried in a desiccator to yield white powder. The obtained white powder was recrystallized twice with DMF-Et$_2$O-hexane to yield white crystals.

Yield: 0.94 g (66%), $[\alpha]_D^{20}$=−60.5° (c=0.1, DMF), melting point: 172 to 174° C.

Mass Spectrometry (ESI Method): m/e=639.0 ([M+H]$^+$)

Example 14

(14) Synthesis of Boc-Asn-Lys(Cl-Z)-Thr(Bzl)-Tyr(Cl$_2$-Bzl)-Asp(OBzl)-Leu-Asp(OBzl)-Phe-Lys(Cl-Z)-Thr(Bzl)-Pro-Asn-Asn-Asp(OBzl)-Gly-OTce (SEQ ID NO: 58) by Fragment Condensation TFA.H-Asp(OBzl)-Phe-Lys(Cl-Z)-Thr(Bzl)-Pro-Asn-Asn-Asp(OBzl)-Gly-OTce (SEQ ID NO: 59) (0.87 g, 0.52 mmol) was dissolved in DMF and was mixed with Boc-Asn-Lys(Cl-Z)-Thr(Bzl)-Tyr(Cl$_2$-Bzl)-Asp(OBzl)-Leu-OH (SEQ ID NO: 19) (0.74 g, 0.54 mmol), DIEA (263 ml, 1.56 mmol), and HATU (0.21 g, 0.55 mmol). The mixture was stirred in an ice cold-MeOH bath for 1.5 hours. After completion of the reaction, the reaction mixture was concentrated, followed by addition of ion exchange water to cause a precipitation. Then, it was placed on a glass filter, and was sequentially washed with a 10% aqueous citric acid solution, water, a saturated aqueous NaHCO$_3$ solution, water, and saturated saline. The obtained precipitate was recrystallized with CH$_3$Cl: TFE=3:1-MeOH for purification.

Yield: 1.14 g (75%), $[\alpha]_D^{20}$=−26.5° (c=0.1, DMF), melting point: 236 to 238° C.

Example 15

(15) Synthesis of Boc-Phe-Tyr(Cl$_2$-Bzl)-Asn-Ser(Bzl)-Glu(OBzl)-Asn-Lys(Cl-Z)-Thr(Bzl)-Tyr(Cl$_2$-Bzl)-Asp(OBzl)-Leu-Asp(OBzl)-Phe-Lys(Cl-Z)-Thr(Bzl)-Pro-Asn-Asn-A sp(OBzl)-Gly-OTce (SEQ ID NO: 60) by Fragment Condensation TFA.H-Asn-Lys(Cl-Z)-Thr(Bzl)-Tyr(Cl$_2$-Bzl)-Asp(OBzl)-Leu-Asp(OBzl)-Phe-Lys(Cl -Z)-Thr(Bzl)-Pro-Asn-Asn-Asp(OBzl)-Gly-OTce (SEQ ID NO: 61) (1.10 g, 0.38 mmol) in a short neck flask was dissolved in DMF and was mixed with Boc-Phe-Tyr(Cl$_2$-Bzl)-Asn-Ser(Bzl)-Glu(OBzl)-OH (SEQ ID NO: 42) (0.45 g, 0.40 mmol), DIEA (211 μl, 1.24 mmol), and HATU (0.048 g, 0.126 mmol). After completion of the reaction, the reaction mixture was concentrated, followed by addition of a saturated aqueous NaHCO$_3$ solution to cause a precipitation. Then, the precipitate was filtered and placed on a glass filter, and was sequentially washed with a saturated aqueous NaHCO$_3$ solution, water, a 10% aqueous citric acid solution, and water. The precipitate was purified by gel filtration column chromatography (Sephadex LH60, DMF).

Yield: 0.63 g (42%), $[\alpha]_D^{20}$=−16.5° (c=0.1, DMF), melting point: 188 to 189° C.

Example 16

(16) Synthesis of Boc-Cys(Acm)-Gly-Gly-Ala-Ser(Bzl)-Glu(OBzl)-Phe-Tyr(Cl$_2$-Bzl)-Asn-Ser(Bzl)-Glu(OBzl)-Asn-Lys(Cl-Z)-Thr(Bzl)-Thr(Cl$_2$-Bzl)-Asp(OBzl)-Le u-Asp(OBzl)-Phe-Lys(Cl-Z)-Thr(Bzl)-Pro-Asn-Asn-Asp(OBzl)-Gly-OTce (SEQ ID NO: 62) by Fragment Condensation 16a: Synthesis of Boc-Cys(Acm)-Gly-Gly-Ala-Ser(Bzl)-Glu(OBzl)-OH (SEQ ID NO: 63)

Boc-Cys(Acm)-Gly-Gly-Ala-Ser(Bzl)-Glu(OBzl)-OTce (SEQ ID NO: 51) (0.603 g, 0.60 mmol) in a 200 ml short neck flask was dissolved in a 90% aqueous acetic acid solution (10 ml) and was mixed with zinc powder (2 g) with stirring. After completion of the reaction, the reaction mixture was filtered, was concentrated, and was mixed with a 10% aqueous citric acid solution to cause a precipitation. The precipitate was filtered off and was washed on a glass filter with water.

Yield: 0.380 g (72%), $[\alpha]_D^{20}$=−23.0° (c=0.1, DMF), melting point: 139 to 141° C.

Mass Spectrometry (ESI Method): m/e=m/e=896.4 ([M+Na]$^+$), 912.4 ([M+K]$^+$)

$^1$H-NMR (DMSO-d$_6$, 300 MHz): 8.45, 8.10, 8.01, 6.98 (7H; NH); 7.33, 7.30 (10H, Glu OBzl; Ser Bzl); 5.06 (2H, Glu OBzl —CH$_2$—); 4.49, 4.36, 4.24, 3.73, 3.61 (8H, αCH); 4.47 (2H, Ser Bzl —CH$_2$—); 4.18 (2H, Acm —CH$_2$—); 3.61 (2H, Ser βCH$_2$); 2.91, 2.67 (2H, Cys βCH$_2$); 2.40 (2H, Glu γCH$_2$); 2.05, 1.89 (2H, Glu βCH$_2$); 1.83 (3H, Acm —CH$_3$); 1.37 (9H, Boc t-Bu); 1.19, 1.12 (3H, Ala βCH$_3$).

(16b: Synthesis of Boc-Cys(Acm)-Gly-Gly-Ala-Ser(Bzl)-Glu(OBzl)-Phe-Tyr(Cl$_2$-Bzl)-Asn-Ser(Bzl)-Glu(OBzl)-Asn-Lys(Cl-Z)-Thr(Bzl)-Tyr(Cl$_2$-Bzl)-Asp(OBzl)-Leu-Asp(OBzl)-Phe-Lys(Cl-Z)-Thr(Bzl)-Pro-Asn-Asn-Asp(OBzl)-Gly-OTc) (SEQ ID NO: 62)

TFA.H-Glu(OBzl)-Phe-Tyr(Cl$_2$-Bzl)-Asn-Ser(Bzl)-Glu(OBzl)-Asn-Lys(Cl-Z)-Thr(Bzl) -Tyr(Cl$_2$-Bzl)-Asp (OBzl)-Leu-Asp(OBzl)-Phe-Lys(Cl-Z)-Thr(Bzl)-Pro-Asn-Asn-Asp(OBzl)-Gl y-OTce (SEQ ID NO: 64) (0.59 g, 0.13 mmol) in a flask was dissolved in DMF and was mixed with Boc-Cys(Acm)-Gly-Gly-Ala-Ser(Bzl)-Glu(OBzl)-OH (SEQ ID NO: 63) (0.157 g, 0.18 mmol), DIEA(77.0 ml, 0.45 mmol), and HATU(69.0 mg, 0.18 mmol). After completion of the reaction, the reaction mixture was concentrated, followed by addition of a saturated aqueous NaHCO$_3$ solution to cause a precipitation. The precipitate was filtered, placed on a glass filter, and was sequentially washed with a saturated aqueous NaHCO$_3$ solution, water, a 10% aqueous citric acid solution, and water. The precipitate was purified by gel filtration column chromatography (Sephadex LH60, DMF).

Yield: 0.48 g (69%)

Example 17

(17) Synthesis of H-Cys(Acm)-Gly-Gly-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Gly-OH (SEQ ID NO: 48) by Final Deprotection Reaction 17a: Synthesis of Boc-Cys(Acm)-Gly-Gly-Ala-Ser(Bzl)-Glu(OBzl)-Phe-Tyr(Cl$_2$-Bzl)-Asn-Ser(Bzl)-Glu(OBzl)-Asn-Lys(Cl-Z)-Thr(Bzl)-Tr(Cl$_2$-Bzl)-Asp(OBzl)-Le u-Asp(OBzl)-Phe-Lys(Cl-Z)-Thr(Bzl)-Pro-Asn-Asn-Asp(OBzl)-Gly-OH (SEQ ID NO: 65)

Boc-Cys(Acm)-Gly-Gly-Ala-Ser(Bzl)-Glu(OBzl)-Phe-Tyr(Cl$_2$-Bzl)-Asn-Ser(B)-Glu(O Bzl)-Asn-Lys(Cl-Z)-Thr(Bzl)-Tyr(Cl$_2$-Bzl)-Asp(OBzl)-Leu-Asp(OBzl)-Phe-Lys(Cl-Z)-Thr(Bzl) -Pro-Asn-Asn-Asp(OBzl)-Gly-OTce (SEQ ID NO: 62) (0.48 g, 0.10 mmol) in a flask was dissolved in DMF (7 ml) and was mixed with CH$_3$COOH (3 ml). After addition of Zn powder (1.0 g), the reaction mixture was stirred at room temperature for 1 hour. After completion of the reaction, the reaction mixture was filtered. The filtrate was concentrated, followed by addition of a 10% aqueous citric acid solution to cause a precipitation. The precipitate was placed on a glass filter and was washed with ion exchange water.

Yield: 298 mg (62%)

Figure 6:
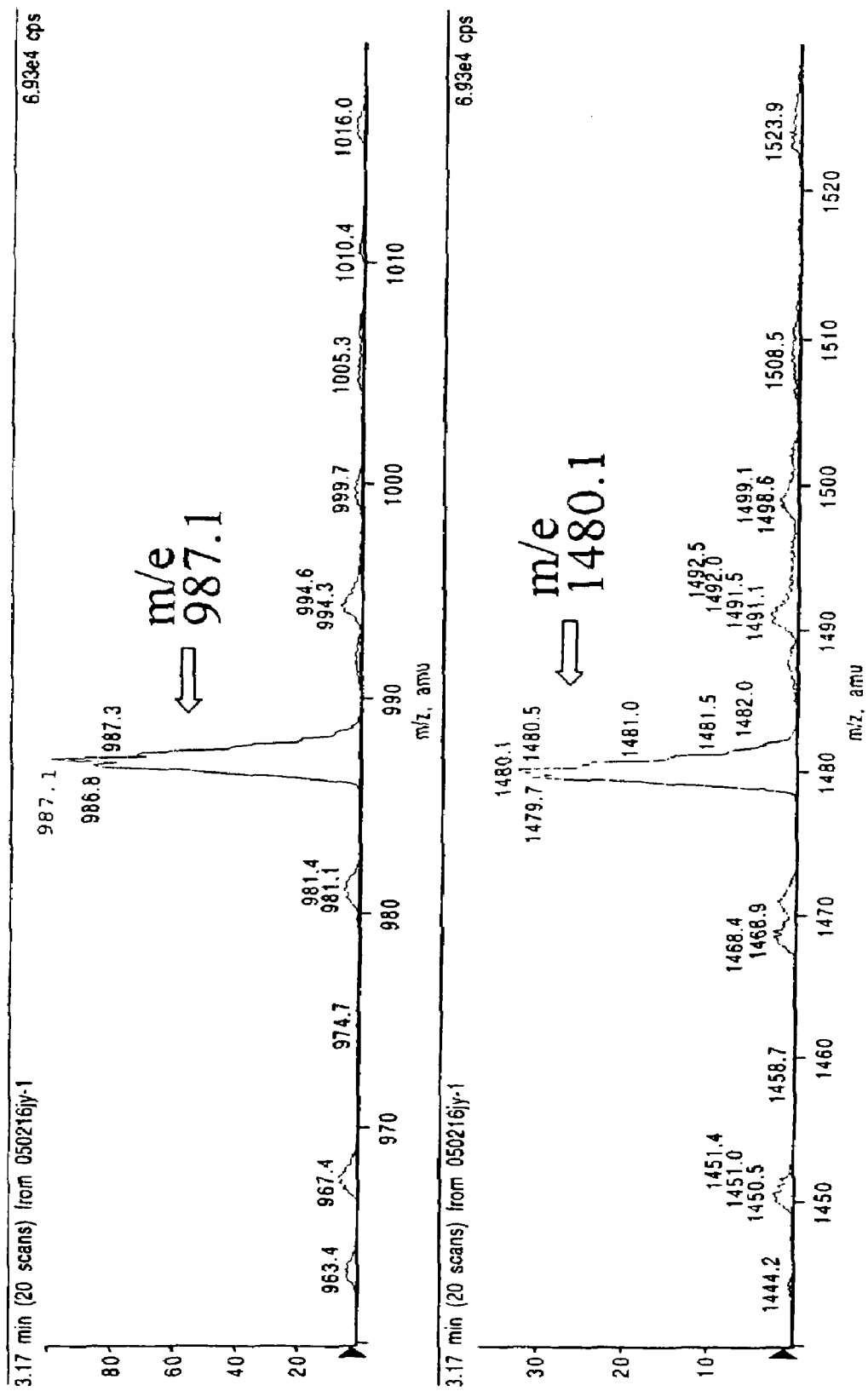
FIG. 6 shows spectral data (mass range m/e of 860 to 1020 and mass range m/e of 1440 to 1530) of the synthesis product by mass spectrometry according to the ESI method, with regard to the peptide compound H-Cys(Acm)-Gly-Gly-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Gly-OH (SEQ ID NO: 48) as one example of the present invention.

(17b: Synthesis of H-Cys(Acm)-Gly-Gly-Ala-Ser-
Glu-Phe-Tyr-Asn-Ser-Glu-Asn-Lys-Thr-Tyr-Asp-
Leu-Asp-Phe-Lys-Thr-Pro-Asn-Asn-Asp-Gly-OH)
(SEQ ID NO: 48) by Final Deprotection Reaction In a flask in ice bath, m-cresol (0.33 ml, 3.2 mmol), thioanisole (0.37 ml, 3.2 mmol), TFA (0.94 ml), and TFMSA (0.352 ml, 3.2 mmol) were sequentially added. After addition of Boc-Cys(Acm)-Gly-Gly-Ala-Ser(Bzl)-Glu(OBzl)-Phe-Tyr(Cl$_2$-Bzl)-Asn-Ser(Bzl)-Glu(OBzl)-A sn-Lys(Cl-Z)-Thr (Bzl)-Tyr(Cl$_2$-Bzl)-Asp(OBzl)-Leu-Asp(OBzl)-Phe-Lys (Cl-Z)-Thr(Bzl)-Pro-Asn-Asn-Asp(OBzl)-Gly-OH (SEQ ID NO: 65) (298 mg, 64 mmol), the reaction mixture was stood still. After 2 hours, the reaction mixture was mixed with distilled Et$_2$O to remove the supernatant (three times). After drying, it was purified by gel filtration column chromatography (Sephadex LH60, DMF). The resulting product was identified by mass spectrometry. FIG. 6 shows spectral data.

Yield: 150 mg (77%), melting point: 197° C.

Mass Spectrometry (ESI Method): m/e=1480.1 ([M+2H]$^{2+}$), 987.1 ([M+3H]$^{3+}$)

Example 18

(18) Diagnosis of *Plasmodium falciparum* Malaria
Patient by Fluorescent ELISA Method with H-Glu-
Glu-Glu-Glu-Ala-Ser-Glu-Phe-Tyr-Asn-Ser-Glu-
Asn-Lys-Thr-Tyr-Asp-Leu-Asp-Phe-Lys-Thr-Pro-
Asn-Asn-Asp-Gly-Gly-OH (SEQ ID NO: 13)

An antigen solution was prepared by dissolving 500 μg of the peptide compound (SEQ ID NO: 13) synthesized in Example 10 in 100 μl of dimethyl sulfoxide and by subsequently adding 1900 μl of a 0.05 M carbonate buffer (pH 9.6). The prepared antigen solution was dispensed by 70 μl in each of 98 wells on a plastic plate for fixation of the peptide compound.

The sera collected from *Plasmodium falciparum* malaria patients under informed consent at hospitals in Japan were used as subject sera, and the sera collected from non-infected individuals under informed consent in Japan were used as control sera. The subject sera and the control sera were individually added to the wells on the plastic plate to allow the antibodies existing in the respective sera to react with the peptide compound (SEQ ID NO: 13).

After removal of the serum, an enzyme-labeled secondary antibody against human immunoglobulin was added to each well for the immunological reaction. The enzyme bound to each well was made to react with a fluorescent substrate solution (4-methylumbelliferyl phosphate solution diluted to 200 μl with 0.1 M tris-HCL buffer). Micro Elisa autoreader (manufactured by Dynatech Laboratory Inc.) was used for the measurement. The measured antibody levels were expressed by relative fluorescence unit (RFU values).

Figure 7:
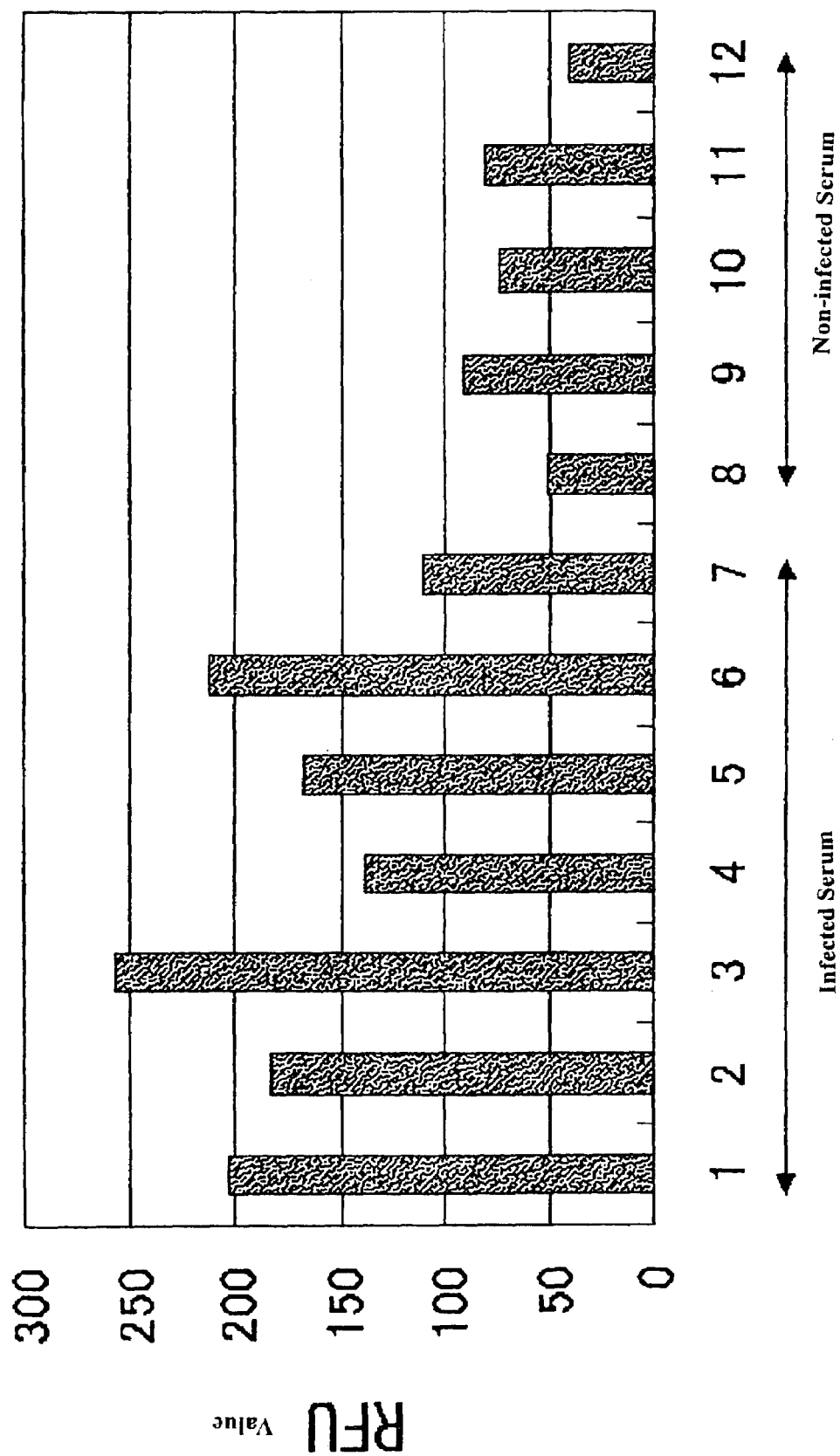
FIG. 7 is a graph showing antibody levels (RFU values) of sera (1-7) from *Plasmodium falciparum*-infected patients and those of sera (8-12) from non-infected individuals (for the purpose of comparison) measured by the fluorescent ELISA method with the synthesized peptide compound H-Glu-Glu-Glu-Glu-Ala-Ser-Glu-Phe-Tyr-Asn-Ser-Glu-Asn-Lys-Thr-Tyr-Asp-Leu-Asp-Phe-Lys-Thr-Pro-Asn-Asn-Asp-Gly-Gly-OH (SEQ ID NO: 13) as one example of the present invention.

FIG. 7 is a graph showing antibody levels of sera (1-7) from *Plasmodium falciparum*-infected patients and those of sera (8-12) from non-infected individuals (for the purpose of comparison) measured by the fluorescent ELISA method with the synthesized peptide compound (SEQ ID NO: 13). The result of this experiment shows that the average antibody level (181) of the malaria patients is significantly greater than the average antibody level (67) of the non-infected individuals. This proves that the peptide compound (SEQ ID NO: 13) synthesized in the example is effectively used for immunological diagnosis.

INDUSTRIAL APPLICABILITY

The peptide production method of the present invention enables synthesis of the partial peptide of enolase from *Plasmodium falciparum*. The peptide compound obtained by the method of the present invention has the ability of inducing an immunological response to *Plasmodium falciparum* by taking advantage of an immunological reaction in human or another animal. The peptide compound obtained by the method of the present invention is applicable as a diagnostic agent of the immunological state of malaria infection and as an immunological antigen peptide of inhibiting the proliferation of *Plasmodium falciparum*.

It will be apparent to those skilled in the art that various modifications and variations can be made in the present invention and specific examples provided herein without departing from the spirit or scope of the invention. Thus, it is intended that the present invention covers the modifications and variations of this invention that come within the scope of any claims and their equivalents.

The invention claimed is:

1. A method for producing a peptide having an amino acid sequence of Xaa Ala Ser Glu Phe Tyr Asn Ser Glu Asn Lys Thr Tyr Asp Leu Asp Phe Lys Thr Pro Asn Asn Asp Xaa (SEQ ID NO: 1), comprising linking the following fragments (i) through (v) to produce said peptide:

(v) Asn-Asn-Asp-Xaa (SEQ ID NO: 2);
(iv) Asp-Phe-Lys-Thr-Pro (SEQ ID NO: 3);
(iii) Asn-Lys-Thr-Tyr-Asp-Leu (SEQ ID NO: 4);
(ii) Phe-Tyr-Asn-Ser-Glu (SEQ ID NO: 5); and
(i) Xaa-Ala-Ser-Glu (SEQ ID NO: 6), where 'Xaa' in (i) and (v) represents zero or any arbitrary number of amino acid residues.

2. The production method according to claim 1, wherein the peptide of SEQ ID NO: 1 is produced by linking the modified peptides (I) through (V) shown below and performing subsequent deprotection:

(V) Asn($R_{15}$)-Asn($R_{16}$)-Asp($R_{17}$)-Xaa (SEQ ID NO: 7) where $R_{15}$ and $R_{16}$ represent $(C_6H_5)_3C$— or no protecting group, and $R_{17}$ represents $C_6H_5CH_2$—O— or $(CH_3)_3C$—O—;

(IV) Asp($R_{12}$)-Phe-Lys($R_{13}$)-Thr($R_{14}$)-Pro (SEQ ID NO: 8) where $R_{12}$ represents $C_6H_5CH_2$— or $(CH_3)_3C$—, $R_{13}$ represents $(CH_3)_3C$—O—CO—, $C_6H_5CH_2$—O—CO—, 2-chlorobenzyloxycarbonyl- or 9-fluorenylmethoxycarbonyl-, and $R_{14}$ represents $C_6H_5CH_2$— or $(CH_3)_3C$—;

(III) Asn($R_7$)-Lys($R_8$)-Thr($R_9$)-Tyr($R_{10}$)-Asp($R_{11}$)-Leu (SEQ ID NO: 9) where $R_7$ represents $(C_6H_5)_3C$— or no protecting group, $R_8$ represents $(CH_3)_3C$—O—CO—, $C_6H_5CH_2$—O—CO—, 2-chlorobenzyloxycarbonyl- or 9-fluorenylmethoxycarbonyl-, $R_9$ represents $C_6H_5CH_2$— or $(CH_3)_3C$—, $R_{10}$ represents $C_6H_5$—$CH_2$—, $Cl_2$—$C_6H_3$—$CH_2$—, or $(CH_3)_3C$—, and $R_{11}$ represents $C_6H_5CH_2$— or $(CH_3)_3C$—;

(II) Phe-Tyr($R_3$)-Asn($R_4$)-Ser($R_5$)-Glu($R_6$) (SEQ ID NO: 10) where $R_3$ represents $C_6H_5$—$CH_2$—, $Cl_2$—$C_6H_3$—$CH_2$—, or $(CH_3)_3C$—, $R_4$ represents $(C_6H_5)_3C$— or no protecting group, $R_5$ represents $C_6H_5CH_2$— or $(CH_3)_3C$—, and $R_6$ represents $C_6H_5CH_2$—O— or $(CH_3)_3C$—O—; and (I) Xaa-Ala-Ser($R_1$)-Glu($R_2$) (SEQ ID NO: 11) where $R_1$ represents $C_6H_5CH_2$— or $(CH_3)_3C$—, and $R_2$ represents $C_6H_5CH_2$—O— or $(CH_3)_3C$—O—.

3. The production method according to claim 1, wherein said peptides are condensed by using at least one of a combination of 1-ethyl-3-(3-dimethylaminopropyl)carbodiimide and 1-hydroxybenzotriazole, a combination of 2-(1H-benzotriazol-1-yl)-1,1,3,3-tetramethyluronium hexafluorophosphate and 1-hydroxybenzotriazol, or O-(7-azabenzotriazol-1-yl)-1,1,3,3-tetramethyluronium hexafluorophosphate.

4. A method for producing a peptide of SEQ ID NO: 1 having a modification in its terminus, comprising:

producing the peptide of SEQ ID NO: 1 by the method according to claim 1, and adding at least one of a sugar chain sequence, a peptide, a protein, a polysaccharide, a metal complex, a polymer carrier, a gel, a film, latex particles, metal fine particles, and a plastic plate to an N terminus and/or a C terminus of the peptide of SEQ ID NO: 1.

5. A method for manufacturing a diagnostic agent for *Plasmodium falciparum* infection, comprising:

producing the peptide of SEQ ID NO: 1 by the method according to claim 1; and formulating the produced peptide of SEQ ID NO: 1 with a carrier.

6. A method of manufacturing a diagnostic agent for *Plasmodium falciparum* infection, comprising:

producing the terminal-modified peptide of SEQ ID NO: 1 by the method of claim 4; and formulating the terminal-modified peptide of SEQ ID NO: 1 with at least one pharmaceutically acceptable carrier.

7. N-α-t-butoxycarbonyl-L-glutamic-γ-benzyl-α-trichloroethyl ester that essentially consists of an L-form.

8. A method for producing a glutamic acid-containing peptide comprising a step of synthesizing a glutamic acid-containing peptide using the N-α-t-butoxycarbonyl-L-glutamic-γ-benzyl-α-trichloroethyl ester according to claim 7.

9. The production method according to claim 2, wherein said peptides are condensed by using at least one of a combination of 1-ethyl-3-(3-dimethylaminopropyl)carbodiimide and 1-hydroxybenzotriazole, a combination of 2-(1H-benzotriazol-1-yl)-1,1,3,3-tetramethyluronium hexafluorophosphate and 1-hydroxybenzotriazol, or O-(7-azabenzotriazol-1-yl)-1,1,3,3-tetramethyluronium hexafluorophosphate.

10. A method for producing a peptide of SEQ ID NO: 1 having a modification in its terminus, comprising:

producing the peptide of SEQ ID NO: 1 by the method according to claim 2, and adding at least one of a sugar chain sequence, a peptide, a protein, a polysaccharide, a metal complex, a polymer carrier, a gel, a film, latex particles, metal fine particles, and a plastic plate to an N terminus and/or a C terminus of the peptide of SEQ ID NO: 1.

11. A method for producing a peptide of SEQ ID NO: 1 having a modification in its terminus, comprising:

producing the peptide of SEQ ID NO: 1 by the method according to claim 3, and adding at least one of a sugar chain sequence, a peptide, a protein, a polysaccharide, a metal complex, a polymer carrier, a gel, a film, latex particles, metal fine particles, and a plastic plate to an N terminus and/or a C terminus of the peptide of SEQ ID NO: 1.

12. A method for producing a peptide of SEQ ID NO: 1 having a modification in its terminus, comprising:

producing the peptide of SEQ ID NO: 1 by the method according to claim 9, and adding at least one of a sugar chain sequence, a peptide, a protein, a polysaccharide, a metal complex, a polymer carrier, a gel, a film, latex particles, metal fine particles, and a plastic plate to an N terminus and/or a C terminus of the peptide of SEQ ID NO: 1.

13. A method for manufacturing a diagnostic agent for *Plasmodium falciparum* infection, comprising:

producing the peptide of SEQ ID NO: 1 by the method according to claim 2; and formulating the produced peptide of SEQ ID NO: 1 with a carrier.

14. A method for manufacturing a diagnostic agent for *Plasmodium falciparum* infection, comprising:

producing the peptide of SEQ ID NO: 1 by the method according to claim 3; and formulating the produced peptide of SEQ ID NO: 1 with a carrier.

15. A method for manufacturing a diagnostic agent for *Plasmodium falciparum* infection, comprising:

producing the peptide of SEQ ID NO: 1 by the method according to claim 9; and formulating the produced peptide of SEQ ID NO: 1 with a carrier.

16. A method of manufacturing a diagnostic agent for *Plasmodium falciparum* infection, comprising:

producing the terminal-modified peptide of SEQ ID NO: 1 by the method of claim 10; and formulating the terminal-modified peptide of SEQ ID NO: 1 with at least one pharmaceutically acceptable carrier.

17. A method of manufacturing a diagnostic agent for *Plasmodium falciparum* infection, comprising:

producing the terminal-modified peptide of SEQ ID NO: 1 by the method of claim 11; and formulating the terminal-modified peptide of SEQ ID NO: 1 with at least one pharmaceutically acceptable carrier.

18. A method of manufacturing a diagnostic agent for *Plasmodium falciparum* infection, comprising:

producing the terminal-modified peptide of SEQ ID NO: 1 by the method of claim 12; and formulating the terminal-modified peptide of SEQ ID NO: 1 with at least one pharmaceutically acceptable carrier.

* * * * *

SEQUENCE LISTING

```
<160> NUMBER OF SEQ ID NOS: 65

<210> SEQ ID NO 1
<211> LENGTH: 24
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = nothing, or one or more of amino acids of
      any kind
<220> FEATURE:
<221> NAME/KEY: MISC_FEATURE
<222> LOCATION: (24)
<223> OTHER INFORMATION: Xaa = nothing, or one or more of amino acids of
      any kind

<400> SEQUENCE: 1
```

```
Xaa Ala Ser Glu Phe Tyr Asn Ser Glu Asn Lys Thr Tyr Asp Leu Asp
1               5                   10                  15

Phe Lys Thr Pro Asn Asn Asp Xaa
            20

<210> SEQ ID NO 2
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (4)
<223> OTHER INFORMATION: Xaa = nothing, or one or more of amino acids of
      any kind

<400> SEQUENCE: 2

Asn Asn Asp Xaa
1

<210> SEQ ID NO 3
<211> LENGTH: 5
<212> TYPE: PRT
<213> ORGANISM: Artificial
<220> FEATURE:
<223> OTHER INFORMATION: artificial peptide

<400> SEQUENCE: 3

Asp Phe Lys Thr Pro
1               5

<210> SEQ ID NO 4
<211> LENGTH: 6
<212> TYPE: PRT
<213> ORGANISM: Artificial
<220> FEATURE:
<223> OTHER INFORMATION: artificial peptide

<400> SEQUENCE: 4

Asn Lys Thr Tyr Asp Leu
1               5

<210> SEQ ID NO 5
<211> LENGTH: 5
<212> TYPE: PRT
<213> ORGANISM: Artificial
<220> FEATURE:
<223> OTHER INFORMATION: artificial peptide

<400> SEQUENCE: 5

Phe Tyr Asn Ser Glu
1               5

<210> SEQ ID NO 6
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = nothing, or one or more of amino acids of
      any kind

<400> SEQUENCE: 6

Xaa Ala Ser Glu
```

-continued

```
<210> SEQ ID NO 7
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-beta-trityl-L-asparagine or
      L-asparagine
<220> FEATURE:
<221> NAME/KEY: MISC_FEATURE
<222> LOCATION: (2)
<223> OTHER INFORMATION: Xaa = N-beta-trityl-L-asparagine or
      L-asparagine
<220> FEATURE:
<221> NAME/KEY: MISC_FEATURE
<222> LOCATION: (3)
<223> OTHER INFORMATION: Xaa = L-aspartic acid beta-benzyl ester or
      L-aspartic acid beta-t-butyl ester
<220> FEATURE:
<221> NAME/KEY: MISC_FEATURE
<222> LOCATION: (4)
<223> OTHER INFORMATION: Xaa = nothing, or one or more of amino acids of
      any kind

<400> SEQUENCE: 7

Xaa Xaa Xaa Xaa
1

<210> SEQ ID NO 8
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = L-aspartic acid beta-benzyl ester or
      L-aspartic acid beta-t-butyl ester
<220> FEATURE:
<221> NAME/KEY: MISC_FEATURE
<222> LOCATION: (3)
<223> OTHER INFORMATION: Xaa = N-epsilon-tert-butoxycarbonyl-L-lysine,
      N-epsilon-benzyloxycarbonyl-L-lysine, N-epsilon-2-
      chlorobenzyloxycarbonyl-L-lysine, or N-epsilon-9-
      fluorenylmethoxycarbonyl-L-lysine
<220> FEATURE:
<221> NAME/KEY: MISC_FEATURE
<222> LOCATION: (4)
<223> OTHER INFORMATION: Xaa = O-benzyl-L-threonine or O-t-butyl-L-
      threonine

<400> SEQUENCE: 8

Xaa Phe Xaa Xaa Pro
1               5

<210> SEQ ID NO 9
<211> LENGTH: 6
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-beta-trityl-L-asparagine or
      L-asparagine
<220> FEATURE:
<221> NAME/KEY: MISC_FEATURE
```

```
<222> LOCATION: (2)
<223> OTHER INFORMATION: Xaa = N-epsilon-tert-butoxycarbonyl-L-lysine,
      N-epsilon-benzyloxycarbonyl-L-lysine, N-epsilon-2-
      chlorobenzyloxycarbonyl-L-lysine, or N-epsilon-9-
      fluorenylmethoxycarbonyl-L-lysine
<220> FEATURE:
<221> NAME/KEY: MISC_FEATURE
<222> LOCATION: (3)
<223> OTHER INFORMATION: Xaa = O-benzyl-L-threonine or O-t-butyl-L-
      threonine
<220> FEATURE:
<221> NAME/KEY: MISC_FEATURE
<222> LOCATION: (4)
<223> OTHER INFORMATION: Xaa = O-benzyl-L-tyrosine, O-2,6-
      dichlorobenzyl-L-tyrosine or O-t-butyl-L-tyrosine
<220> FEATURE:
<221> NAME/KEY: MISC_FEATURE
<222> LOCATION: (5)
<223> OTHER INFORMATION: Xaa = L-aspartic acid beta-benzyl ester or
      L-aspartic acid beta-t-butyl ester

<400> SEQUENCE: 9

Xaa Xaa Xaa Xaa Xaa Leu
1               5

<210> SEQ ID NO 10
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (2)
<223> OTHER INFORMATION: Xaa = O-benzyl-L-tyrosine, O-2,6-
      dichlorobenzyl-L-tyrosine or O-t-butyl-L-tyrosine
<220> FEATURE:
<221> NAME/KEY: MISC_FEATURE
<222> LOCATION: (3)
<223> OTHER INFORMATION: Xaa = N-beta-trityl-L-asparagine or
      L-asparagine
<220> FEATURE:
<221> NAME/KEY: MISC_FEATURE
<222> LOCATION: (4)
<223> OTHER INFORMATION: Xaa = O-benzyl-L-serine or O-t-butyl-L-serine
<220> FEATURE:
<221> NAME/KEY: MISC_FEATURE
<222> LOCATION: (5)
<223> OTHER INFORMATION: Xaa = L-glutamic acid gamma-benzyl ester or
      L-glutamic acid gamma-t-butyl ester

<400> SEQUENCE: 10

Phe Xaa Xaa Xaa Xaa
1               5

<210> SEQ ID NO 11
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = nothing, or one or more of amino acids of
      any kind
<220> FEATURE:
<221> NAME/KEY: MISC_FEATURE
<222> LOCATION: (3)
<223> OTHER INFORMATION: Xaa = O-benzyl-L-serine or O-t-butyl-L-serine
<220> FEATURE:
<221> NAME/KEY: MISC_FEATURE
<222> LOCATION: (4)
<223> OTHER INFORMATION: Xaa = L-glutamic acid gamma-benzyl ester or
      L-glutamic acid gamma-t-butyl ester
```

```
<400> SEQUENCE: 11

Xaa Ala Xaa Xaa
1

<210> SEQ ID NO 12
<211> LENGTH: 22
<212> TYPE: PRT
<213> ORGANISM: Artificial
<220> FEATURE:
<223> OTHER INFORMATION: artificial peptide

<400> SEQUENCE: 12

Ala Ser Glu Phe Tyr Asn Ser Glu Asn Lys Thr Tyr Asp Leu Asp Phe
1               5                   10                  15

Lys Thr Pro Asn Asn Asp
            20

<210> SEQ ID NO 13
<211> LENGTH: 28
<212> TYPE: PRT
<213> ORGANISM: Artificial
<220> FEATURE:
<223> OTHER INFORMATION: artificial peptide

<400> SEQUENCE: 13

Glu Glu Glu Glu Ala Ser Glu Phe Tyr Asn Ser Glu Asn Lys Thr Tyr
1               5                   10                  15

Asp Leu Asp Phe Lys Thr Pro Asn Asn Asp Gly Gly
            20                  25

<210> SEQ ID NO 14
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-asparagine
<220> FEATURE:
<221> NAME/KEY: MISC_FEATURE
<222> LOCATION: (3)
<223> OTHER INFORMATION: Xaa = L-aspartic acid beta-benzyl ester
<220> FEATURE:
<221> NAME/KEY: MISC_FEATURE
<222> LOCATION: (5)
<223> OTHER INFORMATION: Xaa = glycine alpha-benzyl ester

<400> SEQUENCE: 14

Xaa Asn Xaa Gly Xaa
1               5

<210> SEQ ID NO 15
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-asparagine
<220> FEATURE:
<221> NAME/KEY: MISC_FEATURE
<222> LOCATION: (2)
<223> OTHER INFORMATION: Xaa = L-aspartic acid beta-benzyl ester
<220> FEATURE:
```

```
<221> NAME/KEY: MISC_FEATURE
<222> LOCATION: (4)
<223> OTHER INFORMATION: Xaa = glycine alpha-benzyl ester

<400> SEQUENCE: 15

Xaa Xaa Gly Xaa
1

<210> SEQ ID NO 16
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (2)
<223> OTHER INFORMATION: Xaa = L-aspartic acid beta-benzyl ester
<220> FEATURE:
<221> NAME/KEY: MISC_FEATURE
<222> LOCATION: (4)
<223> OTHER INFORMATION: Xaa = glycine alpha-benzyl ester

<400> SEQUENCE: 16

Asn Xaa Gly Xaa
1

<210> SEQ ID NO 17
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-aspartic acid
      O-benzyl ester
<220> FEATURE:
<221> NAME/KEY: MISC_FEATURE
<222> LOCATION: (3)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (4)
<223> OTHER INFORMATION: Xaa = O-benzyl-L-threonine
<220> FEATURE:
<221> NAME/KEY: MISC_FEATURE
<222> LOCATION: (5)
<223> OTHER INFORMATION: Xaa = L-proline alpha-trichloroethyl ester

<400> SEQUENCE: 17

Xaa Phe Xaa Xaa Xaa
1               5

<210> SEQ ID NO 18
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-phenylalanine
<220> FEATURE:
<221> NAME/KEY: MISC_FEATURE
<222> LOCATION: (2)
<223> OTHER INFORMATION: Xaa = N-epsilon-2-chlorobenzyloxycarbonyl-L-
      lysine
<220> FEATURE:
<221> NAME/KEY: MISC_FEATURE
```

```
<222> LOCATION: (3)
<223> OTHER INFORMATION: Xaa = O-benzyl-L-threonine
<220> FEATURE:
<221> NAME/KEY: MISC_FEATURE
<222> LOCATION: (4)
<223> OTHER INFORMATION: Xaa = L-proline alpha-trichloroethyl ester

<400> SEQUENCE: 18

Xaa Xaa Xaa Xaa
1

<210> SEQ ID NO 19
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (2)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (3)
<223> OTHER INFORMATION: Xaa = O-benzyl-L-threonine
<220> FEATURE:
<221> NAME/KEY: MISC_FEATURE
<222> LOCATION: (4)
<223> OTHER INFORMATION: Xaa = L-proline alpha-trichloroethyl ester

<400> SEQUENCE: 19

Phe Xaa Xaa Xaa
1

<210> SEQ ID NO 20
<211> LENGTH: 6
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-asparagine
<220> FEATURE:
<221> NAME/KEY: MISC_FEATURE
<222> LOCATION: (2)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (3)
<223> OTHER INFORMATION: Xaa = O-benzyl-L-threonine
<220> FEATURE:
<221> NAME/KEY: MISC_FEATURE
<222> LOCATION: (4)
<223> OTHER INFORMATION: Xaa = O-2,6-dichlorobenzyl-L-tyrosine
<220> FEATURE:
<221> NAME/KEY: MISC_FEATURE
<222> LOCATION: (5)
<223> OTHER INFORMATION: Xaa = L-aspartic acid beta-benzyl ester
<220> FEATURE:
<221> NAME/KEY: MISC_FEATURE
<222> LOCATION: (6)
<223> OTHER INFORMATION: Xaa = L-leucine alpha-trichloroethyl ester

<400> SEQUENCE: 20

Xaa Xaa Xaa Xaa Xaa Xaa
1               5

<210> SEQ ID NO 21
<211> LENGTH: 4
```

```
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-O-benzyl-L-
      threonine
<220> FEATURE:
<221> NAME/KEY: MISC_FEATURE
<222> LOCATION: (2)
<223> OTHER INFORMATION: Xaa = O-2,6-dichlorobenzyl-L-tyrosine
<220> FEATURE:
<221> NAME/KEY: MISC_FEATURE
<222> LOCATION: (3)
<223> OTHER INFORMATION: Xaa = L-aspartic acid beta-benzyl ester
<220> FEATURE:
<221> NAME/KEY: MISC_FEATURE
<222> LOCATION: (4)
<223> OTHER INFORMATION: Xaa = L-leucine alpha-trichloroethyl ester

<400> SEQUENCE: 21

Xaa Xaa Xaa Xaa
1

<210> SEQ ID NO 22
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-N-epsilon-2-
      chlorobenzyloxycarbonyl-L-lysine
<220> FEATURE:
<221> NAME/KEY: MISC_FEATURE
<222> LOCATION: (2)
<223> OTHER INFORMATION: Xaa = O-benzyl-L-threonine
<220> FEATURE:
<221> NAME/KEY: MISC_FEATURE
<222> LOCATION: (3)
<223> OTHER INFORMATION: Xaa = O-2,6-dichlorobenzyl-L-tyrosine
<220> FEATURE:
<221> NAME/KEY: MISC_FEATURE
<222> LOCATION: (4)
<223> OTHER INFORMATION: Xaa = L-aspartic acid beta-benzyl ester
<220> FEATURE:
<221> NAME/KEY: MISC_FEATURE
<222> LOCATION: (5)
<223> OTHER INFORMATION: Xaa = L-leucine alpha-trichloroethyl ester

<400> SEQUENCE: 22

Xaa Xaa Xaa Xaa Xaa
1               5

<210> SEQ ID NO 23
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = O-benzyl-L-threonine
<220> FEATURE:
<221> NAME/KEY: MISC_FEATURE
<222> LOCATION: (2)
<223> OTHER INFORMATION: Xaa = O-2,6-dichlorobenzyl-L-tyrosine
<220> FEATURE:
<221> NAME/KEY: MISC_FEATURE
<222> LOCATION: (3)
```

```
<223> OTHER INFORMATION: Xaa = L-aspartic acid beta-benzyl ester
<220> FEATURE:
<221> NAME/KEY: MISC_FEATURE
<222> LOCATION: (4)
<223> OTHER INFORMATION: Xaa = L-leucine alpha-trichloroethyl ester

<400> SEQUENCE: 23

Xaa Xaa Xaa Xaa
1

<210> SEQ ID NO 24
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (2)
<223> OTHER INFORMATION: Xaa = O-benzyl-L-threonine
<220> FEATURE:
<221> NAME/KEY: MISC_FEATURE
<222> LOCATION: (3)
<223> OTHER INFORMATION: Xaa = O-2,6-dichlorobenzyl-L-tyrosine
<220> FEATURE:
<221> NAME/KEY: MISC_FEATURE
<222> LOCATION: (4)
<223> OTHER INFORMATION: Xaa = L-aspartic acid beta-benzyl ester
<220> FEATURE:
<221> NAME/KEY: MISC_FEATURE
<222> LOCATION: (5)
<223> OTHER INFORMATION: Xaa = L-leucine alpha-trichloroethyl ester

<400> SEQUENCE: 24

Xaa Xaa Xaa Xaa Xaa
1               5

<210> SEQ ID NO 25
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-phenylalanine
<220> FEATURE:
<221> NAME/KEY: MISC_FEATURE
<222> LOCATION: (2)
<223> OTHER INFORMATION: Xaa = O-2,6-dichlorobenzyl-L-tyrosine
<220> FEATURE:
<221> NAME/KEY: MISC_FEATURE
<222> LOCATION: (4)
<223> OTHER INFORMATION: Xaa = O-benzyl-L-serine
<220> FEATURE:
<221> NAME/KEY: MISC_FEATURE
<222> LOCATION: (5)
<223> OTHER INFORMATION: Xaa = L-glutamic acid gamma-benzyl ester alpha-
      trichloroethyl ester

<400> SEQUENCE: 25

Xaa Xaa Asn Xaa Xaa
1               5

<210> SEQ ID NO 26
<211> LENGTH: 4
<212> TYPE: PRT
```

```
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-O-2,6-
      dichlorobenzyl-L-tyrosine
<220> FEATURE:
<221> NAME/KEY: MISC_FEATURE
<222> LOCATION: (3)
<223> OTHER INFORMATION: Xaa = O-benzyl-L-serine
<220> FEATURE:
<221> NAME/KEY: MISC_FEATURE
<222> LOCATION: (4)
<223> OTHER INFORMATION: Xaa = L-glutamic acid gamma-benzyl ester alpha-
      trichloroethyl ester

<400> SEQUENCE: 26

Xaa Asn Xaa Xaa
1

<210> SEQ ID NO 27
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = O-2,6-dichlorobenzyl-L-tyrosine
<220> FEATURE:
<221> NAME/KEY: MISC_FEATURE
<222> LOCATION: (3)
<223> OTHER INFORMATION: Xaa = O-benzyl-L-serine
<220> FEATURE:
<221> NAME/KEY: MISC_FEATURE
<222> LOCATION: (4)
<223> OTHER INFORMATION: Xaa = L-glutamic acid gamma-benzyl ester alpha-
      trichloroethyl ester

<400> SEQUENCE: 27

Xaa Asn Xaa Xaa
1

<210> SEQ ID NO 28
<211> LENGTH: 7
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-glutamic acid
      gamma-benzyl ester
<220> FEATURE:
<221> NAME/KEY: MISC_FEATURE
<222> LOCATION: (2)
<223> OTHER INFORMATION: Xaa = L-glutamic acid gamma-benzyl ester
<220> FEATURE:
<221> NAME/KEY: MISC_FEATURE
<222> LOCATION: (3)
<223> OTHER INFORMATION: Xaa = -L-glutamic acid gamma-benzyl ester
<220> FEATURE:
<221> NAME/KEY: MISC_FEATURE
<222> LOCATION: (4)
<223> OTHER INFORMATION: Xaa = -L-glutamic acid gamma-benzyl ester
<220> FEATURE:
<221> NAME/KEY: MISC_FEATURE
<222> LOCATION: (6)
<223> OTHER INFORMATION: Xaa = O-benzyl-L-serine
<220> FEATURE:
<221> NAME/KEY: MISC_FEATURE
```

```
<222> LOCATION: (7)
<223> OTHER INFORMATION: Xaa = L-glutamic acid gamma-benzyl ester alpha-
      trichloroethyl ester

<400> SEQUENCE: 28

Xaa Xaa Xaa Xaa Ala Xaa Xaa
1               5

<210> SEQ ID NO 29
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-glutamic acid
      gamma-benzyl ester
<220> FEATURE:
<221> NAME/KEY: MISC_FEATURE
<222> LOCATION: (3)
<223> OTHER INFORMATION: Xaa = O-benzyl-L-serine
<220> FEATURE:
<221> NAME/KEY: MISC_FEATURE
<222> LOCATION: (4)
<223> OTHER INFORMATION: Xaa = L-glutamic acid gamma-benzyl ester alpha-
      trichloroethyl ester

<400> SEQUENCE: 29

Xaa Ala Xaa Xaa
1

<210> SEQ ID NO 30
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-glutamic acid
      gamma-benzyl ester
<220> FEATURE:
<221> NAME/KEY: MISC_FEATURE
<222> LOCATION: (2)
<223> OTHER INFORMATION: Xaa = -L-glutamic acid gamma-benzyl ester
<220> FEATURE:
<221> NAME/KEY: MISC_FEATURE
<222> LOCATION: (4)
<223> OTHER INFORMATION: Xaa = O-benzyl-L-serine
<220> FEATURE:
<221> NAME/KEY: MISC_FEATURE
<222> LOCATION: (5)
<223> OTHER INFORMATION: Xaa = L-glutamic acid gamma-benzyl ester alpha-
      trichloroethyl ester

<400> SEQUENCE: 30

Xaa Xaa Ala Xaa Xaa
1               5

<210> SEQ ID NO 31
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = L-glutamic acid gamma-benzyl ester
<220> FEATURE:
```

```
<221> NAME/KEY: MISC_FEATURE
<222> LOCATION: (3)
<223> OTHER INFORMATION: Xaa = O-benzyl-L-serine
<220> FEATURE:
<221> NAME/KEY: MISC_FEATURE
<222> LOCATION: (4)
<223> OTHER INFORMATION: Xaa = L-glutamic acid gamma-benzyl ester alpha-
      trichloroethyl ester

<400> SEQUENCE: 31

Xaa Ala Xaa Xaa
1

<210> SEQ ID NO 32
<211> LENGTH: 6
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-glutamic acid
      gamma-benzyl ester
<220> FEATURE:
<221> NAME/KEY: MISC_FEATURE
<222> LOCATION: (2)..(3)
<223> OTHER INFORMATION: Xaa = -L-glutamic acid gamma-benzyl ester
<220> FEATURE:
<221> NAME/KEY: MISC_FEATURE
<222> LOCATION: (5)
<223> OTHER INFORMATION: Xaa = O-benzyl-L-serine
<220> FEATURE:
<221> NAME/KEY: MISC_FEATURE
<222> LOCATION: (6)
<223> OTHER INFORMATION: Xaa = L-glutamic acid gamma-benzyl ester alpha-
      trichloroethyl ester

<400> SEQUENCE: 32

Xaa Xaa Xaa Ala Xaa Xaa
1               5

<210> SEQ ID NO 33
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)..(2)
<223> OTHER INFORMATION: Xaa = L-glutamic acid gamma-benzyl ester
<220> FEATURE:
<221> NAME/KEY: MISC_FEATURE
<222> LOCATION: (4)
<223> OTHER INFORMATION: Xaa = O-benzyl-L-serine
<220> FEATURE:
<221> NAME/KEY: MISC_FEATURE
<222> LOCATION: (5)
<223> OTHER INFORMATION: Xaa = L-glutamic acid gamma-benzyl ester alpha-
      trichloroethyl ester

<400> SEQUENCE: 33

Xaa Xaa Ala Xaa Xaa
1               5

<210> SEQ ID NO 34
<211> LENGTH: 6
<212> TYPE: PRT
<213> ORGANISM: Artificial
<220> FEATURE:
<223> OTHER INFORMATION: artificial peptide
<220> FEATURE:
```

```
<221> NAME/KEY: MISC_FEATURE
<222> LOCATION: (1)..(3)
<223> OTHER INFORMATION: Xaa = L-glutamic acid gamma-benzyl ester
<220> FEATURE:
<221> NAME/KEY: MISC_FEATURE
<222> LOCATION: (5)
<223> OTHER INFORMATION: Xaa = O-benzyl-L-serine
<220> FEATURE:
<221> NAME/KEY: MISC_FEATURE
<222> LOCATION: (6)
<223> OTHER INFORMATION: Xaa = L-glutamic acid gamma-benzyl ester alpha-
      trichloroethyl ester

<400> SEQUENCE: 34

Xaa Xaa Xaa Ala Xaa Xaa
1               5

<210> SEQ ID NO 35
<211> LENGTH: 10
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-aspartic acid
      O-benzyl ester
<220> FEATURE:
<221> NAME/KEY: MISC_FEATURE
<222> LOCATION: (3)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (4)
<223> OTHER INFORMATION: Xaa = O-benzyl-L-threonine
<220> FEATURE:
<221> NAME/KEY: MISC_FEATURE
<222> LOCATION: (8)
<223> OTHER INFORMATION: Xaa = L-aspartic acid beta-benzyl ester
<220> FEATURE:
<221> NAME/KEY: MISC_FEATURE
<222> LOCATION: (10)
<223> OTHER INFORMATION: Xaa = glycine alpha-benzyl ester

<400> SEQUENCE: 35

Xaa Phe Xaa Xaa Pro Asn Asn Xaa Gly Xaa
1               5                   10

<210> SEQ ID NO 36
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-aspartic acid
      O-benzyl ester
<220> FEATURE:
<221> NAME/KEY: MISC_FEATURE
<222> LOCATION: (3)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (4)
<223> OTHER INFORMATION: Xaa = O-benzyl-L-threonine

<400> SEQUENCE: 36

Xaa Phe Xaa Xaa Pro
1               5
```

<210> SEQ ID NO 37
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (3)
<223> OTHER INFORMATION: Xaa = L-aspartic acid beta-benzyl ester
<220> FEATURE:
<221> NAME/KEY: MISC_FEATURE
<222> LOCATION: (5)
<223> OTHER INFORMATION: Xaa = glycine alpha-benzyl ester

<400> SEQUENCE: 37

Asn Asn Xaa Gly Xaa
1               5

<210> SEQ ID NO 38
<211> LENGTH: 16
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-asparagine
<220> FEATURE:
<221> NAME/KEY: MISC_FEATURE
<222> LOCATION: (2)
<223> OTHER INFORMATION: Xaa = N-epsilon-2-chlorobenzyloxycarbonyl-L-
    lysine
<220> FEATURE:
<221> NAME/KEY: MISC_FEATURE
<222> LOCATION: (3)
<223> OTHER INFORMATION: Xaa = O-benzyl-L-threonine
<220> FEATURE:
<221> NAME/KEY: MISC_FEATURE
<222> LOCATION: (4)
<223> OTHER INFORMATION: Xaa = O-2,6-dichlorobenzyl-L-tyrosine
<220> FEATURE:
<221> NAME/KEY: MISC_FEATURE
<222> LOCATION: (5)
<223> OTHER INFORMATION: Xaa = L-aspartic acid beta-benzyl ester
<220> FEATURE:
<221> NAME/KEY: MISC_FEATURE
<222> LOCATION: (7)
<223> OTHER INFORMATION: Xaa = L-aspartic acid beta-benzyl ester
<220> FEATURE:
<221> NAME/KEY: MISC_FEATURE
<222> LOCATION: (9)
<223> OTHER INFORMATION: Xaa = N-epsilon-2-chlorobenzyloxycarbonyl-L-
    lysine
<220> FEATURE:
<221> NAME/KEY: MISC_FEATURE
<222> LOCATION: (10)
<223> OTHER INFORMATION: Xaa = O-benzyl-L-threonine
<220> FEATURE:
<221> NAME/KEY: MISC_FEATURE
<222> LOCATION: (14)
<223> OTHER INFORMATION: Xaa = L-aspartic acid beta-benzyl ester
<220> FEATURE:
<221> NAME/KEY: MISC_FEATURE
<222> LOCATION: (16)
<223> OTHER INFORMATION: Xaa = glycine alpha-benzyl ester

<400> SEQUENCE: 38

Xaa Xaa Xaa Xaa Xaa Leu Xaa Phe Xaa Xaa Pro Asn Asn Xaa Gly Xaa
1               5                   10                  15

<210> SEQ ID NO 39

```
<211> LENGTH: 6
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-asparagine
<220> FEATURE:
<221> NAME/KEY: MISC_FEATURE
<222> LOCATION: (2)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (3)
<223> OTHER INFORMATION: Xaa = O-benzyl-L-threonine
<220> FEATURE:
<221> NAME/KEY: MISC_FEATURE
<222> LOCATION: (4)
<223> OTHER INFORMATION: Xaa = O-2,6-dichlorobenzyl-L-tyrosine
<220> FEATURE:
<221> NAME/KEY: MISC_FEATURE
<222> LOCATION: (5)
<223> OTHER INFORMATION: Xaa = L-aspartic acid beta-benzyl ester

<400> SEQUENCE: 39

Xaa Xaa Xaa Xaa Xaa Leu
1               5

<210> SEQ ID NO 40
<211> LENGTH: 10
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = L-aspartic acid beta-benzyl ester
<220> FEATURE:
<221> NAME/KEY: MISC_FEATURE
<222> LOCATION: (3)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (4)
<223> OTHER INFORMATION: Xaa = O-benzyl-L-threonine
<220> FEATURE:
<221> NAME/KEY: MISC_FEATURE
<222> LOCATION: (8)
<223> OTHER INFORMATION: Xaa = L-aspartic acid beta-benzyl ester
<220> FEATURE:
<221> NAME/KEY: MISC_FEATURE
<222> LOCATION: (10)
<223> OTHER INFORMATION: Xaa = glycine alpha-benzyl ester

<400> SEQUENCE: 40

Xaa Phe Xaa Xaa Pro Asn Asn Xaa Gly Xaa
1               5                   10

<210> SEQ ID NO 41
<211> LENGTH: 21
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-phenylalanine
<220> FEATURE:
<221> NAME/KEY: MISC_FEATURE
```

```
<222> LOCATION: (2)
<223> OTHER INFORMATION: Xaa = O-2,6-dichlorobenzyl-L-tyrosine
<220> FEATURE:
<221> NAME/KEY: MISC_FEATURE
<222> LOCATION: (4)
<223> OTHER INFORMATION: Xaa = O-benzyl-L-serine
<220> FEATURE:
<221> NAME/KEY: MISC_FEATURE
<222> LOCATION: (5)
<223> OTHER INFORMATION: Xaa = -L-glutamic acid gamma-benzyl ester
<220> FEATURE:
<221> NAME/KEY: MISC_FEATURE
<222> LOCATION: (7)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (8)
<223> OTHER INFORMATION: Xaa = O-benzyl-L-threonine
<220> FEATURE:
<221> NAME/KEY: MISC_FEATURE
<222> LOCATION: (9)
<223> OTHER INFORMATION: Xaa = O-2,6-dichlorobenzyl-L-tyrosine
<220> FEATURE:
<221> NAME/KEY: MISC_FEATURE
<222> LOCATION: (10)
<223> OTHER INFORMATION: Xaa = L-aspartic acid beta-benzyl ester
<220> FEATURE:
<221> NAME/KEY: MISC_FEATURE
<222> LOCATION: (12)
<223> OTHER INFORMATION: Xaa = L-aspartic acid beta-benzyl ester
<220> FEATURE:
<221> NAME/KEY: MISC_FEATURE
<222> LOCATION: (14)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (15)
<223> OTHER INFORMATION: Xaa = O-benzyl-L-threonine
<220> FEATURE:
<221> NAME/KEY: MISC_FEATURE
<222> LOCATION: (19)
<223> OTHER INFORMATION: Xaa = L-aspartic acid beta-benzyl ester
<220> FEATURE:
<221> NAME/KEY: MISC_FEATURE
<222> LOCATION: (21)
<223> OTHER INFORMATION: Xaa = glycine alpha-benzyl ester

<400> SEQUENCE: 41

Xaa Xaa Asn Xaa Xaa Asn Xaa Xaa Xaa Xaa Leu Xaa Phe Xaa Xaa Pro
1               5                   10                  15

Asn Asn Xaa Gly Xaa
            20

<210> SEQ ID NO 42
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-phenylalanine
<220> FEATURE:
<221> NAME/KEY: MISC_FEATURE
<222> LOCATION: (2)
<223> OTHER INFORMATION: Xaa = O-2,6-dichlorobenzyl-L-tyrosine
<220> FEATURE:
<221> NAME/KEY: MISC_FEATURE
<222> LOCATION: (4)
<223> OTHER INFORMATION: Xaa = O-benzyl-L-serine
<220> FEATURE:
<221> NAME/KEY: MISC_FEATURE
<222> LOCATION: (5)
```

-continued

```
<223> OTHER INFORMATION: Xaa = L-glutamic acid gamma-benzyl ester

<400> SEQUENCE: 42

Xaa Xaa Asn Xaa Xaa
1               5

<210> SEQ ID NO 43
<211> LENGTH: 16
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (2)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (3)
<223> OTHER INFORMATION: Xaa = O-benzyl-L-threonine
<220> FEATURE:
<221> NAME/KEY: MISC_FEATURE
<222> LOCATION: (4)
<223> OTHER INFORMATION: Xaa = O-2,6-dichlorobenzyl-L-tyrosine
<220> FEATURE:
<221> NAME/KEY: MISC_FEATURE
<222> LOCATION: (5)
<223> OTHER INFORMATION: Xaa = L-aspartic acid beta-benzyl ester
<220> FEATURE:
<221> NAME/KEY: MISC_FEATURE
<222> LOCATION: (7)
<223> OTHER INFORMATION: Xaa = L-aspartic acid beta-benzyl ester
<220> FEATURE:
<221> NAME/KEY: MISC_FEATURE
<222> LOCATION: (9)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (10)
<223> OTHER INFORMATION: Xaa = O-benzyl-L-threonine
<220> FEATURE:
<221> NAME/KEY: MISC_FEATURE
<222> LOCATION: (14)
<223> OTHER INFORMATION: Xaa = L-aspartic acid beta-benzyl ester
<220> FEATURE:
<221> NAME/KEY: MISC_FEATURE
<222> LOCATION: (16)
<223> OTHER INFORMATION: Xaa = glycine alpha-benzyl ester

<400> SEQUENCE: 43

Xaa Xaa Xaa Xaa Xaa Leu Xaa Phe Xaa Xaa Pro Asn Asn Xaa Gly Xaa
1               5                   10                  15

<210> SEQ ID NO 44
<211> LENGTH: 28
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-glutamic acid
      gamma-benzyl ester
<220> FEATURE:
<221> NAME/KEY: MISC_FEATURE
<222> LOCATION: (2)..(4)
<223> OTHER INFORMATION: Xaa = L-glutamic acid gamma-benzyl ester
<220> FEATURE:
<221> NAME/KEY: MISC_FEATURE
<222> LOCATION: (6)
<223> OTHER INFORMATION: Xaa = N-O-benzyl-L-serine
<220> FEATURE:
```

-continued

```
<221> NAME/KEY: MISC_FEATURE
<222> LOCATION: (7)
<223> OTHER INFORMATION: Xaa = L-glutamic acid gamma-benzyl ester
<220> FEATURE:
<221> NAME/KEY: MISC_FEATURE
<222> LOCATION: (9)
<223> OTHER INFORMATION: Xaa = O-2,6-dichlorobenzyl-L-tyrosine
<220> FEATURE:
<221> NAME/KEY: MISC_FEATURE
<222> LOCATION: (11)
<223> OTHER INFORMATION: Xaa = O-benzyl-L-serine
<220> FEATURE:
<221> NAME/KEY: MISC_FEATURE
<222> LOCATION: (12)
<223> OTHER INFORMATION: Xaa = N-L-glutamic acid gamma-benzyl ester
<220> FEATURE:
<221> NAME/KEY: MISC_FEATURE
<222> LOCATION: (14)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (15)
<223> OTHER INFORMATION: Xaa = O-benzyl-L-threonine
<220> FEATURE:
<221> NAME/KEY: MISC_FEATURE
<222> LOCATION: (16)
<223> OTHER INFORMATION: Xaa = O-2,6-dichlorobenzyl-L-tyrosine
<220> FEATURE:
<221> NAME/KEY: MISC_FEATURE
<222> LOCATION: (17)
<223> OTHER INFORMATION: Xaa = L-aspartic acid beta-benzyl ester
<220> FEATURE:
<221> NAME/KEY: MISC_FEATURE
<222> LOCATION: (19)
<223> OTHER INFORMATION: Xaa = L-aspartic acid beta-benzyl ester
<220> FEATURE:
<221> NAME/KEY: MISC_FEATURE
<222> LOCATION: (21)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (22)
<223> OTHER INFORMATION: Xaa = O-benzyl-L-threonine
<220> FEATURE:
<221> NAME/KEY: MISC_FEATURE
<222> LOCATION: (26)
<223> OTHER INFORMATION: Xaa = L-aspartic acid beta-benzyl ester
<220> FEATURE:
<221> NAME/KEY: MISC_FEATURE
<222> LOCATION: (28)
<223> OTHER INFORMATION: Xaa = glycine alpha-benzyl ester

<400> SEQUENCE: 44

Xaa Xaa Xaa Xaa Ala Xaa Xaa Phe Xaa Asn Xaa Xaa Asn Xaa Xaa Xaa
1               5                   10                  15

Xaa Leu Xaa Phe Xaa Xaa Pro Asn Asn Xaa Gly Xaa
            20                  25

<210> SEQ ID NO 45
<211> LENGTH: 7
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-glutamic acid
      gamma-benzyl ester
<220> FEATURE:
<221> NAME/KEY: MISC_FEATURE
<222> LOCATION: (2)..(4)
<223> OTHER INFORMATION: Xaa = L-glutamic acid gamma-benzyl ester
<220> FEATURE:
```

```
<221> NAME/KEY: MISC_FEATURE
<222> LOCATION: (6)
<223> OTHER INFORMATION: Xaa = O-benzyl-L-serine
<220> FEATURE:
<221> NAME/KEY: MISC_FEATURE
<222> LOCATION: (7)
<223> OTHER INFORMATION: Xaa = L-glutamic acid gamma-benzyl ester

<400> SEQUENCE: 45

Xaa Xaa Xaa Xaa Ala Xaa Xaa
1               5

<210> SEQ ID NO 46
<211> LENGTH: 7
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-glutamic acid
      gamma-benzyl ester
<220> FEATURE:
<221> NAME/KEY: MISC_FEATURE
<222> LOCATION: (2)..(4)
<223> OTHER INFORMATION: Xaa = L-glutamic acid gamma-benzyl ester
<220> FEATURE:
<221> NAME/KEY: MISC_FEATURE
<222> LOCATION: (6)
<223> OTHER INFORMATION: Xaa = O-benzyl-L-serine
<220> FEATURE:
<221> NAME/KEY: MISC_FEATURE
<222> LOCATION: (7)
<223> OTHER INFORMATION: Xaa = L-glutamic acid gamma-benzyl ester alpha-
      benzyl ester

<400> SEQUENCE: 46

Xaa Xaa Xaa Xaa Ala Xaa Xaa
1               5

<210> SEQ ID NO 47
<211> LENGTH: 21
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (2)
<223> OTHER INFORMATION: Xaa = O-2,6-dichlorobenzyl-L-tyrosine
<220> FEATURE:
<221> NAME/KEY: MISC_FEATURE
<222> LOCATION: (4)
<223> OTHER INFORMATION: Xaa = O-benzyl-L-serine
<220> FEATURE:
<221> NAME/KEY: MISC_FEATURE
<222> LOCATION: (5)
<223> OTHER INFORMATION: Xaa = L-glutamic acid gamma-benzyl ester
<220> FEATURE:
<221> NAME/KEY: MISC_FEATURE
<222> LOCATION: (7)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (8)
<223> OTHER INFORMATION: Xaa = O-benzyl-L-threonine
<220> FEATURE:
<221> NAME/KEY: MISC_FEATURE
<222> LOCATION: (9)
<223> OTHER INFORMATION: Xaa = O-2,6-dichlorobenzyl-L-tyrosine
<220> FEATURE:
<221> NAME/KEY: MISC_FEATURE
<222> LOCATION: (10)
```

<223> OTHER INFORMATION: Xaa = L-aspartic acid beta-benzyl ester
<220> FEATURE:
<221> NAME/KEY: MISC_FEATURE
<222> LOCATION: (12)
<223> OTHER INFORMATION: Xaa = L-aspartic acid beta-benzyl ester
<220> FEATURE:
<221> NAME/KEY: MISC_FEATURE
<222> LOCATION: (14)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (15)
<223> OTHER INFORMATION: Xaa = O-benzyl-L-threonine
<220> FEATURE:
<221> NAME/KEY: MISC_FEATURE
<222> LOCATION: (19)
<223> OTHER INFORMATION: Xaa = L-aspartic acid beta-benzyl ester
<220> FEATURE:
<221> NAME/KEY: MISC_FEATURE
<222> LOCATION: (21)
<223> OTHER INFORMATION: Xaa = glycine alpha-benzyl ester

<400> SEQUENCE: 47

Phe Xaa Asn Xaa Xaa Asn Xaa Xaa Xaa Xaa Leu Xaa Phe Xaa Xaa Pro
1               5                   10                  15

Asn Asn Xaa Gly Xaa
            20

<210> SEQ ID NO 48
<211> LENGTH: 26
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = S-acetamidomethyl-L-cysteine

<400> SEQUENCE: 48

Xaa Gly Gly Ala Ser Glu Phe Tyr Asn Ser Glu Asn Lys Thr Tyr Asp
1               5                   10                  15

Leu Asp Phe Lys Thr Pro Asn Asn Asp Gly
            20                  25

<210> SEQ ID NO 49
<211> LENGTH: 27
<212> TYPE: PRT
<213> ORGANISM: Artificial
<220> FEATURE:
<223> OTHER INFORMATION: artificial peptide

<400> SEQUENCE: 49

Cys Gly Gly Ala Ser Glu Phe Tyr Asn Ser Glu Asn Lys Thr Tyr Asp
1               5                   10                  15

Leu Asp Phe Lys Thr Pro Asn Asn Asp Gly Gly
            20                  25

<210> SEQ ID NO 50
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-asparagine
<220> FEATURE:

```
<221> NAME/KEY: MISC_FEATURE
<222> LOCATION: (3)
<223> OTHER INFORMATION: Xaa = L-aspartic acid beta-benzyl ester

<400> SEQUENCE: 50

Xaa Asn Xaa Asn
1

<210> SEQ ID NO 51
<211> LENGTH: 6
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-,
      S-acetamidomethyl-L-cysteine
<220> FEATURE:
<221> NAME/KEY: MISC_FEATURE
<222> LOCATION: (5)
<223> OTHER INFORMATION: Xaa = O-benzyl-L-serine
<220> FEATURE:
<221> NAME/KEY: MISC_FEATURE
<222> LOCATION: (6)
<223> OTHER INFORMATION: Xaa = L-glutamic acid gamma-benzyl ester alpha-
      trichloroethyl ester

<400> SEQUENCE: 51

Xaa Gly Gly Ala Xaa Xaa
1               5

<210> SEQ ID NO 52
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-glycine
<220> FEATURE:
<221> NAME/KEY: MISC_FEATURE
<222> LOCATION: (3)
<223> OTHER INFORMATION: Xaa = O-benzyl-L-serine
<220> FEATURE:
<221> NAME/KEY: MISC_FEATURE
<222> LOCATION: (4)
<223> OTHER INFORMATION: Xaa = L-glutamic acid gamma-benzyl ester alpha-
      trichloroethyl ester

<400> SEQUENCE: 52

Xaa Ala Xaa Xaa
1

<210> SEQ ID NO 53
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-glycine
<220> FEATURE:
<221> NAME/KEY: MISC_FEATURE
<222> LOCATION: (4)
<223> OTHER INFORMATION: Xaa = O-benzyl-L-serine
<220> FEATURE:
<221> NAME/KEY: MISC_FEATURE
```

```
<222> LOCATION: (5)
<223> OTHER INFORMATION: Xaa = L-glutamic acid gamma-benzyl ester alpha-
      trichloroethyl ester

<400> SEQUENCE: 53

Xaa Gly Ala Xaa Xaa
1               5

<210> SEQ ID NO 54
<211> LENGTH: 6
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = S-acetamidomethyl-L-cysteine
<220> FEATURE:
<221> NAME/KEY: MISC_FEATURE
<222> LOCATION: (5)
<223> OTHER INFORMATION: Xaa = O-benzyl-L-serine
<220> FEATURE:
<221> NAME/KEY: MISC_FEATURE
<222> LOCATION: (6)
<223> OTHER INFORMATION: Xaa = L-glutamic acid gamma-benzyl ester alpha-
      trichloroethyl ester

<400> SEQUENCE: 54

Xaa Gly Gly Ala Xaa Xaa
1               5

<210> SEQ ID NO 55
<211> LENGTH: 5
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (4)
<223> OTHER INFORMATION: Xaa = O-benzyl-L-serine
<220> FEATURE:
<221> NAME/KEY: MISC_FEATURE
<222> LOCATION: (5)
<223> OTHER INFORMATION: Xaa = L-glutamic acid gamma-benzyl ester alpha-
      trichloroethyl ester

<400> SEQUENCE: 55

Gly Gly Ala Xaa Xaa
1               5

<210> SEQ ID NO 56
<211> LENGTH: 9
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-aspartic acid
      O-benzyl ester
<220> FEATURE:
<221> NAME/KEY: MISC_FEATURE
<222> LOCATION: (3)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (4)
<223> OTHER INFORMATION: Xaa = O-benzyl-L-threonine
<220> FEATURE:
```

```
<221> NAME/KEY: MISC_FEATURE
<222> LOCATION: (8)
<223> OTHER INFORMATION: Xaa = L-aspartic acid beta-benzyl ester
<220> FEATURE:
<221> NAME/KEY: MISC_FEATURE
<222> LOCATION: (9)
<223> OTHER INFORMATION: Xaa = glycine alpha-trichloroethyl ester

<400> SEQUENCE: 56

Xaa Phe Xaa Xaa Pro Asn Asn Xaa Xaa
1               5

<210> SEQ ID NO 57
<211> LENGTH: 4
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (3)
<223> OTHER INFORMATION: Xaa = L-aspartic acid beta-benzyl ester
<220> FEATURE:
<221> NAME/KEY: MISC_FEATURE
<222> LOCATION: (4)
<223> OTHER INFORMATION: Xaa = glycine alpha-trichloroethyl ester

<400> SEQUENCE: 57

Asn Asn Xaa Xaa
1

<210> SEQ ID NO 58
<211> LENGTH: 15
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-asparagine
<220> FEATURE:
<221> NAME/KEY: MISC_FEATURE
<222> LOCATION: (2)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (3)
<223> OTHER INFORMATION: Xaa = O-benzyl-L-threonine
<220> FEATURE:
<221> NAME/KEY: MISC_FEATURE
<222> LOCATION: (4)
<223> OTHER INFORMATION: Xaa = O-2,6-dichlorobenzyl-L-tyrosine
<220> FEATURE:
<221> NAME/KEY: MISC_FEATURE
<222> LOCATION: (5)
<223> OTHER INFORMATION: Xaa = L-aspartic acid beta-benzyl ester
<220> FEATURE:
<221> NAME/KEY: MISC_FEATURE
<222> LOCATION: (7)
<223> OTHER INFORMATION: Xaa = L-aspartic acid beta-benzyl ester
<220> FEATURE:
<221> NAME/KEY: MISC_FEATURE
<222> LOCATION: (9)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (10)
<223> OTHER INFORMATION: Xaa = O-benzyl-L-threonine
<220> FEATURE:
<221> NAME/KEY: MISC_FEATURE
<222> LOCATION: (14)
<223> OTHER INFORMATION: Xaa = L-aspartic acid beta-benzyl ester
```

```
<220> FEATURE:
<221> NAME/KEY: MISC_FEATURE
<222> LOCATION: (15)
<223> OTHER INFORMATION: Xaa = glycine alpha-trichloroethyl ester

<400> SEQUENCE: 58

Xaa Xaa Xaa Xaa Xaa Leu Xaa Phe Xaa Xaa Pro Asn Asn Xaa Xaa
1               5                   10                  15

<210> SEQ ID NO 59
<211> LENGTH: 9
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = L-aspartic acid beta-benzyl ester
<220> FEATURE:
<221> NAME/KEY: MISC_FEATURE
<222> LOCATION: (3)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (4)
<223> OTHER INFORMATION: Xaa = O-benzyl-L-threonine
<220> FEATURE:
<221> NAME/KEY: MISC_FEATURE
<222> LOCATION: (8)
<223> OTHER INFORMATION: Xaa = L-aspartic acid beta-benzyl ester
<220> FEATURE:
<221> NAME/KEY: MISC_FEATURE
<222> LOCATION: (9)
<223> OTHER INFORMATION: Xaa = glycine alpha-trichloroethyl ester

<400> SEQUENCE: 59

Xaa Phe Xaa Xaa Pro Asn Asn Xaa Xaa
1               5

<210> SEQ ID NO 60
<211> LENGTH: 20
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-L-phenylalanine
<220> FEATURE:
<221> NAME/KEY: MISC_FEATURE
<222> LOCATION: (2)
<223> OTHER INFORMATION: Xaa = O-2,6-dichlorobenzyl-L-tyrosine
<220> FEATURE:
<221> NAME/KEY: MISC_FEATURE
<222> LOCATION: (4)
<223> OTHER INFORMATION: Xaa = O-benzyl-L-serine
<220> FEATURE:
<221> NAME/KEY: MISC_FEATURE
<222> LOCATION: (5)
<223> OTHER INFORMATION: Xaa = L-glutamic acid gamma-benzyl ester
<220> FEATURE:
<221> NAME/KEY: MISC_FEATURE
<222> LOCATION: (7)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (8)
<223> OTHER INFORMATION: Xaa = O-benzyl-L-threonine
<220> FEATURE:
<221> NAME/KEY: MISC_FEATURE
<222> LOCATION: (9)
```

```
<223> OTHER INFORMATION: Xaa = O-2,6-dichlorobenzyl-L-tyrosine
<220> FEATURE:
<221> NAME/KEY: MISC_FEATURE
<222> LOCATION: (10)
<223> OTHER INFORMATION: Xaa = L-aspartic acid beta-benzyl ester
<220> FEATURE:
<221> NAME/KEY: MISC_FEATURE
<222> LOCATION: (12)
<223> OTHER INFORMATION: Xaa = L-aspartic acid beta-benzyl ester
<220> FEATURE:
<221> NAME/KEY: MISC_FEATURE
<222> LOCATION: (14)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (15)
<223> OTHER INFORMATION: Xaa = O-benzyl-L-threonine
<220> FEATURE:
<221> NAME/KEY: MISC_FEATURE
<222> LOCATION: (19)
<223> OTHER INFORMATION: Xaa = L-aspartic acid beta-benzyl ester
<220> FEATURE:
<221> NAME/KEY: MISC_FEATURE
<222> LOCATION: (20)
<223> OTHER INFORMATION: Xaa = glycine alpha-trichloroethyl ester

<400> SEQUENCE: 60

Xaa Xaa Asn Xaa Xaa Asn Xaa Xaa Xaa Xaa Leu Xaa Phe Xaa Xaa Pro
1               5                   10                  15

Asn Asn Xaa Xaa
            20

<210> SEQ ID NO 61
<211> LENGTH: 15
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (2)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (3)
<223> OTHER INFORMATION: Xaa = O-benzyl-L-threonine
<220> FEATURE:
<221> NAME/KEY: MISC_FEATURE
<222> LOCATION: (4)
<223> OTHER INFORMATION: Xaa = O-2,6-dichlorobenzyl-L-tyrosine
<220> FEATURE:
<221> NAME/KEY: MISC_FEATURE
<222> LOCATION: (5)
<223> OTHER INFORMATION: Xaa = L-aspartic acid beta-benzyl ester
<220> FEATURE:
<221> NAME/KEY: MISC_FEATURE
<222> LOCATION: (7)
<223> OTHER INFORMATION: Xaa = L-aspartic acid beta-benzyl ester
<220> FEATURE:
<221> NAME/KEY: MISC_FEATURE
<222> LOCATION: (9)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (10)
<223> OTHER INFORMATION: Xaa = O-benzyl-L-threonine
<220> FEATURE:
<221> NAME/KEY: MISC_FEATURE
<222> LOCATION: (14)
<223> OTHER INFORMATION: Xaa = L-aspartic acid beta-benzyl ester
<220> FEATURE:
<221> NAME/KEY: MISC_FEATURE
<222> LOCATION: (15)
```

<223> OTHER INFORMATION: Xaa = glycine alpha-trichloroethyl ester

<400> SEQUENCE: 61

Asn Xaa Xaa Xaa Xaa Leu Xaa Phe Xaa Xaa Pro Asn Asn Xaa Xaa
1               5                   10                  15

<210> SEQ ID NO 62
<211> LENGTH: 26
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-,
      S-acetamidomethyl-L-cysteine
<220> FEATURE:
<221> NAME/KEY: MISC_FEATURE
<222> LOCATION: (5)
<223> OTHER INFORMATION: Xaa = O-benzyl-L-serine
<220> FEATURE:
<221> NAME/KEY: MISC_FEATURE
<222> LOCATION: (6)
<223> OTHER INFORMATION: Xaa = L-glutamic acid gamma-benzyl ester
<220> FEATURE:
<221> NAME/KEY: MISC_FEATURE
<222> LOCATION: (8)
<223> OTHER INFORMATION: Xaa = O-2,6-dichlorobenzyl-L-tyrosine
<220> FEATURE:
<221> NAME/KEY: MISC_FEATURE
<222> LOCATION: (10)
<223> OTHER INFORMATION: Xaa = O-benzyl-L-serine
<220> FEATURE:
<221> NAME/KEY: MISC_FEATURE
<222> LOCATION: (11)
<223> OTHER INFORMATION: Xaa = L-glutamic acid gamma-benzyl ester
<220> FEATURE:
<221> NAME/KEY: MISC_FEATURE
<222> LOCATION: (13)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (14)
<223> OTHER INFORMATION: Xaa = O-benzyl-L-threonine
<220> FEATURE:
<221> NAME/KEY: MISC_FEATURE
<222> LOCATION: (15)
<223> OTHER INFORMATION: Xaa = O-2,6-dichlorobenzyl-L-tyrosine
<220> FEATURE:
<221> NAME/KEY: MISC_FEATURE
<222> LOCATION: (16)
<223> OTHER INFORMATION: Xaa = L-aspartic acid beta-benzyl ester
<220> FEATURE:
<221> NAME/KEY: MISC_FEATURE
<222> LOCATION: (18)
<223> OTHER INFORMATION: Xaa = L-aspartic acid beta-benzyl ester
<220> FEATURE:
<221> NAME/KEY: MISC_FEATURE
<222> LOCATION: (20)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (21)
<223> OTHER INFORMATION: Xaa = O-benzyl-L-threonine
<220> FEATURE:
<221> NAME/KEY: MISC_FEATURE
<222> LOCATION: (25)
<223> OTHER INFORMATION: Xaa = L-aspartic acid beta-benzyl ester
<220> FEATURE:
<221> NAME/KEY: MISC_FEATURE
<222> LOCATION: (26)
<223> OTHER INFORMATION: Xaa = glycine alpha-trichloroethyl ester

<400> SEQUENCE: 62

-continued

```
Xaa Gly Gly Ala Xaa Xaa Phe Xaa Asn Xaa Xaa Asn Xaa Xaa Xaa Xaa
1               5                   10                  15

Leu Xaa Phe Xaa Xaa Pro Asn Asn Xaa Xaa
            20                  25

<210> SEQ ID NO 63
<211> LENGTH: 6
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-,
      S-acetamidomethyl-L-cysteine
<220> FEATURE:
<221> NAME/KEY: MISC_FEATURE
<222> LOCATION: (5)
<223> OTHER INFORMATION: Xaa = O-benzyl-L-serine
<220> FEATURE:
<221> NAME/KEY: MISC_FEATURE
<222> LOCATION: (6)
<223> OTHER INFORMATION: Xaa = L-glutamic acid gamma-benzyl ester

<400> SEQUENCE: 63

Xaa Gly Gly Ala Xaa Xaa
1               5

<210> SEQ ID NO 64
<211> LENGTH: 21
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = L-glutamic acid gamma-benzyl ester
<220> FEATURE:
<221> NAME/KEY: MISC_FEATURE
<222> LOCATION: (3)
<223> OTHER INFORMATION: Xaa = O-2,6-dichlorobenzyl-L-tyrosine
<220> FEATURE:
<221> NAME/KEY: MISC_FEATURE
<222> LOCATION: (5)
<223> OTHER INFORMATION: Xaa = O-benzyl-L-serine
<220> FEATURE:
<221> NAME/KEY: MISC_FEATURE
<222> LOCATION: (6)
<223> OTHER INFORMATION: Xaa = L-glutamic acid gamma-benzyl ester
<220> FEATURE:
<221> NAME/KEY: MISC_FEATURE
<222> LOCATION: (8)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (9)
<223> OTHER INFORMATION: Xaa = O-benzyl-L-threonine
<220> FEATURE:
<221> NAME/KEY: MISC_FEATURE
<222> LOCATION: (10)
<223> OTHER INFORMATION: Xaa = O-2,6-dichlorobenzyl-L-tyrosine
<220> FEATURE:
<221> NAME/KEY: MISC_FEATURE
<222> LOCATION: (11)
<223> OTHER INFORMATION: Xaa = L-aspartic acid beta-benzyl ester
<220> FEATURE:
<221> NAME/KEY: MISC_FEATURE
<222> LOCATION: (13)
<223> OTHER INFORMATION: Xaa = L-aspartic acid beta-benzyl ester
<220> FEATURE:
<221> NAME/KEY: MISC_FEATURE
```

```
<222> LOCATION: (15)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (16)
<223> OTHER INFORMATION: Xaa = O-benzyl-L-threonine
<220> FEATURE:
<221> NAME/KEY: MISC_FEATURE
<222> LOCATION: (20)
<223> OTHER INFORMATION: Xaa = L-aspartic acid beta-benzyl ester
<220> FEATURE:
<221> NAME/KEY: MISC_FEATURE
<222> LOCATION: (21)
<223> OTHER INFORMATION: Xaa = glycine alpha-trichloroethyl ester

<400> SEQUENCE: 64

Xaa Phe Xaa Asn Xaa Xaa Asn Xaa Xaa Xaa Xaa Leu Xaa Phe Xaa Xaa
1               5                   10                  15

Pro Asn Asn Xaa Xaa
            20

<210> SEQ ID NO 65
<211> LENGTH: 26
<212> TYPE: PRT
<213> ORGANISM: Artificial
<220> FEATURE:
<223> OTHER INFORMATION: artificial peptide
<220> FEATURE:
<221> NAME/KEY: MISC_FEATURE
<222> LOCATION: (1)
<223> OTHER INFORMATION: Xaa = N-alpha-t-butoxycarbonyl-,
      S-acetamidomethyl-L-cysteine
<220> FEATURE:
<221> NAME/KEY: MISC_FEATURE
<222> LOCATION: (5)
<223> OTHER INFORMATION: Xaa = O-benzyl-L-serine
<220> FEATURE:
<221> NAME/KEY: MISC_FEATURE
<222> LOCATION: (6)
<223> OTHER INFORMATION: Xaa = L-glutamic acid gamma-benzyl ester
<220> FEATURE:
<221> NAME/KEY: MISC_FEATURE
<222> LOCATION: (8)
<223> OTHER INFORMATION: Xaa = O-2,6-dichlorobenzyl-L-tyrosine
<220> FEATURE:
<221> NAME/KEY: MISC_FEATURE
<222> LOCATION: (10)
<223> OTHER INFORMATION: Xaa = O-benzyl-L-serine
<220> FEATURE:
<221> NAME/KEY: MISC_FEATURE
<222> LOCATION: (11)
<223> OTHER INFORMATION: Xaa = L-glutamic acid gamma-benzyl ester
<220> FEATURE:
<221> NAME/KEY: MISC_FEATURE
<222> LOCATION: (13)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (14)
<223> OTHER INFORMATION: Xaa = O-benzyl-L-threonine
<220> FEATURE:
<221> NAME/KEY: MISC_FEATURE
<222> LOCATION: (15)
<223> OTHER INFORMATION: Xaa = O-2,6-dichlorobenzyl-L-tyrosine
<220> FEATURE:
<221> NAME/KEY: MISC_FEATURE
<222> LOCATION: (16)
<223> OTHER INFORMATION: Xaa = L-aspartic acid beta-benzyl ester
<220> FEATURE:
<221> NAME/KEY: MISC_FEATURE
<222> LOCATION: (18)
<223> OTHER INFORMATION: Xaa = L-aspartic acid beta-benzyl ester
<220> FEATURE:
<221> NAME/KEY: MISC_FEATURE
```

```
<222> LOCATION: (20)
<223> OTHER INFORMATION: Xaa = N-epsilon-2-chlorobenzyloxycarbonyl-L-
      lysine
<220> FEATURE:
<221> NAME/KEY: MISC_FEATURE
<222> LOCATION: (21)
<223> OTHER INFORMATION: Xaa = O-benzyl-L-threonine
<220> FEATURE:
<221> NAME/KEY: MISC_FEATURE
<222> LOCATION: (25)
<223> OTHER INFORMATION: Xaa = L-aspartic acid beta-benzyl ester

<400> SEQUENCE: 65

Xaa Gly Gly Ala Xaa Xaa Phe Xaa Asn Xaa Xaa Asn Xaa Xaa Xaa Xaa
1               5                   10                  15

Leu Xaa Phe Xaa Xaa Pro Asn Asn Xaa Gly
            20                  25
```